(12) United States Patent
Gallagher et al.

(10) Patent No.: US 10,416,172 B2
(45) Date of Patent: Sep. 17, 2019

(54) RECOMBINANT SOLUBLE TRUNCATED IL-23 RECEPTOR (IL-23R) CAPABLE OF INHIBITING IL-23R-MEDIATED CELL SIGNALING

(75) Inventors: Grant Gallagher, Milltown, NJ (US); Raymond Yu, East Brunswick, NJ (US); Jonathan Brazaitis, Parlin, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 345 days.

(21) Appl. No.: 13/065,878

(22) Filed: Mar. 31, 2011

(65) Prior Publication Data

US 2012/0071422 A1    Mar. 22, 2012

Related U.S. Application Data

(60) Provisional application No. 61/341,457, filed on Mar. 31, 2010, provisional application No. 61/341,465, filed on Mar. 31, 2010.

(51) Int. Cl.
| | |
|---|---|
| *A61K 38/00* | (2006.01) |
| *G01N 33/68* | (2006.01) |
| *C07K 14/715* | (2006.01) |
| *C12N 5/071* | (2010.01) |

(52) U.S. Cl.
CPC ..... *G01N 33/6893* (2013.01); *C07K 14/7155* (2013.01); *C12N 5/0602* (2013.01); *G01N 33/6863* (2013.01); *A61K 38/00* (2013.01); *G01N 2333/705* (2013.01); *G01N 2800/065* (2013.01); *G01N 2800/368* (2013.01)

(58) Field of Classification Search
None
See application file for complete search history.

(56) References Cited

U.S. PATENT DOCUMENTS

2003/0059871 A1* 3/2003 Cosman et al. ............. 435/69.1

OTHER PUBLICATIONS

Locus AM990321 by Kan et al., Nov. 1, 2008.*
Locus AM990318 by Kan et al., Nov. 1, 2008.*
Vaknin-Dembinsky et al. IL-23 Is Increased in Dendritic Cells in Multiple Sclerosis and Down-Regulation of IL-23 by Antisense Oligos Increases Dendritic Cell IL-10 Production. J. Immunol., 2006, 176: 7768-7774.*
Locus NM_144701 from GenBank, "*Homo sapiens* interleukin 23 receptor (IL23R), mRNA". Accessed Feb. 15, 2015.*
Langrish, Claire L., et al., JEM, vol. 201, Jan. 17, 2005, pp. 233-240.
Harrington, Laurie E., et al., Nature Immunology, vol. 6, No. 11, Nov. 2005, pp. 1123-1132.
Abraham, Clara and Cho, Judy, Inflamm. Bowel Dis., vol. 15, No. 7, Jul. 2009, pp. 1090-1011.
Oppmann, Birgit, et al., Immunity, vol. 13, Nov. 2000, pp. 715-725.
Parham, Christi, et al., The Journal of Immunology, vol. 168, 2002, pp. 5699-5708.
Aggarwal, Sudeepta, et al., The Journal of Biological Chemistry, vol. 278, No. 3, Jan. 17, 2003, pp. 1910-1914.
Yang, Xuexian O., et al., Journal of Biological Chemistry, vol. 282, No. 13, Mar. 30, 2007, pp. 9358-9363.
Korn, Thomas, et al., Seminars in Immunology, vol. 19, 2007, pp. 362-371.
Ouyang, Wenjun, et al., Immunity, vol. 28, Apr. 2008, pp. 454-467.
Louten, Jennifer, et al., J. Allergy Clin. Immunol. vol. 123, No. 5, 2009, pp. 1004-1011.
Mangan, Paul R., et al., Nature, vol. 441, May 11, 2006, pp. 231-234.
Veldoen, Marc, et al., Immunity, vol. 24, Feb. 2006, pp. 179-189.
Wei, Lai, et al., The Journal of Biological Chemistry, vol. 282, No. 48, Nov. 30, 2007, pp. 34605-34610.
Zhou Liang, et al., Nature Immunology, vol. 8, No. 9, Sep. 2007, pp. 967-974.
Ivanov, Ivaylo I., et al., Cell, vol. 126, Sep. 22, 2006, pp. 1121-1133.
Yang Xuexian O., et al., Immunity, vol. 28, Jan. 2008, pp. 29-39.
Abraham, Clara and Cho, Judy, Inflammatory Bowel Diseases, vol. 15, No. 7, Jul. 2009, pp. 1090-1100.
Chan, Jason R., et al., JEM, vol. 203, No. 12, Nov. 27, 2006, pp. 2577-2587.
Murphy, Craig A., et al., JEM, vol. 198, No. 12, Dec. 15, 2003, pp. 1951-1957.
Wong, Chun Kwok, et al., Clinical Immunology, vol. 127, 2008, pp. 385-393.
Cardoso, C. R., et al., Oral Microbiology and Immunology, vol. 24, No. 1, Feb. 2009, pp. 1-6.
Elson, Charles O., et al., Gastroenterology, vol. 132, 2007, pp. 2359-2370.

(Continued)

*Primary Examiner* — Dong Jiang
(74) *Attorney, Agent, or Firm* — Terence Bogie; Arnold Braun

(57) ABSTRACT

The present invention relates to an isolated naturally-occurring soluble truncated IL-23Rα protein, which is a translated protein resulting from a mRNA splice variant of IL-23Rα. The soluble IL-23Rα proteins (e.g., Δ9 and Δ8,9) represents a novel soluble IL-23Rα protein, which is lacking a transmembrane domain and has a unique eight (8) amino acids (GLKEGSYC) at its C-terminus end (due to frame-shift). ELISA reveals that Δ9 is present in blood and can serve as a diagnostic tool for auto-immune diseases including Crohn's disease. There is also provided a method of recombinant production for this soluble truncated form of IL-23Rα protein. More importantly, the present invention provides an utility application of the Δ9 and Δ8,9 protein in inhibit IL-23R-mediated cell signaling. More particularly, Δ9 and Δ8,9 blocks STAT3 formation as well as Th17 maturation. There is provided a therapeutic application of Δ9 and Δ8,9 in treating a human patient inflicted with Crohn's disease.

14 Claims, 39 Drawing Sheets
Specification includes a Sequence Listing.

(56) References Cited

OTHER PUBLICATIONS

Duerr, Richard H., et al., Science, vol. 314, 2006, pp. 1461-1463.
Cargill, Michele, et al., The American Journal of Human Genetics, vol. 80, Feb. 2007, pp. 273-290.
Farago, B., et al., Ann. Rheum. Dis. vol. 67, 2008, pp. 248-250.
Kan, S-H, et al., Genes and Immunity, vol. 9, 2008, pp. 631-639.
Mancini, G., et al., Genes and Immunity, vol. 9, 2008, pp. 566-569.
Presky, David H., et al., Proc. Natl. Acad. Sci., vol. 93, Nov. 1996, pp. 14002-14007.
Cua, Daniel J., et al., Nature, vol. 42, Feb. 13, 2003, pp. 744-748.
Murphy, Kenneth M. and Reiner, Steven L., Nature, vol. 2, Dec. 2002, pp. 933-944.
Liang, Spencer C., et al., JEM, vol. 203, No. 10, Oct. 2, 2006, pp. 2271-2279.
Harrington, Laurie E., et al., Current Opinion in Immunology, vol. 18, 2006, pp. 349-356.
Fujino, S. et al., Gut, vol. 52, 2003, pp. 65-70.
Zheng, Yan, et al., Nature, vol. 445, Feb. 8, 2007, pp. 648-651.

\* cited by examiner

Figure 3A

>Nucleotide (SEQ ID NO: 1)
ATGAATCAGGTCACTATTCAATGGGATGCAGTAATAGCCCTTTACATACTCTTCA
GCTGGTGTCATGGAGGAATTACAAATATAAACTGCTCTGGCCACATCTGGGTAGA
ACCAGCCACAATTTTTAAGATGGGTATGAATATCTCTATATATTGCCAAGCAGCA
ATTAAGAACTGCCAACCAAGGAAACTTCATTTTTATAAAAATGGCATCAAAGAAA
GATTTCAAATCACAAGGATTAATAAAACAACAGCTCGGCTTTGGTATAAAAACTT
TCTGGAACCACATGCTTCTATGTACTGCACTGCTGAATGTCCCAAACATTTTCAA
GAGACACTGATATGTGGAAAGACATTTCTTCTGGATATCCGCCAGATATTCCTG
ATGAAGTAACCTGTGTCATTTATGAATATTCAGGCAACATGACTTGCACCTGGAA
TGCTGGGAAGCTCACCTACATAGACACAAAATACGTGGTACATGTGAAGAGTTTA
GAGACAGAAGAAGAGCAACAGTATCTCACCTCAAGCTATATTAACATCTCCACTG
ATTCATTACAAGGTGGCAAGAAGTACTTGGTTTGGGTCCAAGCAGCAAACGCACT
AGGCATGGAAGAGTCAAAACAACTGCAAATTCACCTGGATGATATAGTGATACCT
TCTGCAGCCGTCATTTCCAGGGCTGAGACTATAAATGCTACAGTGCCCAAGACCA
TAATTTATTGGGATAGTCAAACAACAATTGAAAAGGTTTCCTGTGAAATGAGATA
CAAGGCTACAACAAACCAAACTTGGAATGTTAAAGAATTTGACACCAATTTTACA
TATGTGCAACAGTCAGAATTCTACTTGGAGCCAAACATTAAGTACGTATTTCAAG
TGAGATGTCAAGAAACAGGCAAAAGGTACTGGCAGCCTTGGAGTTCACTGTTTTT
TCATAAAACACCTGAAACAGTTCCCCAGGTCACATCAAAAGCATTCCAACATGAC
ACATGGAATTCTGGGCTAACAGTTGCTTCCATCTCTACAGGGCACCTTACTTCTG
GATTAAAAGAAGGATCTTATTGTTAA >Protein
Δ9 (SEQ ID NO: 2)
MNQVTIQWDAVIALYILFSWCHGGITNINCSGHIWVEPATIFKMGMNISIYCQAAI
KNCQPRKLHFYKNGIKERFQITRINKTTARLWYKNFLEPHASMYCTAECPKHFQ
ETLICGKDISSGYPPDIPDEVTCVIYEYSGNMTCTWNAGKLTYIDTKYVVHVKSL
ETEEEQQYLTSSYINISTDSLQGGKKYLVWVQAANALGMEESKQLQIHLDDIVIP
SAAVISRAETINATVPKTIIYWDSQTTIEKVSCEMRYKATTNQTWNVKEFDTNFT
YVQQSEFYLEPNIKYVFQVRCQETGKRYWQPWSSLFFHKTPETVPQVTSKAFQH
DTWNSGLTVASISTGHLTSGLKEGSYC

Figure 3B

```
Wild-type  (SEQ ID NO: 41)
Δ9         (SEQ ID NO: 2)
```

Cleavage site
              Signal peptide       ↓
Wild-type  |MNQVTIQWDA VIALYILFSW CHG|GITNINC SGHIWVEPAT IFKMGMNISI
Δ9         |MNQVTIQWDA VIALYILFSW CHG|GITNINC SGHIWVEPAT IFKMGMNISI Wild-type  YCQAAIKNCQ PRKLHFYKNG IKERFQITRI NKTTARLWYK NFLEPHASMY
Δ9         YCQAAIKNCQ PRKLHFYKNG IKERFQITRI NKTTARLWYK NFLEPHASMY Wild-type  CTAECPKHFQ ETLICGKDIS SGYPPDIPDE VTCVIYEYSG NMTCTWNAGK
Δ9         CTAECPKHFQ ETLICGKDIS SGYPPDIPDE VTCVIYEYSG NMTCTWNAGK Wild-type  LTYIDTKYVV HVKSLETEEE QQYLTSSYIN ISTDSLQGGK KYLVWVQAAN
Δ9         LTYIDTKYVV HVKSLETEEE QQYLTSSYIN ISTDSLQGGK KYLVWVQAAN Wild-type  ALGMEESKQL QIHLDDIVIP SAAVISRAET INATVPKTII YWDSQTTIEK
Δ9         ALGMEESKQL QIHLDDIVIP SAAVISRAET INATVPKTII YWDSQTTIEK Wild-type  VSCEMRYKAT TNQTWNVKEF DTNFTYVQQS EFYLEPNIKY VFQVRCQETG
Δ9         VSCEMRYKAT TNQTWNVKEF DTNFTYVQQS EFYLEPNIKY VFQVRCQETG Wild-type  KRYWQPWSSL FFHKTPETVP QVTSKAFQHD TWNSGLTVAS ISTGHLTSDN
Δ9         KRYWQPWSSL FFHKTPETVP QVTSKAFQHD TWNSGLTVAS ISTGHLTS--

Transmembrane domain
Wild-type  RGD|IGLLLGM IVFAVMLSIL SLIGIF|NRSF RTGIKRRILL LIPKWLYEDI
Δ9         ---------- ---------- ---------- ---------- ----------

Wild-type  PNMKNSNVVK MLQENSELMN NNSSEQVLYV DPMITEIKEI FIPEHKPTDY
Δ9         ---------- ---------- ---------- ---------- ----------

Wild-type  KKENTGPLET RDYPQNSLFD NTTVVYIPDL NTGYKPQISN FLPEGSHLSN
Δ9         ---------- ---------- ---------- ---------- ----------

Wild-type  NNEITSLTLK PPVDSLDSGN NPRLQKHPNF AFSVSSVNSL SNTIFLGELS
Δ9         ---------- ---------- ---------- ---------- ----------

Wild-type  LILNQGECSS PDIQNSVEEE TTMLLENDSP SETIPEQTLL PDEFVSCLGI
Δ9         ---------- ---------- ---------- ---------- ----------

Wild-type  VNEELPSINT YFPQNILESH FNRISLLEK- -------
Δ9         ---------- ---------- ---------G LKEGSYC
                                          ‾‾‾‾‾‾‾‾‾
                                          Extra 8 amino acids

Figure 3D

>Nucleotide (SEQ ID NO: 3)
ATGAATCAGGTCACTATTCAATGGGATGCAGTAATAGCCCTTTACATACTCTTCA
GCTGGTGTCATGGAGGAATTACAAATATAAACTGCTCTGGCCACATCTGGGTAGA
ACCAGCCACAATTTTTAAGATGGGTATGAATATCTCTATATATTGCCAAGCAGCA
ATTAAGAACTGCCAACCAAGGAAACTTCATTTTTATAAAAATGGCATCAAAGAAA
GATTTCAAATCACAAGGATTAATAAAACAACAGCTCGGCTTTGGTATAAAAACTT
TCTGGAACCACATGCTTCTATGTACTGCACTGCTGAATGTCCCAAACATTTTCAA
GAGACACTGATATGTGGAAAAGACATTTCTTCTGGATATCCGCCAGATATTCCTG
ATGAAGTAACCTGTGTCATTTATGAATATTCAGGCAACATGACTTGCACCTGGAA
TGCTGGGAAGCTCACCTACATAGACACAAAATACGTGGTACATGTGAAGAGTTTA
GAGACAGAAGAAGAGCAACAGTATCTCACCTCAAGCTATATTAACATCTCCACTG
ATTCATTACAAGGTGGCAAGAAGTACTTGGTTTGGGTCCAAGCAGCAAACGCACT
AGGCATGGAAGAGTCAAAACAACTGCAAATTCACCTGGATGATATAGTGATACCT
TCTGCAGCCGTCATTTCCAGGGCTGAGACTATAAATGCTACAGTGCCCAAGACCA
TAATTTATTGGGATAGTCAAACAACAATTGAAAAGGTTTCCTGTGAAATGAGATA
CAAGGCTACAACAAACCAAACTTGGAATGTTAAAGAATTTGACACCAATTTTACA
TATGTGCAACAGTCAGAATTCTACTTGGAGCCAAACATTAAGTACGTATTTCAAG
TGAGATGTCAAGAAACAGGCAAAAGGTACTGGCAGCCTTGGAGTTCACTGTTTTT
TCATAAAACACCTGAAACAGGATTAAAAGAAGGATCTTATTGTTAA >Protein
Δ8,9 (SEQ ID NO: 4)
MNQVTIQWDAVIALYILFSWCHGGITNINCSGHIWVEPATIFKMGMNISIYCQAAI
KNCQPRKLHFYKNGIKERFQITRINKTTARLWYKNFLEPHASMYCTAECPKHFQ
ETLICGKDISSGYPPDIPDEVTCVIYEYSGNMTCTWNAGKLTYIDTKYVVHVKSL
ETEEEQQYLTSSYINISTDSLQGGKKYLVWVQAANALGMEESKQLQIHLDDIVIP
SAAVISRAETINATVPKTIIYWDSQTTIEKVSCEMRYKATTNQTWNVKEFDTNFT
YVQQSEFYLEPNIKYVFQVRCQETGKRYWQPWSSLFFHKTPETGLKEGSYC

Figure 3E

```
Wild-type  (SEQ ID NO: 41)
Δ8,9       (SEQ ID NO: 4)
                                      Cleavage site
           Signal peptide                   ↓
Wild-type  MNQVTIQWDA VIALYILFSW CHGGITNINC SGHIWVEPAT IFKMGMNISI
Δ8,9       MNQVTIQWDA VIALYILFSW CHGGITNINC SGHIWVEPAT IFKMGMNISI Wild-type  YCQAAIKNCQ PRKLHFYKNG IKERFQITRI NKTTARLWYK NFLEPHASMY
Δ8,9       YCQAAIKNCQ PRKLHFYKNG IKERFQITRI NKTTARLWYK NFLEPHASMY Wild-type  CTAECPKHFQ ETLICGKDIS SGYPPDIPDE VTCVIYEYSG NMTCTWNAGK
Δ8,9       CTAECPKHFQ ETLICGKDIS SGYPPDIPDE VTCVIYEYSG NMTCTWNAGK Wild-type  LTYIDTKYVV HVKSLETEEE QQYLTSSYIN ISTDSLQGGK KYLVWVQAAN
Δ8,9       LTYIDTKYVV HVKSLETEEE QQYLTSSYIN ISTDSLQGGK KYLVWVQAAN Wild-type  ALGMEESKQL QIHLDDIVIP SAAVISRAET INATVPKTII YWDSQTTIEK
Δ8,9       ALGMEESKQL QIHLDDIVIP SAAVISRAET INATVPKTII YWDSQTTIEK Wild-type  VSCEMRYKAT TNQTWNVKEF DTNFTYVQQS EFYLEPNIKY VFQVRCQETG
Δ8,9       VSCEMRYKAT TNQTWNVKEF DTNFTYVQQS EFYLEPNIKY VFQVRCQETG Wild-type  KRYWQPWSSL FFHKTPETVP QVTSKAFQHD TWNSGLTVAS ISTGHLTSDN
Δ8,9       KRYWQPWSSL FFHKTPET-- ---------- ---------- ----------
                 Transmembrane domain
Wild-type  RGDIGLLLGM IVFAVMLSIL SLIGIFNRSF RTGIKRRILL LIPKWLYEDI
Δ8,9       ---------- ---------- ---------- ---------- ----------

Wild-type  PNMKNSNVVK MLQENSELMN NNSSEQVLYV DPMITEIKEI FIPEHKPTDY
Δ8,9       ---------- ---------- ---------- ---------- ----------

Wild-type  KKENTGPLET RDYPQNSLFD NTTVVYIPDL NTGYKPQISN FLPEGSHLSN
Δ8,9       ---------- ---------- ---------- ---------- ----------

Wild-type  NNEITSLTLK PPVDSLDSGN NPRLQKHPNF AFSVSSVNSL SNTIFLGELS
Δ8,9       ---------- ---------- ---------- ---------- ----------

Wild-type  LILNQGECSS PDIQNSVEEE TTMLLENDSP SETIPEQTLL PDEFVSCLGI
Δ8,9       ---------- ---------- ---------- ---------- ----------

Wild-type  VNEELPSINT YFPQNILESH FNRISLLEK- --------
Δ8,9       ---------- ---------- ---------G LKEGSYC
                                            Extra 8 amino acids
```

RECOMBINANT SOLUBLE TRUNCATED IL-23 RECEPTOR (IL-23R) CAPABLE OF INHIBITING IL-23R-MEDIATED CELL SIGNALING

CROSS-REFERENCE TO RELATED APPLICATIONS

This application claims the benefit under 35 U.S.C. § 119(e) to U.S. Provisional Application Nos. 61/341,465 and 61/341,457 filed Mar. 31, 2010, the contents of which are incorporated by reference herein in their entireties.

FIELD OF THE INVENTION

The present invention relates to a therapeutic application of an isolated recombinant IL-23 receptor (IL-23Rα). This particular recombinant IL-23Rα is discovered as a soluble translated form (e.g., Δ9 or Δ8,9) as a result of the alternative splicing of the IL-23Rα gene. It exists as a naturally-occurring soluble truncated form of IL-23Rα. The soluble translated IL-23Rα has a unique eight (8) amino acid sequence (GLKEGSYC) at its C-terminus, due to the alternative translation reading frame on exon 10. The present invention provides a soluble truncated IL-23Rα that is useful as a therapeutic agent to inhibit cell signaling mediated by IL-23 necessary for differentiation of Th17 cells in immunological diseases including inflammatory bowel diseases (e.g., Crohn's disease), asthma, and other pathological diseases (e.g., graft vs. host disease).

BACKGROUND OF THE INVENTION

IL-23 is a heterodimeric molecule comprising a p19 subunit and a p40 subunit that are two disulfide-linked. IL-23 is speculated to play an essential role in chronic inflammation and autoimmune diseases in humans. Mice lacking p19 exhibit a decreased pro-inflammatory response to experimental autoimmune encephalomyelitis, inflammatory bowel disease and collagen-induced arthritis. While IL-23 per se cannot induce the differentiation of naïve CD4 T-cells into Th-17 cells in vitro, the differentiation of Th17 cells in vivo may require IL-23. The observed protective effect in p19-deficient mice may relate to the lack of differentiation of Th17 cells. This is consistent with recent report that IL-23 synergies with Th17 cell differentiation cytokines including IL-6 and TGF-β to induce expression of IL-17.

IL-23 exerts its biological activities by binding to IL-23 receptor (IL-23R). IL-23R comprises an IL-23Rα subunit and an IL-12Rβ1 subunit. When IL-23 binds to IL-23R, it leads to intracellular signaling including phosphorylation of STAT1, STAT3, STAT4 and STAT5. IL-23R is expressed on T-cells, NK cells, monocytes, and dendritic cells and its expression pattern corresponds with the ability of these cells to respond to IL-23.

Human IL-23Rα mRNA is 2.8 kb long and contains 11 exons (NM_144701). The translated full-length IL-23Rα protein is a type-I transmembrane protein (629 amino acids) and contains three (3) structural domains: (1) a signal peptide domain; (2) an extracellular region containing a N-terminal fibronectin III-like domain; and (3) a 253 amino acid residue cytoplasmic domain with three (3) potential tyrosine phosphorylation sites.

Christi Parham et al. first discovered the genomic and structural organization of the IL-23R (composed of an IL-23α subunit and an IL-12Rβ1 subunit). While IL-23 is shown to bind to IL-23R and mediates Jak-STAT cell signaling, Parham explicitly stated their inability to demonstrate human IL-23Rα-Ig and soluble human IL-23Rα-V5-His6 (composed of the entire extracellular domain—amino acids 1-353) as effective antagonists for human IL-23R. Daniel J. Cua et al. disclose treatment methods for multiple sclerosis, neuropathic pain, and inflammatory bowel disorders using antibodies against IL-23 and its receptor. Contrary to Parham's statement, Cua et al. propose using a soluble receptor based on the extracellular region of a subunit of the IL-23 receptor (PCT/US2004/003126) as an antagonist. A recombinant human IL-23Rα Fc chimeric protein is commercially available (R&D Systems) and claimed to have the ability to inhibit IL-23 induced IL-17 secretion in a mouse splenocytes system. It remains unclear as to whether any of these proposed soluble IL-23Rαs may in fact exist in vivo as a naturally-occurring protein, let alone the possibility that such soluble IL-23Rαs may possess ability to block IL-23Rα mediated cell signaling. To this end, Daniel J. Cua et al. (PCT/US2004/003126) failed to provide any evidence that a soluble IL-23 receptor can indeed block IL-23 mediated cell signaling as well as inhibit Th17 producing cells.

Recent evidence suggests that IL-23Rα gene may undergo extensive alternative mRNA splicing. There are at least twenty-four (24) potential gene transcripts for IL-23Rα. From these IL-23Rα alternatively spliced mRNA sequences, there appears at least four (4) deduced putative translated proteins: (1) a short premature IL-23Rα extracellular peptide; (2) a possible soluble form of IL-23Rα lacking a transmembrane/intracellular domain; (3) a full-length IL-23Rα with truncated extracellular region; and (4) a non-responsive membrane bound receptor isoform of IL-23Rα with deletion in intracellular signaling components.

Although many gene transcripts for IL-23Rα (i.e., IL-23Rα splice variants) are suggested, it is important to point out that their actual existence in vivo is presently unknown. There is little information regarding whether any of the deduced IL-23Rα translated products actually exist in vivo, let alone the function of these IL-23Rα protein variants, if any.

Accordingly, there is continuing need for a therapeutic agent that inhibits IL-23 cellular signaling and antagonizes Th17 cell maturation. The present inventors have discovered a naturally-occurring soluble form of IL-23Rα. This soluble form of IL-23Rα lacks the exon-9 or exons-8/9 of the IL-23Rα chain mRNA transcript (e.g., Δ9 and Δ8,9). The present application reveals that recombinant Δ9 and Δ8,9 proteins function to inhibit IL-23 cell signaling and blocks the differentiation of Th17 cells. The recombinant Δ9 and Δ8,9 as well as their protein variant forms of IL-23Rα have the utility application to treat inflammatory bowel diseases such as Crohn's disease.

SUMMARY OF THE INVENTION

In one aspect, the present invention provides isolated soluble recombinant IL-23Rα protein, wherein said recombinant protein has the following characteristics: a) lacking a transmembrane domain; b) existing as a monomer; and c) having the ability to inhibit IL-23R-mediated cell signaling.

In one aspect, the present invention provides an isolated soluble recombinant IL-23Rα protein that has the capability of inhibiting IL-23R-mediated cell signaling. An exemplary cell signaling event includes the formation of at least one transcriptional factor (phosphorylated) selected from the group consisting of STAT1, STAT2, STAT3, and STAT5. Preferably, the IL-23R-mediated cell signaling is the STAT3 formation.

In one aspect, the present invention provides an isolated soluble recombinant IL-23Rα protein that has the capability of inhibiting IL-23R-mediated cell signaling. An exemplary cell signaling includes the formation of IL17A or IL17F. Preferably, it is the IL17A formation (i.e., production or secretion).

In one aspect, the present invention provides an isolated soluble recombinant IL-23Rα protein that has the ability to inhibit Th17 cell maturation.

In one aspect, the isolated soluble recombinant IL-23Rα protein contains eight (8) amino acids of GLKEGSYC (SEQ ID NO: 9) (See, FIG. 3B). The eight (8) amino acid residues are present at the C-terminus of the soluble IL-23Rα protein. The GLKEGSYC sequence (SEQ ID NO: 9) is novel (i.e., not present in the native IL-23Rα protein), and occurs as a result of frameshift on exon 10 (due to exon 9 skipping or exons 8/9 skipping) (See, FIGS. 3B, 3C, and 3D). The unique GLKEGSYC sequence (SEQ ID NO: 9) is found present in both the Δ9 and Δ8, 9 proteins.

In one aspect, the isolated soluble recombinant IL-23Rα protein (Δ9) lacks five (5) amino acids (i.e., DNRGD, SEQ ID NO: 10) (See, FIG. 3B). The missing five (5) amino acid residues are located at the extracellular domain (i.e., C-terminal end of the extracellular domain), and in the proximity of the transmembrane domain.

In one aspect, the isolated soluble recombinant IL-23Rα protein (Δ8,9) lacks five (5) amino acids (i.e., DNRGD, SEQ ID NO: 10) and further lacks an extra thirty (30) amino acids (i.e., a total of thirty-five (35) amino acids) due to exon 8 and exon 9 skipping. The missing thirty five (35) amino acid residues locate at the extracellular domain (i.e., C-terminal end of the extracellular domain), and in the proximity of the transmembrane domain (See, FIG. 3E).

In another aspect, the soluble recombinant IL-23Rα has a total of 356 amino acid residues, after protein translation (See, FIG. 3B). However, when the IL-23Rα protein becomes mature (i.e., signal peptide is cleaved to form the mature protein), it has a total of 333 amino acid residues (because the signal peptide is a 23 amino acid residue long) (Δ9) (See, FIG. 3B).

The isolated soluble recombinant IL-23Rα (represents a mature protein) has an amino acid sequence set forth in SEQ ID NO: 2. The isolated soluble IL-23Rα protein is encoded by a cDNA having a nucleotide sequence set forth in SEQ ID NO: 1. The isolated soluble IL-23Rα protein (Δ9) (SEQ ID NO: 2) is derived from a human cell, and it may be a recombinant protein.

In another aspect, the isolated soluble recombinant IL-23Rα has an amino acid sequence set forth in SEQ ID NO: 4 (See, FIG. 3D). The isolated soluble IL-23Rα protein is encoded by a cDNA having a nucleotide sequence set forth in SEQ ID NO: 3 (See, FIG. 3D). The isolated soluble IL-23Rα protein (Δ8,9) (SEQ ID NO: 4) is derived from a human cell, and it may be a recombinant protein.

In one aspect, the present invention provides a pharmaceutical composition comprising an isolated soluble recombinant IL-23Rα protein and a pharmaceutical acceptable excipient.

In one aspect, the pharmaceutical composition comprises an isolated soluble IL-23Rα having an amino acid sequence set forth in SEQ ID NO: 2 or SEQ ID NO: 4. The protein may be a recombinant protein.

In one aspect, the present invention provides a method of preparing an isolated IL-23Rα protein, comprising the steps of: a) transfecting a cell with a gene encoding a protein that has an amino acid sequence set forth in SEQ ID NO: 2; b) allowing said transfected cell to produce a recombinant protein; and c) isolating said recombinant protein. The cDNA having a nucleotide sequence set forth in SEQ ID NO: 1. The transfected cell may be a mammalian cell. The recombinant protein has an amino acid sequence set forth in SEQ ID NO: 2.

In one aspect, the present invention provides a method of preparing an isolated IL-23Rα protein, comprising the steps of: a) transfecting a cell with a gene encoding a protein that has an amino acid sequence set forth in SEQ ID NO: 4; b) allowing said transfected cell to produce a recombinant protein; and c) isolating said recombinant protein. The cDNA having a nucleotide sequence set forth in SEQ ID NO: 3. The transfected cell may be a mammalian cell. The recombinant protein has an amino acid sequence set forth in SEQ ID NO: 4.

In one aspect, the present invention provides a method of inhibiting IL-23R-mediated cell signaling in a mammalian cell, comprising the steps of: a) exposing a mammalian cell to a recombinant IL-23Rα protein, wherein said recombinant protein has an amino acid sequence selected from the group consisting of SEQ ID NO: 2 and SEQ ID NO: 4. Preferably, the mammalian cell is a human cell.

In one aspect, the present invention provides a method of treating a human, comprising the steps of: a) identifying a human inflicted with an inflammatory bowel disease; b) administrating a pharmaceutical composition comprising an isolated recombinant IL-23Rα protein and a pharmaceutical acceptable excipient, The isolated protein contains an amino acid sequence of GLKEGSYC (SEQ ID NO: 9), and has an amino acid sequence set forth in SEQ ID NO: 2. In one aspect, the present invention provides an isolated soluble IL-23Rα protein, wherein said protein has the characteristics of: a) lacking a transmembrane domain; b) existing as a monomer; and c) having the ability to inhibit IL-23R-mediated cell signaling.

In one aspect, the present invention provides a method of treating a human, comprising the steps of: a) identifying a human inflicted with an inflammatory bowel disease; b) administrating a pharmaceutical composition comprising an isolated IL-23Rα protein and a pharmaceutical acceptable excipient, The isolated recombinant protein contains an amino acid sequence of GLKEGSYC (SEQ ID NO: 9), and has an amino acid sequence set forth in SEQ ID NO: 4. In one aspect, the present invention provides an isolated soluble IL-23Rα protein, wherein said protein has the characteristics of: a) lacking a transmembrane domain; b) existing as a monomer; and c) having the ability to inhibit IL-23R-mediated cell signaling.

In one aspect, the present invention provides a method of diagnosing a human subject suspected of suffering from Crohn's disease, comprising the steps of: (a) obtaining a biological sample from a human; (b) determining the level of a soluble IL-23Rα protein in said sample, wherein said soluble IL-23Rα protein (i) lacks a transmembrane domain; (ii) exists as a monomer; and (iii) has the ability to inhibit IL-23Rα-mediated cell signaling; and comparing said IL-23Rα level in said human to the level of said soluble IL-23Rα in an healthy individual, wherein an elevation in said level of said soluble IL-23Rα is indicative of the presence of Crohn's disease.

In one aspect, the present invention provides a method for detecting a soluble truncated IL-23Rα in a biological sample, comprising the steps of: a) obtaining a biological sample; b) incubating said biological sample with a capture reagent immobilized on a solid support to bind said truncated isoform of IL-23Rα, wherein the capture reagent comprises a first antibody that specifically binds IL-23Rα, and a second antibody that specifically binds to the human IL-23Rα; and (c) detecting IL-23Rα bound to said immobilized capture reagent by contacting the bound IL-23Rα with a detectable antibody that binds to human IL-23Rα.

Preferably, the first antibody is a monoclonal antibody, and the second antibody is a polyclonal antibody. Preferably, the first antibody recognizes and binds to a domain that corresponds to the amino acids 318-348. The application is also intended to cover equivalent antibody that recognizes and bind to a domain near the amino acids 318-348 of the C-terminus, and still possess the ability to function as a capture antibody.

The soluble truncated recombinant IL-23Rα lacks a transmembrane domain, and exists as a monomer. The soluble truncated IL-23Rα can inhibit IL-23-mediated cell signaling as well as Th17 cell differentiation. Preferably, the soluble truncated IL-23Rα has an amino acid sequence set forth in SEQ ID NO:2. Preferably, the soluble truncated IL-23Rα has an amino acid sequence set forth in SEQ ID NO: 4.

Preferably, the biological sample is selected from the group consisting of blood and plasma, wherein said biological sample comprising EDTA. More preferably, the biological sample is EDTA-treated plasma.

DESCRIPTION OF THE DRAWINGS

FIG. 2A depicts the gene organization (exon-intron relationship) of IL-23Rα and its Δ9 variant. Note that the Δ9 variant lacks the exon 9 which, inter alia, encodes the transmembrane domain. FIG. 2B depicts the protein domain organization between wild-type IL-23Rα and Δ9. Note that Δ9 protein contains an extra eight (8) amino acids (GLKEGSYC) due to the alternative translation reading frame used on exon 10. The eight (8) amino acids present on 19 are not present on the wild-type IL-23Rα protein, indicating that these amino acids are novel and specific for Δ9 protein.

FIG. 3A depicts the nucleotide sequence of the coding region for Δ9 (Top) as well as the amino acid sequence for the translated Δ9 protein (Below). FIG. 3B depicts the amino acid alignment between wild-type IL-23Rα and that of Δ9. FIG. 3D depicts the nucleotide sequence of the coding region for Δ8,9 (Top) as well as the amino acid sequence for the translated Δ8,9 protein (Below). FIG. 3E depicts the amino acid alignment between wild-type IL-23Rα and that of Δ8,9.

IL-23Rα level were 155.4 ng/mL and 144.5 ng/mL, respectively. Both mean and median in Crohn's patients were higher than that in the normal group. The difference between the two groups was statistically significant (p=0.00136).

Figure 16:
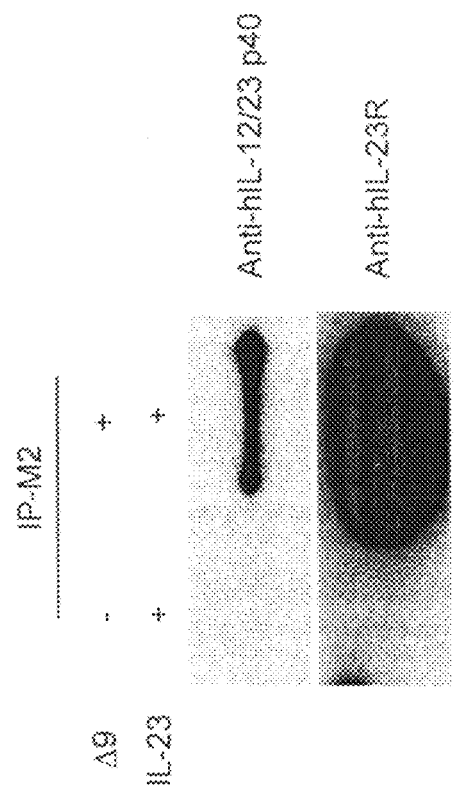

FIG. 16 depicts the in vitro binding assay to examine the binding of IL-23 to recombinant Δ9 protein. Immunoprecipitation experiment was performed using anti-Flag M2 affinity gel. Immunoblot experiment was performed to detect IL-23 and the recombinant Δ9 protein in the precipitates using anti-hIL-12/23 p40 and anti-hIL-23Rα respectively. IL-23 was detected only in the reaction containing the recombinant Δ9 protein.

Figure 17:
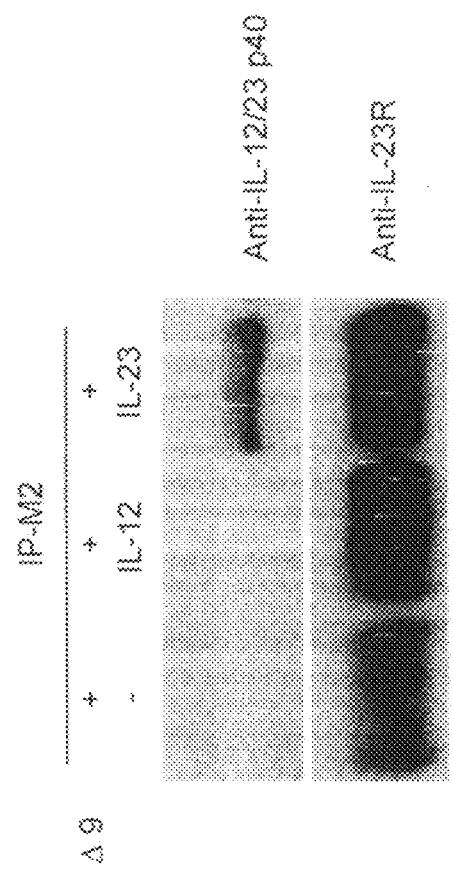

FIG. 17 depicts the binding specificity of the recombinant Δ9 protein. Immunoprecipitation experiments were performed using anti-Flag M2 affinity gel. Immunoblot experiment was performed to detect IL-12 and IL-23 in the precipitates using the anti-hIL-12/23 p40 (i.e., anti-human IL-12/23 p40). The recombinant Δ9 protein in the precipitates was detected by anti-human IL-23R. Only IL-23 but not IL-12 was detected in the reaction containing the recombinant Δ9 protein.

Figure 18:
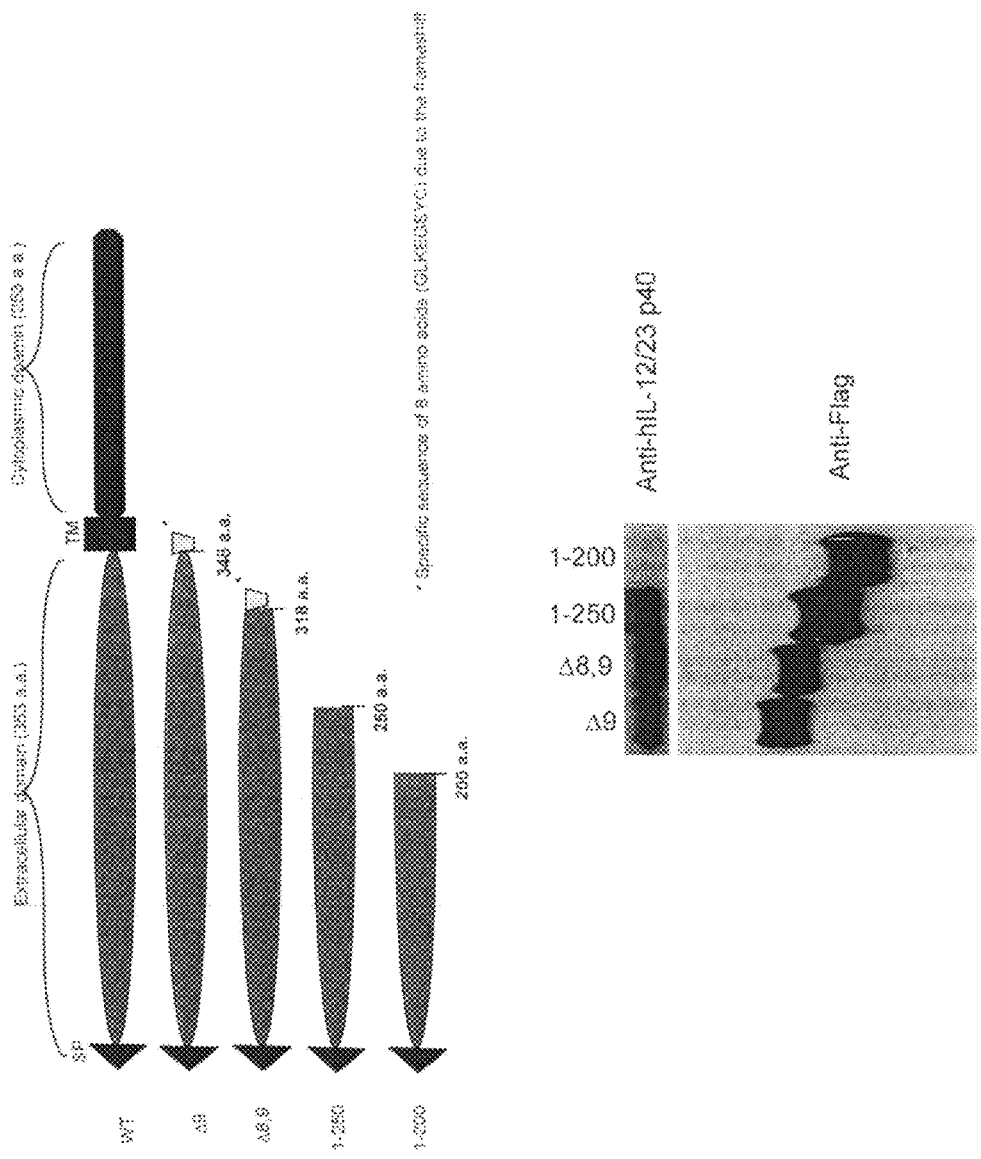

FIG. 18 depicts that the recombinant Δ9, Δ8,9 and 1-250 proteins bind to human IL-23 cytokine. These recombinant proteins were purified from the culture media of 293T cells transient transfected with the corresponding expression constructs. 200 ng of human IL-23 cytokine was added to the immunoprecipitation reaction. The presence of IL-23 in the precipitate was examined by immunoblot using anti-hIL-12/23 p40 antibody.

Figure 19:
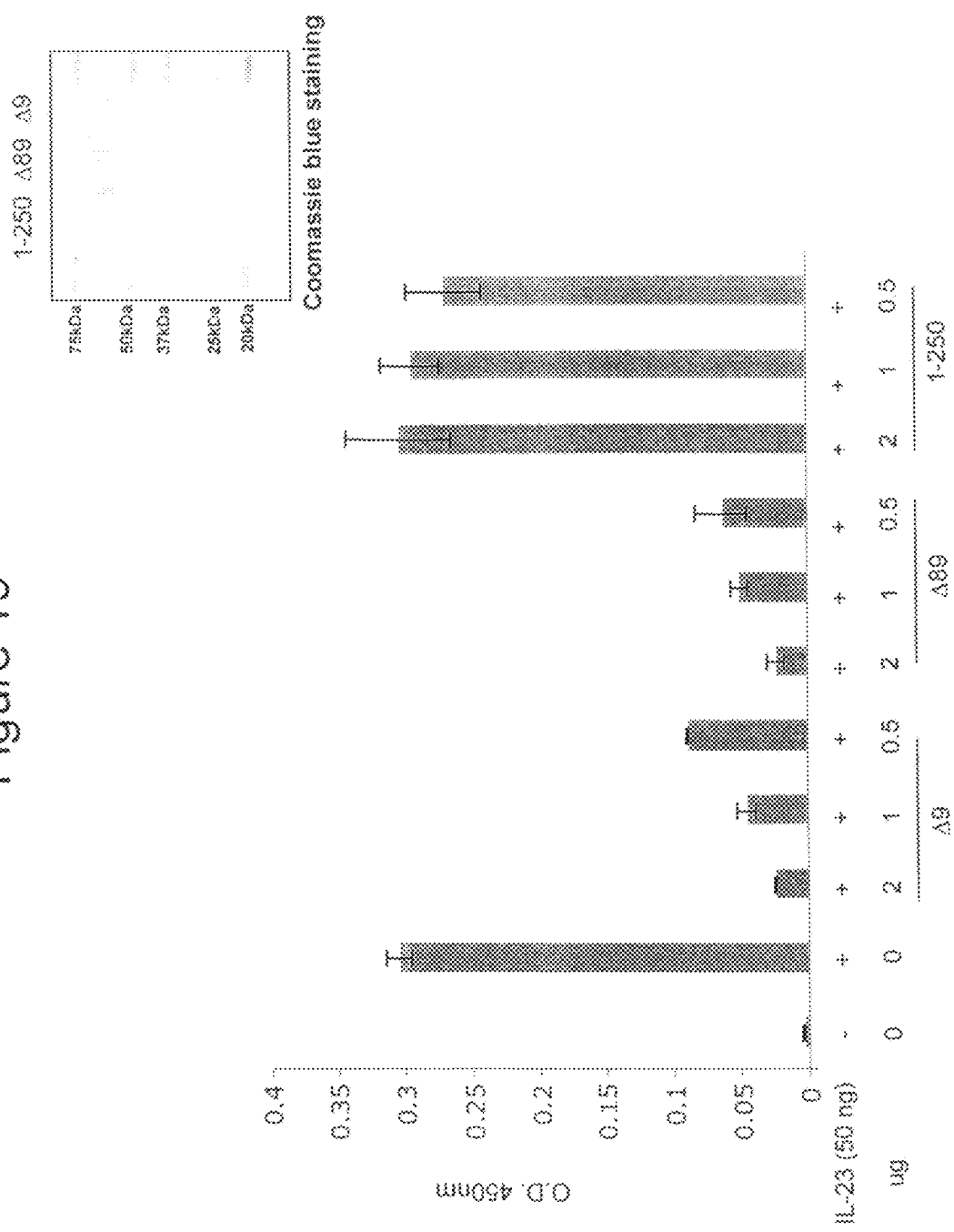

FIG. 19 depicts that the recombinant Δ9 and Δ8,9 proteins effectively compete with full-length extracellular domain of IL-23Rα protein to bind to IL-23 cytokine. The purity of these recombinant proteins was shown in the coomassie blue staining gel.

Figure 20:
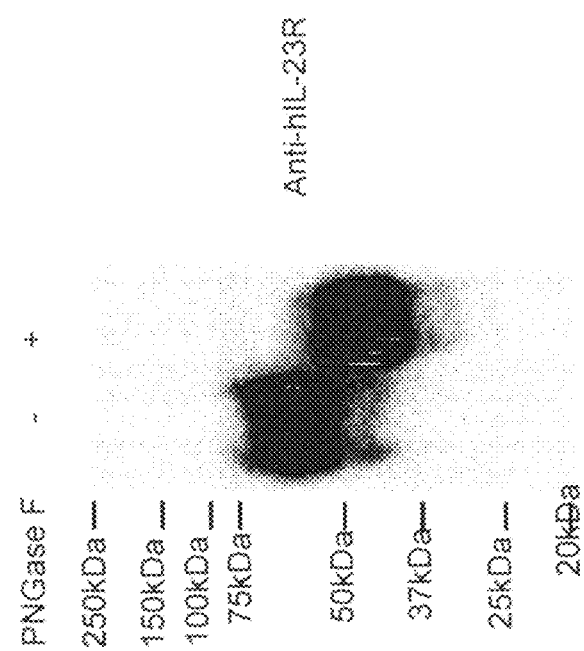

FIG. 20 depicts that the recombinant Δ9 protein is N-glycosylated. The purified Δ9 protein was treated with PNGase F. Immunoblot experiment was performed using mouse anti-hIL-23R. PNGase F treatment resulted in reduced size of purified Δ9 protein.

Figure 21:
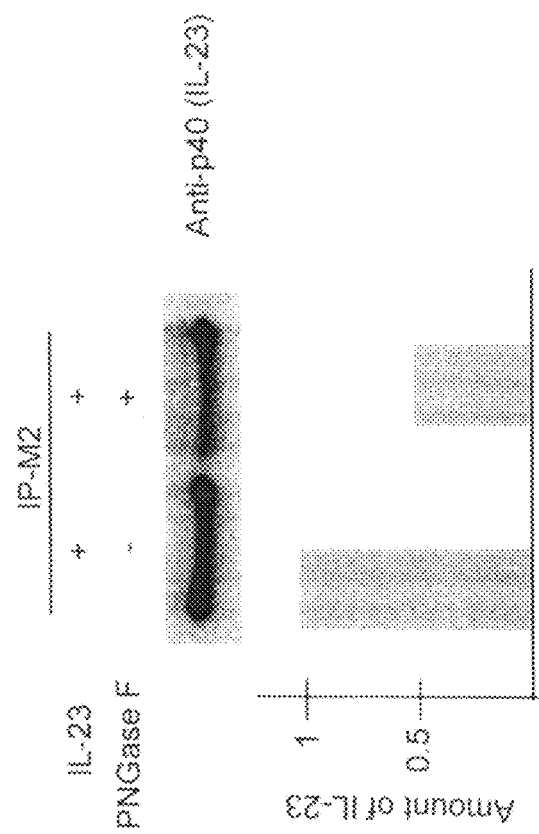

FIG. 21 depicts the importance of N-glycosylation on the recombinant Δ9 protein. In vitro binding assay was performed to examine the effect of N-glycosylation of the recombinant Δ9 protein on IL-23 binding. Immunoprecipitation experiment was performed using anti-Flag M2 affinity gel. Immunoblot experiment was performed to detect IL-23 in the precipitates using anti-hIL-12/23 p40. Removal of N-glycosylation on the recombinant Δ9 protein reduced its binding to IL-23.

Figure 22:
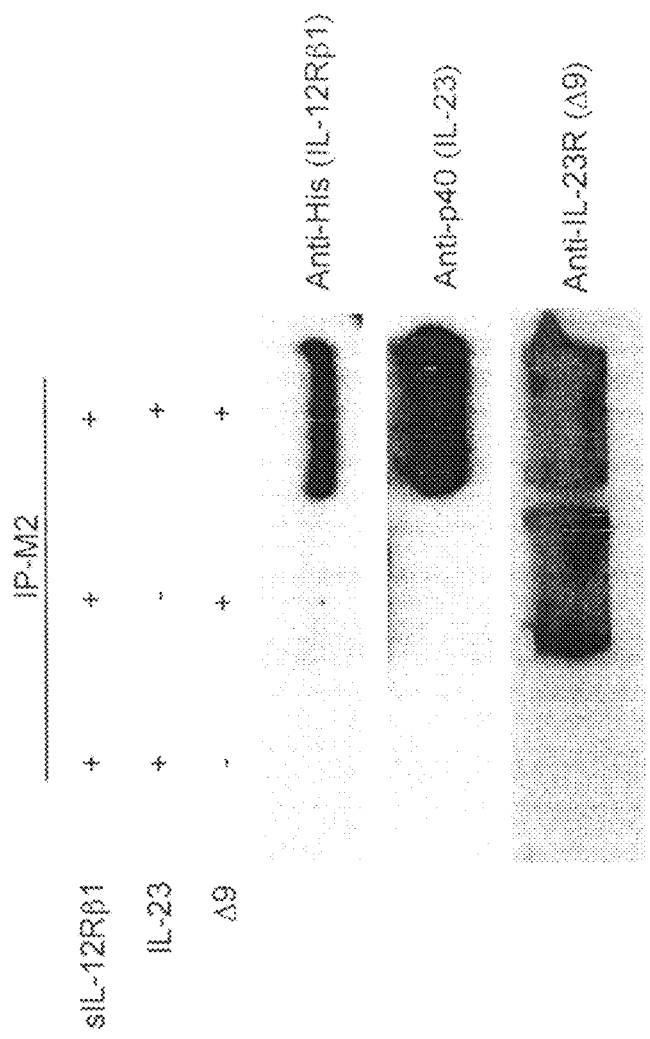

FIG. 22 depicts the in vitro binding assay to examine the binding of the recombinant Δ9 protein to IL-12Rβ1. Recombinant human His-tagged sIL-12Rβ1 (i.e., soluble IL-12Rβ1) was spiked into the suspension containing Δ9 bound to anti-Flag M2 affinity gel, in the presence or absence of 200 ng IL-23. The eluted product was analyzed in the immunoblot using anti-His, anti-hIL-12/23 p40 or mouse anti-IL-23R to detect sIL-12Rβ1, the p40 subunit of IL-23 or Δ9, respectively. Δ9 only co-precipitates sIL-12Rβ1 in the presence of IL-23.

Figure 23:
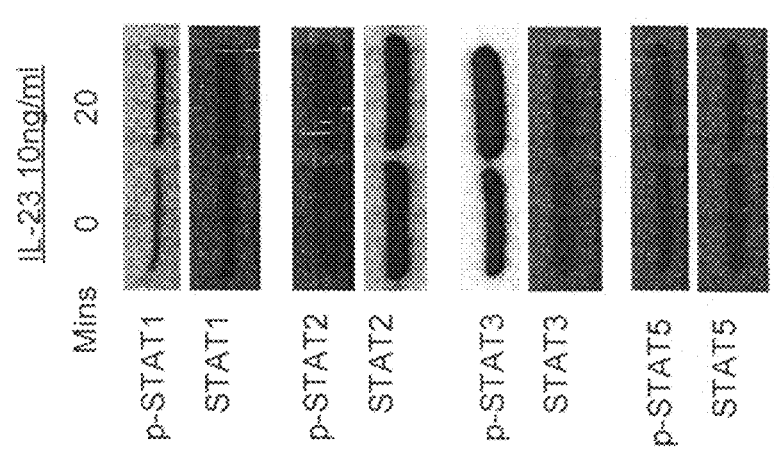

FIG. 23 depicts the activation of STAT3 by IL-23 in the human leukocytes. Human leukocytes were stimulated with 10 ng/mL IL-23 for 20 mins. Cell lysates were prepared for immunoblots to examine phosphorylation status of STATs. Membranes were first probed with antibodies against p-STATs, then stripped and re-probed for total STATs. IL-23 strongly activated STAT3.

Figure 24:
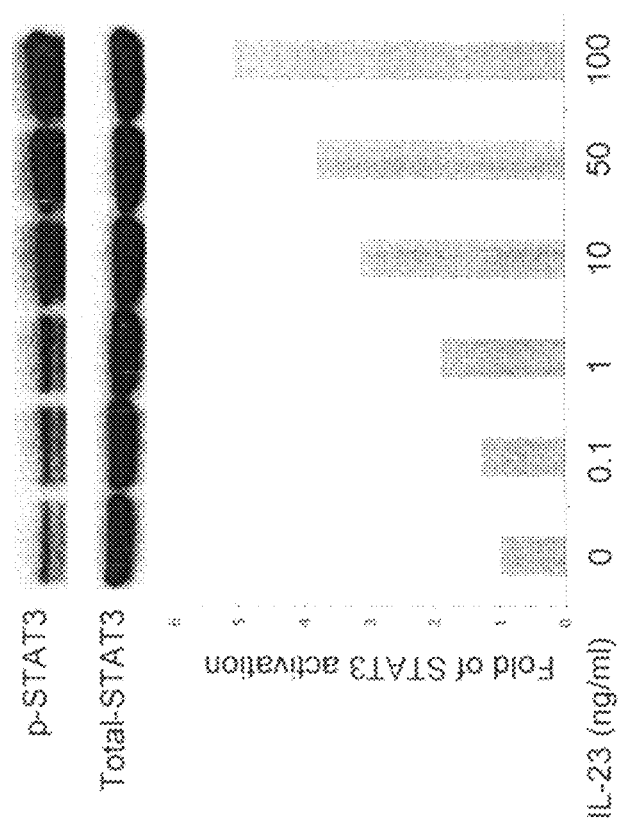

FIG. 24 depicts the dose response of STAT3 activation upon IL-23 stimulation. Human leukocytes were stimulated with different amounts of IL-23 (from 0 to 100 ng/mL) for 20 minutes. p-STAT3 immunoblot was used to measure STAT3 activation. Fold of STAT3 activation is illustrated in the bar chart. STAT3 activation in the human leukocytes showed the dose-dependent response toward IL-23.

Figure 25:
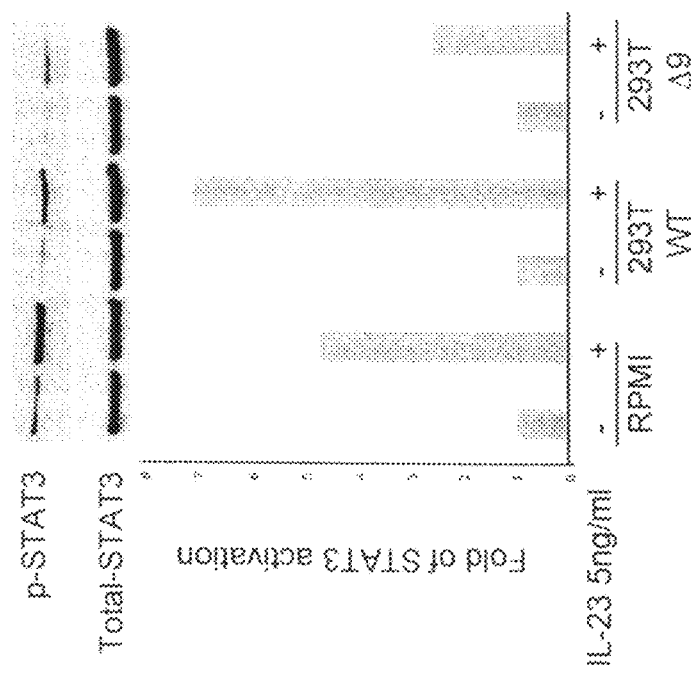

FIG. 25 depicts that the culture medium containing the recombinant Δ9 protein blocks STAT3 activation by IL-23. Human leukocytes were cultured in RPMI medium or culture media from the 293T cells transfected with either wild-type IL-23Rα or Δ9 expression plasmids. Cells were then stimulated with 5 ng/mL IL-23 for 20 minutes. STAT3 activation was measured by p-STAT3 immunoblot. Fold of STAT3 activation was illustrated in the bar chart. Activation of STAT3 was found in the human leukocytes cultured with RPMI and cultured medium from 293T cell transfected with the wild-type IL-23Rα expression plasmid. STAT3 activation was diminished when the human leukocytes were cultured in the Δ9 containing medium.

Figure 26:
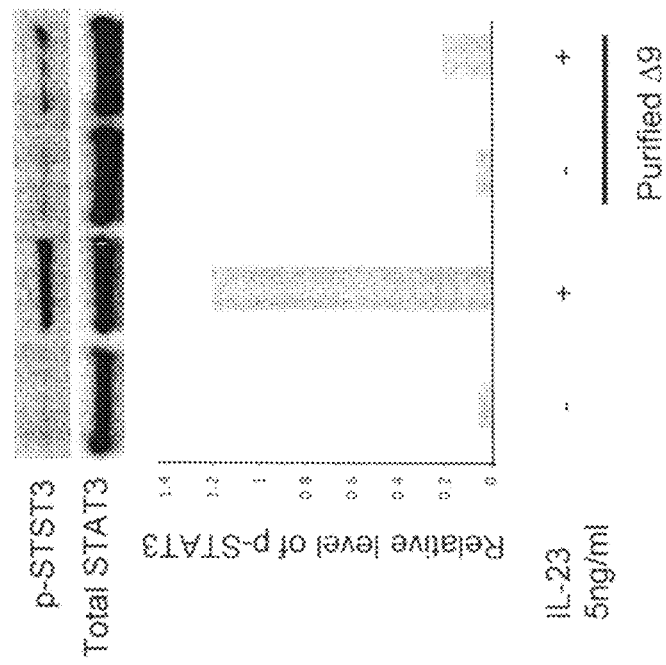

FIG. 26 depicts the inhibition of purified Δ9 protein on STAT3 activation induced by IL-23 in the human leukocytes. The human leukocytes were cultured in the RPMI medium and stimulated with 5 ng/mL IL-23 in the presence or absence of the purified recombinant Δ9 protein (500 ng/mL). Immunoblots were performed using p-STAT3 and total-STAT3 antibodies. Relative level of p-STAT3 was illustrated in the bar chart. Purified recombinant Δ9 protein significantly inhibited the STAT3 activation upon IL-23 stimulation.

Figure 27:
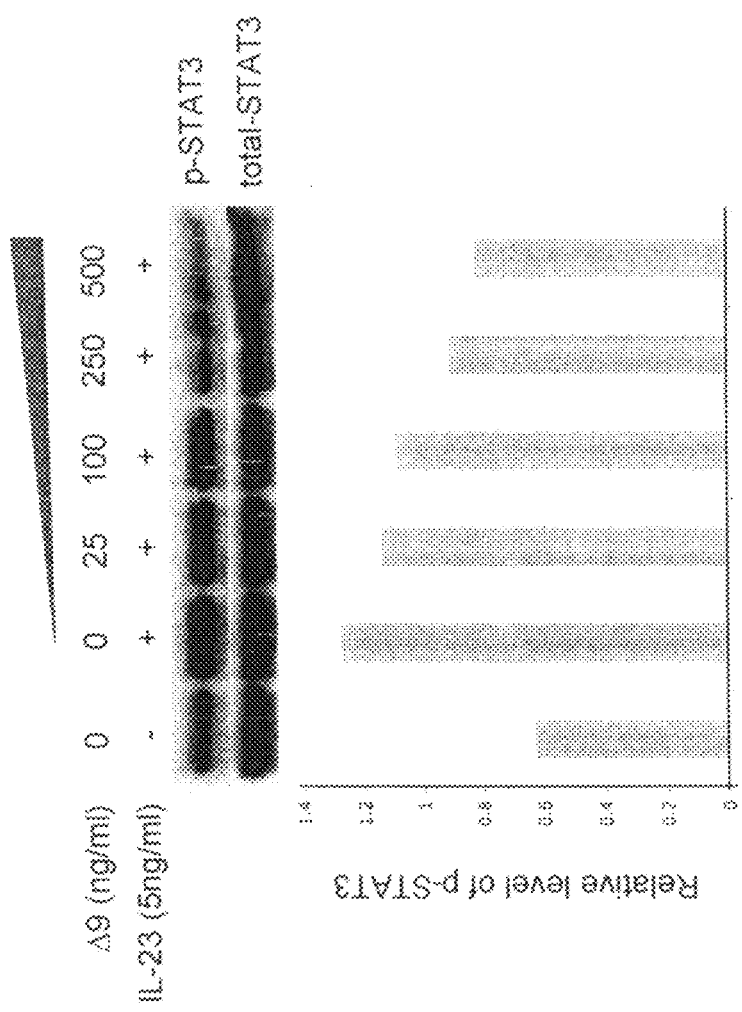

FIG. 27 depicts the dose response of the inhibition of IL-23R signaling by purified recombinant Δ9 protein. Different amounts of Δ9 protein (from 0 to 500 ng/mL) were added to the human leukocytes stimulated with 5 ng/mL IL-23. Immunoblots were performed using p-STAT3 and total-STAT3 antibodies. Relative level of p-STAT3 was illustrated in the bar chart.

Figure 28:
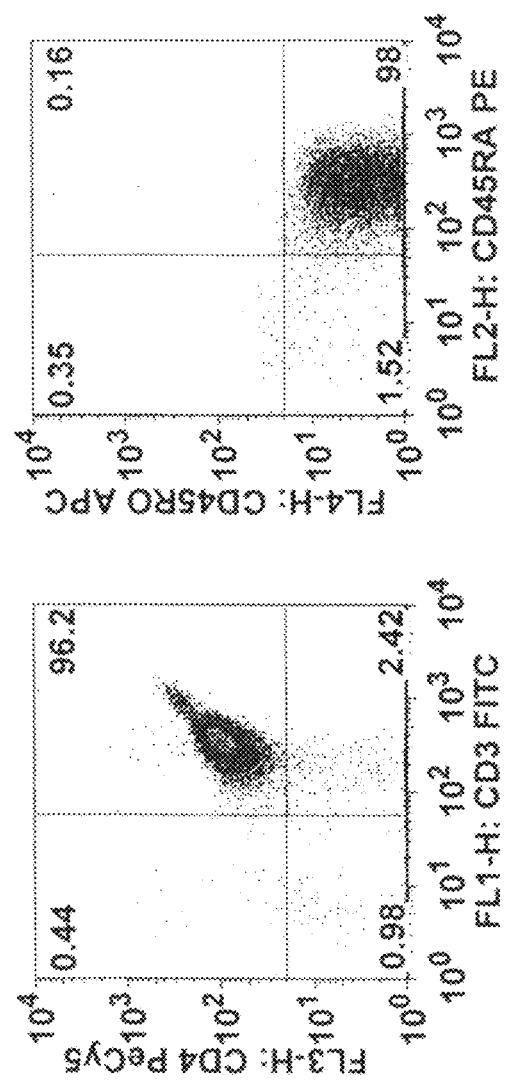

FIG. 28 depicts the purity of isolated $CD4^+$ naïve T cells from human leukocytes measured by the Flow Cytometry. Around 96% of the population was CD4+ T cells. 98% of population showed positive staining of CD45RA and negative staining of CD45RO, which is the characteristic of $CD4^+$ naïve T cells.

Figure 29:
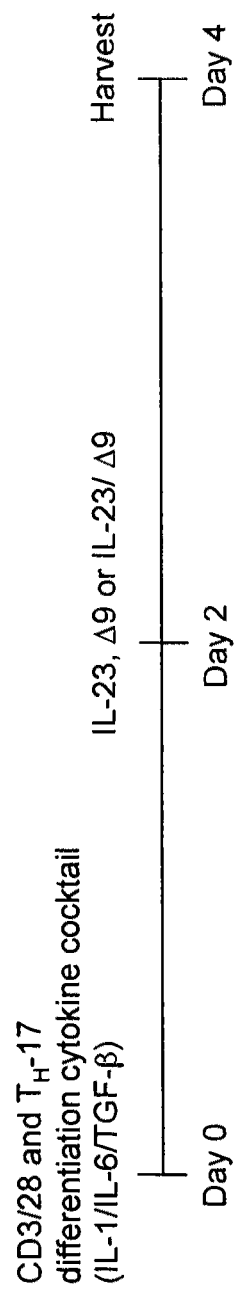

FIG. 29 depicts the in vitro Th17 differentiation protocol using $CD4^+$ naïve T cells. The isolated T cells were cultured for 5 days under the influence of CD3/28 and Th17 differentiation cytokine cocktail (10 ng/mL IL-1, 10 ng/mL IL-6 and 1 ng/mL TGF-β) in the presence of 5 ng/mL IL-23, 500 ng/mL purified Δ9 protein or IL-23/Δ9 complex. Both mRNA and culture media were collected.

Figure 30:
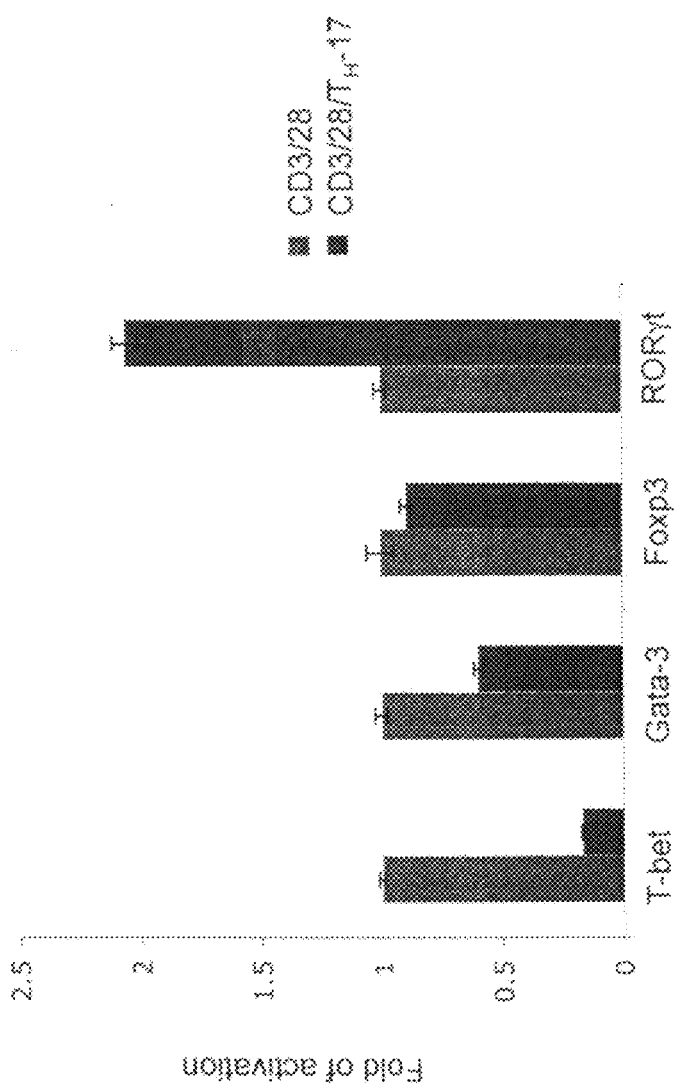

FIG. 30 depicts the changes of mRNA transcript levels of transcriptional factors (i.e., T-bet (Th1), GATA-3 (Th2), Foxp3 (Treg), and RORγt (Th17)) during the differentiation of $CD4^+$ naïve T cells into Th17 cells. Two fold increase of RORγt mRNA expression was found in the in vitro differentiated Th17 cells. However, no up-regulation was observed in the other T cell transcriptional factors.

Figure 31:
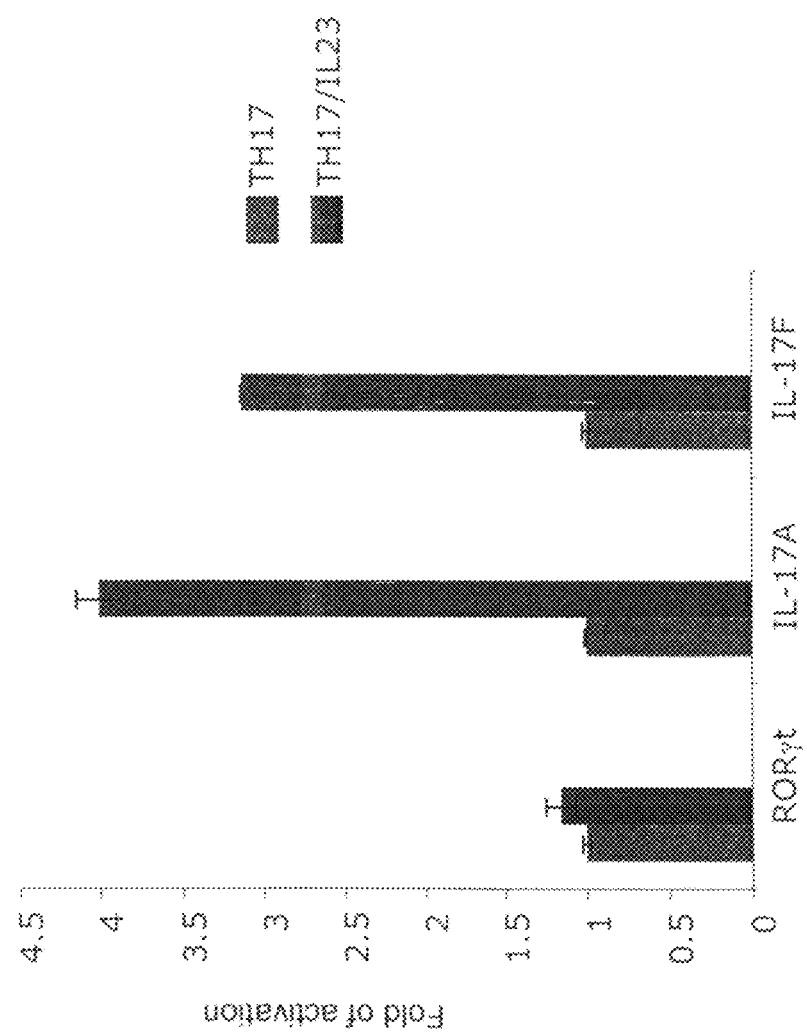

FIG. 31 depicts the ability of IL-23 to enhance the expression of IL-17A and IL-17F during the differentiation of $CD4^+$ naïve T cells into Th17 cells. IL-23 showed no effect on the RORγt mRNA expression.

Figure 32:
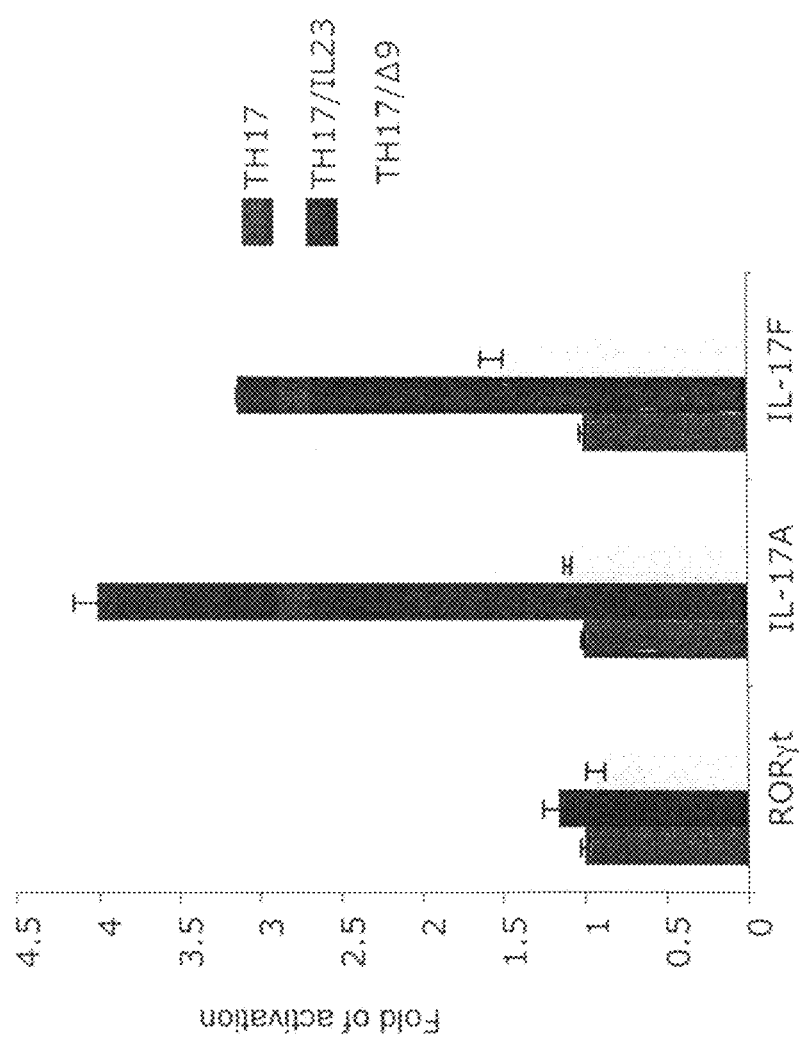

FIG. 32 depicts the inability for Δ9 to enhance the expression of IL-17A and IL-17F during the differentiation of $CD4^+$ naïve T cells into Th17 cells.

Figure 33:
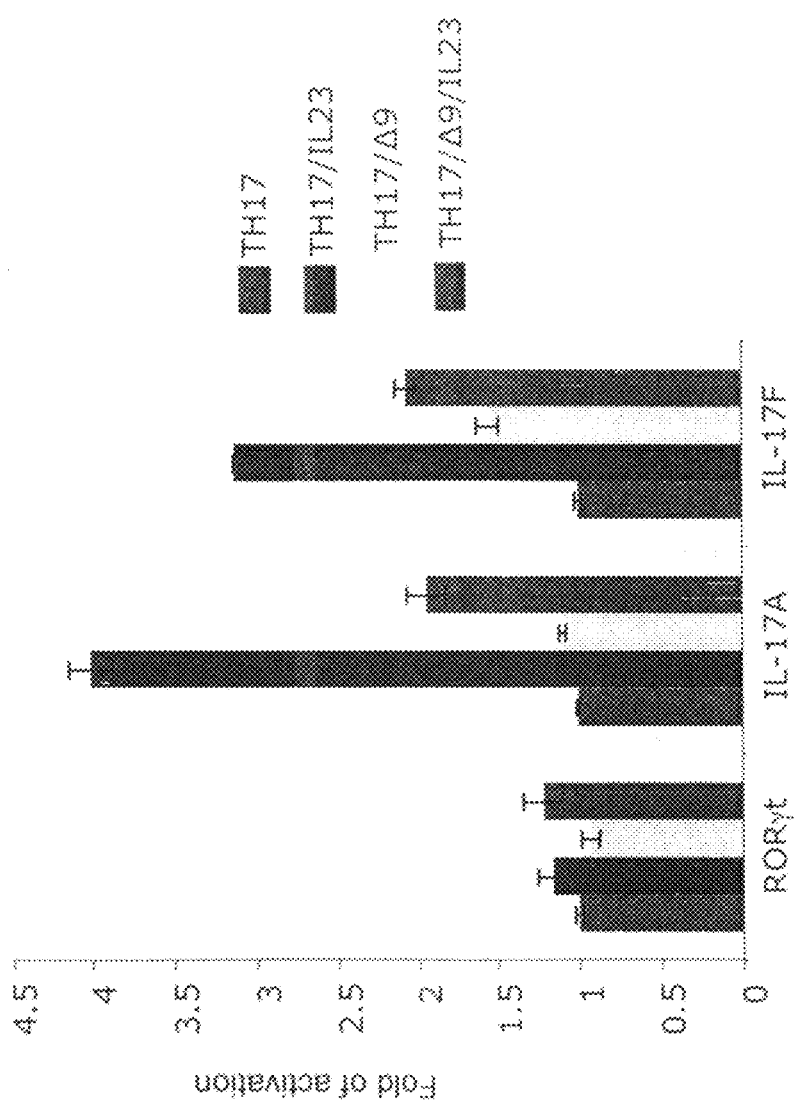

FIG. 33 depicts the ability of Δ9 to block the effect of IL-23 in enhancing the expression of IL-17A and IL-17F during the differentiation of $CD4^+$ naïve T cells into Th17 cells.

Figure 34:
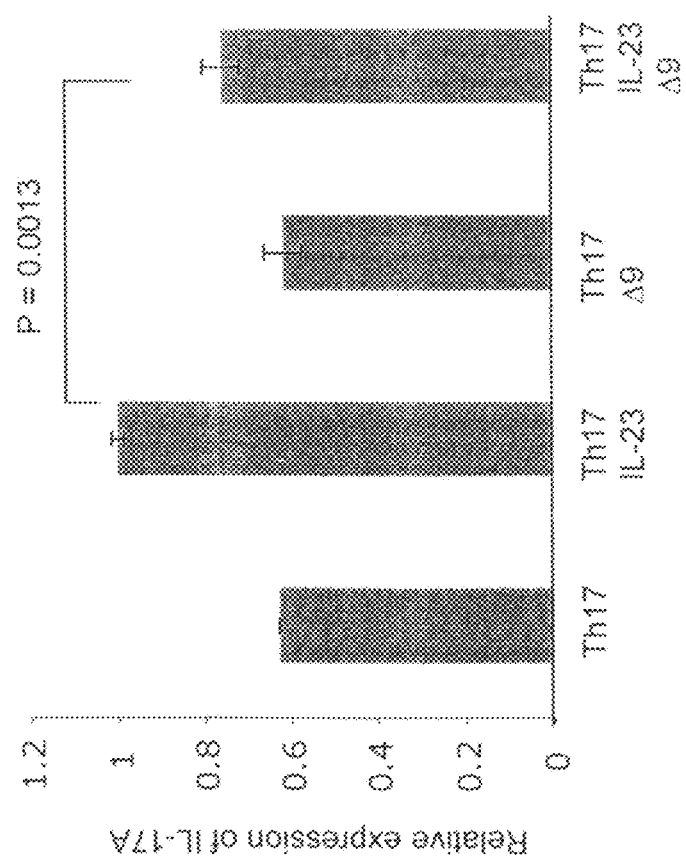

FIG. 34 depicts an ELISA experiment to measure the IL-17A production in the in vitro differentiated Th17 under four (4) different conditions.

Figure 35:
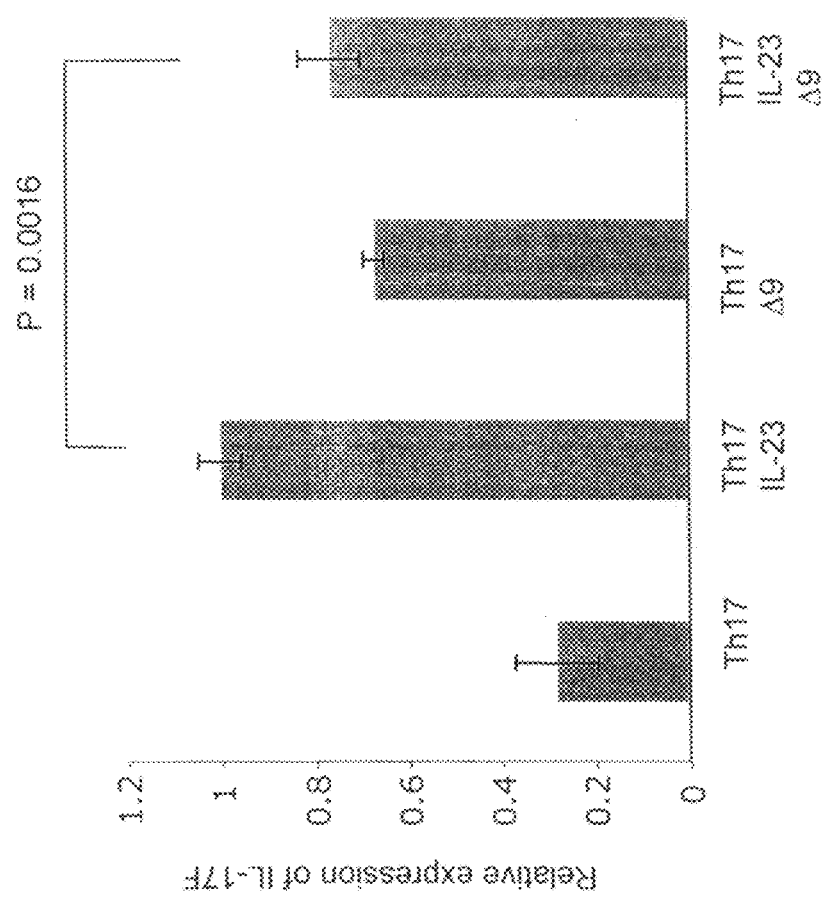

FIG. 35 depicts an ELISA experiment to measure the IL-17F production in the in vitro differentiated Th17 under four (4) different conditions.

DETAILED DESCRIPTION OF THE INVENTION

Definitions

The following definitions are used for this application:

The term "IL-23R" refers to interleukin-23 receptor. IL-23R is composed of two (2) subunits: IL-23Rα and IL-12Rβ1. The IL-23Rα gene is located on chromosome 1p31.3. The native form of human IL-23Rα mRNA is 2.8 kb long and contains 11 exons (NM_144701). The transcribed mRNA is translated into a full-length protein of 629 amino acids, the sequence of which is listed in NM_144701. The full-length translated IL-23Rα protein is a type I cytokine receptor and forms with human IL-12Rβ1 to form the heterodimeric IL-23 receptor. Human IL-12Rβ1 also partners with human IL-12Rβ2 to form the cell-surface IL-12 receptor. When bound to IL-23, this protein triggers a series of cell signaling event including activation of Janus kinase 2 (JAK2), and transcription activator STAT3 (i.e., IL-23R mediated cell signaling). IL-23R is present on many immune system cells, including T cells, natural killer (NK) cells, monocytes, and dendritic cells.

The term "soluble IL-23Rα" refers to an IL-23Rα that lacks a transmembrane domain (i.e., contains extracellular domain that encompasses 1-353 amino acid residues of the full-length translated IL-23Rα protein) and thus become soluble in an aqueous medium. A soluble IL-23Rα may be present as monomer or form a homodimer (as is the case for the chimeric molecule where human Fc (from an IgG1 molecule) that is fused with two (2) IL-23Rα molecules. For purposes of this application, the term "soluble IL-23Rα" includes the naturally-occurring truncated IL-23Rα as a result of alternative gene splicing. In particular, it includes Δ9 protein having an amino acid sequence set forth in SEQ ID NO: 2. Also, it includes Δ8,9 protein having an amino acid sequence set forth in SEQ ID NO: 4.

For purposes of this application, the term "Δ9" refers to the naturally-occurring truncated IL-23Rα resulting from IL-23Rα gene splicing. The Δ9 protein has 348 amino acids plus eight (8) novel amino acid sequences unique to Δ9 protein (i.e., a total of 356 amino acids). Amino acid sequence comparison between Δ9 and wild-type IL-23Rα (extracellular domain; 353 amino acids) is provided in FIG. 3B. The signal sequence (i.e., 1-23 amino acids) on the immature Δ9 protein (located inside the cells) is cleaved before the mature Δ9 protein is released outside of the cells. The mature Δ9 therefore has a total of 333 amino acids (i.e., 24-356). For purposes of this application, therefore, the term "Δ9" is intended to include Δ9 forms with or without the signal sequence (i.e., immature and mature Δ9 proteins).

For purposes of this applications, the term "Δ8,9" refers to the naturally-occurring truncated IL-23Rα resulting from IL-23Rα gene splicing. The Δ8,9 protein has 318 amino acids plus eight (8) novel amino acid sequence unique to Δ8,9 (a total of 326 amino acids). Amino acid sequence comparison between Δ8,9 and wild-type IL-23Rα (extracellular domain; 353 amino acids) is provided in FIG. 3E. The signal sequence (i.e., 1-23 amino acids) on the Δ8,9 is cleaved before the mature Δ8,9 protein is released. Therefore, the mature Δ8,9 has a total of 303 amino acids (i.e., 24-326). For purposes of this application, the term "Δ8,9" is intended to include Δ8,9 forms with or without the signal sequence (i.e., immature and mature Δ8,9 proteins).

The term "detecting" refers to quantitative measurements of IL-23Rα in a biological sample.

The term "biological sample" refers to a body sample from a mammal, preferably from a human. Biological sample may be obtained from patients inflicted with autoimmune diseases. Biological samples include biological fluids such as serum, plasma, lymph fluid, synovial fluid, amniotic fluid, urine, cerebrospinal fluid, saliva, tissue culture medium, tissue extracts and the like. The preferred biological sample is serum or plasma.

The term "mammal" refers to any animal classified as a mammal, including humans, and animals. Preferably, the mammal is human.

The term "autoimmune disease" refers to a pathological condition in mammals that is typically characterized by an unregulated immune cell activity. Examples of autoimmune include but are not limited to, inflammatory bowel disease, Crohn's disease, asthma and the like. Preferably, the autoimmune diseases are characterized by an increased Th17 activity. The present invention provides an isolated soluble IL-23Rα protein useful for treating inflammatory bowel diseases, such as Crohn's disease. The present invention also provides a composition and method for treating inflammatory bowel diseases.

The term "inflammatory bowel disease" means an inflammatory disease in bowel that involves Th17 cells. Crohn's disease represents an exemplary inflammatory bowel disease.

The term "effective amount" refers to an amount of soluble IL-23Rα sufficient to ameliorate a symptom of a pathological disease (such as Crohn's disease).

The present inventors discovered a hitherto unknown soluble form of a human IL-23Rα receptor (e.g., Δ9 and Δ8,9). Both the Δ9 and Δ8,9 mRNAs are a result of alternative splicing of the IL-23Rα gene that encodes the native IL-23Rα protein. The splice variant Δ9 is missing the exon 9 and does not contain a transmembrane domain and an intracellular domain. In Δ9, Exon 8 joins to Exon 10 and results in the shift of open reading frame and hence generates the novel eight (8) amino acid sequences (i.e., GLKEG-SYC, SEQ ID NO: 9). The splice variant Δ8,9 is missing exon 8 and exon 9 and also does not contain a transmembrane domain and an intracellular domain. Δ8,9 also contains the novel eight (8) amino acids of GLKEGSYC (SEQ ID NO: 9). Δ9 mRNA represents up to 20% of human leukocyte IL-23Rα transcript and thus is a major form of IL-23Rα mRNA. Δ8,9 mRNA also is detectable in the Fragment Analysis studies. The Δ9 form of IL-23Rα is secreted as a soluble monomer form and binds to IL-23 in solution. The present inventors further discovered that this soluble IL-23Rα form is capable of blocking IL-23 induced STAT3 phosphorylation and Th17 maturation.

In one embodiment, the present invention provides an isolated truncated IL-23Rα protein that can be used as an inhibitor of IL-23 cell signaling, in particularly in the context of inflammatory bowel diseases.

It is known that the native form of human IL-23Rα mRNA is 2.8 kb long, with 11 exons (NM_144701). This mRNA is translated into a type-I transmembrane protein of 629 amino acids. The native human IL-23Rα protein comprises an extracellular domain that contains 353-residue extracellular domain that includes a signal peptide, an N-terminal fibronectin-III-like domain, as well as a 253-residue cytoplasmic domain with three potential tyrosine phosphorylation sites. Genetic studies have suggested an association the IL-23Rα locus with protection/susceptibility in autoimmune inflammatory disorders, although the exact mechanistic basis remains elusive.

The present inventors have unexpectedly discovered a novel soluble truncated IL-23Rα. The present invention extends our previous findings that IL-23Rα mRNA undergoes extensive alternative splicing—resulting in twenty-four (24) different potential transcripts. Four different classes of putative translation products could be deduced from these alternatively spliced mRNA sequences: (i) short premature IL-23Rα extracellular peptides; (ii) soluble forms of IL-23Rα lacking transmembrane/intracellular domains; (iii) full-length IL-23Rα with a truncated extracellular region; and (iv) a membrane bound receptor isoform of IL-23Rα that lacked likely intracellular signaling components.

Using Fragment Analysis, the present inventors surprisingly discovered that there are six (6) alternative mRNA splice forms in human leukocytes. One of the forms (i.e., Δ9) represents the majority alternative mRNA splice form. Δ9 is found to be soluble and exists as monomer, and it has the ability to bind IL-23 and inhibit the generation of functional human Th-17 cells in vitro. Different from that of the native IL-23Rα protein, the present soluble truncated IL-23Rα lacks a transmembrane domain and contains 356 amino acids. Another form (i.e., Δ8,9) also share the common features as Δ9 (e.g., soluble monomer and ability to block IL-23R mediated cell signaling).

According to the present invention, a soluble truncated IL-23Rα form (i.e., Δ9 protein) contains a unique eight (8) amino acid sequence (GLKEGSYC, SEQ ID NO: 9) at its C-terminus, due to the exon 8 and exon 9 skipping. When analyzed under conditions of a reducing gel electrophoresis, the molecular weight of the protein is approximately ~60 kDa. The soluble truncated IL-23Rα protein (Δ9) corresponds to the N-terminal fragment of IL-23Rα lacking the transmembrane domain and has 356 amino acids (with 348 amino acids correspond to that of the native IL-23Rα, plus the eight (8) unique amino acid sequence of SEQ ID NO: 9)). The amino acid sequence of this particular soluble truncated IL-23Rα (i.e., Δ9 protein) is set forth in SEQ ID NO: 2.

According to the present invention, another soluble truncated IL-23Rα (i.e., Δ8,9 protein) also contains a unique eight (8) amino acid sequence (GLKEGSYC, SEQ ID NO: 9) at its C-terminus due to the alternative translation reading frame on exon 10. When analyzed under conditions of a reducing gel electrophoresis, the molecular weight of the protein is approximately ~60 kDa. The soluble truncated IL-23Rα protein corresponds to the N-terminal fragment of IL-23Rα lacking the transmembrane domain and has 326 amino acids (with 318 amino acids correspond to that of the native IL-23Rα plus the eight (8) unique amino acid sequence of SEQ ID NO: 9). The amino acid sequence of the soluble truncated IL-23Rα (i.e., Δ8,9 protein) is set forth in SEQ ID NO: 4.

In one embodiment, the present invention provides an isolated IL-23Rα protein that includes the protein selected from any of the following protein, an isolated protein of a truncated human IL-23Rα capable of inhibiting IL-23-mediated cell signaling; a recombinantly produced truncated human IL-23Rα; or a purified recombinant human truncated IL-23Rα having the amino acid sequence set forth in SEQ ID NO: 2 and SEQ ID NO: 4.

The soluble truncated IL-23Rα exists as a monomer and contains a unique eight (8) amino acid sequence. In one embodiment, the soluble IL-23Rα is detected in cultured media and can be recombinantly produced. The isolated truncated IL-23Rα protein has therapeutic value to alleviate inflammatory bowel diseases including Crohn's disease.

In a preferred embodiment, the present invention provides a recombinant soluble IL-23Rα, which has the amino acid sequence set forth in SEQ ID NO: 2 and SEQ ID NO: 4.

The present invention provides an isolated nucleic acid molecule encoding a truncated human IL-23Rα protein lacking a transmembrane domain. In one embodiment, the isolated nucleic acid molecule is a DNA molecule, preferably the isolated DNA is genomic DNA. In another embodiment, the isolated DNA molecule is a cDNA molecule. In one embodiment, the isolated nucleic acid molecule is an RNA molecule. In an embodiment, the isolated nucleic acid molecule encodes a human IL-23Rα having an amino acid sequence set forth in SEQ ID NO: 2, wherein the nucleotide sequence of the isolated DNA molecule is set forth in SEQ ID NO: 1. In an embodiment, the isolated nucleic acid molecule encodes a human IL-23Rα having an amino acid sequence set forth in SEQ ID NO: 4, wherein the nucleotide sequence of the isolated DNA molecule is set forth in SEQ ID NO: 3.

The present invention provides a recombinantly produced human IL-23Rα lacking a transmembrane domain. The present invention provides a purified recombinant human truncated IL-23Rα having the amino acid sequence set forth in SEQ ID NO: 2 or SEQ ID NO: 4.

In one embodiment, the present invention provides the expression of the DNA sequences disclosed herein. As is well known in the art, DNA sequences may be recombinantly expressed by operatively linking the sequences to an expression control sequence in an appropriate expression vector; and expressing that linked vector via transformation in an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and Synthetic DNA sequences. Suitable vectors include pcDNA 3.3.Topo, pcDNA 3.1, pCI, pSI, pTARhET, pPMR, pTK-Hyg and the like.

In one embodiment, a host cell contains the vector comprising the polynucleotides of the present invention. Exemplary host cell includes mammalian cells. Various cells strains include, for example, 293T, CHO, COS and the like.

It will be understood that not all vectors, expression control sequences and hosts will function equally well to express the IL-23Rα cDNA sequences of this invention. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, as well as the toxicity to the host of the product encoded by the DNA sequences to be expressed, and the ease of purification of the expression products. Considering these and other factors, a person skilled in the art will be able to construct a variety of vector/expression control sequence/host combinations that will express the DNA sequences of this invention in large scale animal culture.

For recombinant expression of the various proteins used in this application, genes encoding the various proteins of interest can be conveniently inserted into a cloning vector and the vector containing the gene of interest is transfected into a suitable host cell for protein expression. Various publicly available vectors may be used. For example, vectors may include a plasmid, cosmid, viral particle, or phage. Examples of vectors included pcDNA 3.3.Topo, pcDNA 3.1, pCI, pSI, pTARhET, pPMR, pTK-Hyg and the like. Vector components generally include, but are not limited to, an origin of replication, a selectable marker gene, an enhancer element, a promoter, and a transcription termination sequence and a poly-$A^+$ signal. Construction of suitable vectors containing one or more of these components as well as the gene of interest employs standard ligation techniques which are known to the skilled artisan.

Expression and cloning vectors will typically contain a selection gene, also termed a selectable marker. Typical selection genes encode proteins that confer resistance to antibiotics, e.g., ampicillin, neomycin, methotrexate, or tetracycline and puromycin.

Examples of suitable selectable markers for mammalian cells include those that enable the identification of cells competent to take up the antigen-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980).

A number of promoters can be used in order to enhance the expression of the gene of interest. In one embodiment, a promoter can be employed which will direct expression of a polynucleotide of the present invention in 293T cells. Other equivalent transcription promoters from various sources are known to those of skill in the art. Exemplary promoters include SV40 early, CMV, HSV TK, EF-1a and the like.

A promoter may be operably linked to the protein-encoding nucleic acid sequence to direct mRNA synthesis. Promoters recognized by a variety of potential host cells are well known.

Transcription of a DNA encoding the gene of interest by higher eukaryotes may be increased by inserting an enhancer sequence into the vector. Enhancers are cis-acting elements of DNA, usually about from 10 to 300 basepairs, that can act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the 15-kDa coding sequence, but is preferably located at a site 5' from the promoter.

Expression vectors used in mammalian cells will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Δ9 protein.

The nucleic acid (e.g., cDNA or genomic DNA) encoding recombinant Δ9 or Δ8, 9 of the present invention may be inserted into a replicable vector for cloning (amplification of the DNA) or for expression. For example, DNA encoding Δ9 (e.g., SEQ ID NO: 1) or Δ8, 9 (e.g., SEQ ID NO: 3), such as full-length Δ9 protein (SEQ ID No.2) or Δ8, 9 protein (SEQ ID No. 4) may be inserted into a replicable vector for cloning and for expression of full-length Δ9 or Δ8, 9 protein or fragments thereof. The appropriate nucleic acid sequence may be inserted into the vector by a variety of procedures. In general, DNA is inserted into an appropriate restriction endonuclease site(s) using techniques known in the art.

Host cells are transfected with expression or cloning vectors described herein for protein production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991).

Methods of eukaryotic cell transfection transformation are known to the ordinarily skilled artisan, for example, $CaCl_2$, $Ca_2PO_4$, liposome-mediated and electroporation. Depending on the host cell used, transformation is performed using standard techniques appropriate to such cells. The calcium treatment employing calcium chloride, as described in Sambrook et al., or electroporation is generally used for prokaryotes. For mammalian cells without such cell walls, the calcium phosphate precipitation method of Graham and van der Eb, *Virology*, 52:456-457 (1978) can be employed. However, other methods for introducing DNA into cells, such as by nuclear microinjection and electroporation may also be used. For various techniques for transforming mammalian cells, See Known et al., Methods in Enzymology, 185:527-537 (1990). The particular selection of host/cloning vehicle combination may be made by those of skill in the art after due consideration of the principles set forth without departing from the scope of this invention (See, e.g., Sambrook et al., *Molecular Cloning, A Laboratory Manual* $2^{nd}$ edition, 1989, Cold Spring Harbor Press, NY).

Recombinant gene expression may be measured in a sample directly, for example, by conventional Northern blotting, RT-PCR or quantitative real time RT-PCR (qRT-PCR) to quantitate the transcription of mRNA (Thomas, *Proc. Natl. Acad. Sci.* USA, 77:5201-5205 (1980)).

Recombinant gene expression, alternatively, may be measured by immunological methods, such as immunohistochemical staining of cells or tissue sections and assay of cell culture or body fluids, to quantitate directly the expression of gene product. Antibodies useful for immunohistochemical staining and assay of sample fluids may be either monoclonal or polyclonal, and may be prepared in any mammal. Conveniently, the antibodies may be prepared against a native sequence polypeptide or against a synthetic peptide based on the DNA sequences provided herein or against exogenous sequence fused to Δ9 or Δ8, 9 DNA and encoding a specific antibody epitope.

It may be desired to purify recombinant Δ9 or Δ8, 9 from host cell proteins. The following procedures are exemplary of suitable purification procedures: by fractionation on an ion-exchange column; reverse phase HPLC; chromatography on silica or on a cation-exchange resin such as DEAE; chromatofocusing; SDS-PAGE; ammonium sulfate precipitation; metal chelating columns; or a specific antibody column to bind epitope-tagged forms of the protein of interest (e.g., nickel columns to bind His-tagged proteins, anti-HA columns to bind HA-tagged proteins, or anti-FLAG columns to bind FLAG-tagged proteins). Various methods of protein purification may be employed and such methods are known in the art and described for example in Deutsche, *Methods in Enzymology*, 182 (1990); Scopes, Protein Purification: Principles and Practice, Springer-Verlag, New York (1982). The purification step(s) selected will depend, for example, on the nature of the production process used and the particular antigen produced.

The present invention further provides a pharmaceutical composition for alleviating inflammatory bowel disease in a subject which comprises a purified protein of the invention and a pharmaceutically acceptable carrier.

Pharmaceutically acceptable carrier encompasses any of the standard pharmaceutical carriers. The pharmaceutical composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions. In an embodiment, the pharmaceutical composition is suitable for administering a nasal route to a subject. An example includes aerosolized solution.

IL-23 is a heterodimeric cytokine belonging to IL-6 helical cytokine family. It is composed of two disulfide-linked subunits, p19 and p40. p40 is also a component, with p35, of IL-12, a cytokine in this same family. This allowed the relative contribution of IL-23 and IL-12 to autoimmune disease to be clarified, when the p19 and p35 subunits were targeted in gene knockout studies. IL-23p19, but not IL-12p35, deficient mice were resistant or showed decreased pro-inflammatory responses in experimental autoimmune encephalomyelitis, inflammatory bowel disease and collagen-induced arthritis. Thus, IL-23 (and by inference, its receptor) became established as an important component of autoimmune inflammatory disorders.

Th17 cells represent a novel, distinct subset of CD4+ T-helper cells. Differentiation of naive human CD4$^+$ T cells to Th17 cells is recognized to have critical functions in autoimmune disease models in mice. Evidence indicates that mice deficient in p19, the unique subunit of IL-23, demonstrated resistance in different autoimmune disease models, mainly because of the absence of T cells producing IL-17 (i.e., Th17 cells). Differentiation of Th17 cells in vivo requires the presence of IL-23, which is secreted by activated antigen-presenting cells. It is well that IL-23 per se cannot induce the differentiation of naive CD4+ T cells into Th17 cells in vitro, but may synergies with Th17 cell differentiation agents including IL-1, IL-6 and TGF-β to induce expression of IL-17 cytokine. According to one embodiment, the present invention provides a therapeutic application of a soluble truncated IL-23Rα (e.g., Δ9). Hence, Δ9 has the capability of inhibiting the cell signaling mediated by IL-23 as well as inhibiting the maturation of Th17 cells. The present inventors believe that Δ9, when administered, would behave as an inhibitor to inhibit the IL-23-mediated cell signaling and Th17 maturation, and thus alleviating the development and progression of Th17-associated diseases such as inflammatory bowel diseases that include Crohn's disease.

In one embodiment, the present invention provides Δ9 that represents a soluble form of the IL-23α receptor extracellular domain by transiently transfect the Δ9 expression construct (SEQ ID NO: 1) into a mammalian expression cell system (e.g., 293-T cells; human embryonic kidney fibroblast cells).

In one embodiment, the present invention provides Δ8, 9 that represents a soluble form of the IL-23α receptor extracellular domain by transiently transfect the Δ8,9 gene (SEQ ID NO: 3) into a mammalian expression cell system (e.g., 293-T cells; human embryonic fibroblast cells).

In one embodiment, the Δ9 or Δ8, 9 genes may be stably transfected into a mammalian expression cell system using standard protocols as recognized by one of ordinary skill in the art.

In one embodiment, the present invention provides an ELISA to aid detecting the circulating level of the soluble truncated IL-23Rα protein. One of ordinary skill in the art would recognize the use of commercially-available antibodies in the present developed Δ9 ELISA. Using an ELISA, it is demonstrated that Δ9 is present at low levels in the periphery of healthy individuals. Similarly, the present inventors believe that Δ8,9 are present in patients suffering from inflammatory bowel diseases. Soluble cytokine receptors may be generated by several mechanisms, including proteolytic cleavage of receptor ectodomains, alternative splicing of mRNA transcripts or transcription of distinct genes. The present inventors believe that Δ9 (and Δ8,9) present in the circulation is solely a result of alternative splicing of the native IL-23Rα mRNA. Given the human genome project is completed, it is believed that it is highly unlikely that there is a distinct gene encoded for a soluble form of IL-23Rα chain.

In one embodiment, the present invention provides a therapeutic application of the soluble truncated IL-23Rα. More particular, the present inventors have discovered that Δ9 or Δ8,9 are effective in inhibiting IL-23-mediated cell signaling. In another embodiment, the present invention provides the use of Δ9 or Δ8,9 in inhibiting STAT formation. In yet another embodiment, the present invention provides the use of Δ9 or Δ8,9 to inhibit Th17 cell maturation. The present finding is in great contrast with the original report by Parham et al. who described the human and mouse IL-23 receptor, despite their binding by their external domain Fc and V5-HIS6 constructs. According to Parham, "neither [human and mouse IL-23 receptor) could act as effective antagonists." The present invention provides a naturally-occurring form of Δ9 (or Δ8,9) form can inhibit STAT3 phosphorylation and Th-17 cell differentiation in an in vitro human leukocyte assay, starting from naive CD4$^+$ T cells. Notably, the present finding cannot be explained by Δ9 or Δ8,9 signaling via IL-12. Our data showed that Δ9 and Δ8,9 binds to IL-23 but not its sister cytokine IL-12, thus further demonstrated that this was via the p19, not the p40, component.

In one embodiment, the present invention provides a soluble truncated IL-23Rα that inhibits the secretion of IL-17A and IL-17F. IL-23 is the key element in the final stages of Th-17 phenotypic maturation. In the present Th-17 maturation assays, naive CD4$^+$ T cells were successfully differentiated to Th17 cells, based on their up-regulation of RORγt (the signature transcription factor for this cell subtype), and secretion of IL-17A and IL-17F. The induction of IL-17A&F expression was abolished when Δ9 (or Δ8,9) was present is consistent with the observation that Δ9 did not affect changes in RORγt expression level. These results reinforce our hypothesis that Δ9 (or Δ8,9) can function as a naturally-occurring specific inhibitor of IL-23 which has the ability to regulate Th-17 cell development.

In one embodiment, the present invention provides that Δ9 (and Δ8,9) can suppress the secretory phenotype of human Th17 cells, demonstrating the existence of a novel regulatory mechanism for human Th17 cells. The present findings have practical utility for the therapeutic application of Δ9 and Δ8,9. Specifically, Δ9 or Δ8,9 may be used as a therapeutic agent for treating human Th17-dependent conditions such as Crohn's Disease, asthma and psoriasis. Many attempts have been made based on the premise that IL-23 is a target for anti-inflammatory therapies, particularly in the intestine; the present finding adds that Δ9 or Δ8,9 may represent a novel tool in this process.

The present invention provides a method of treating or alleviating inflammatory bowel disease in a subject which comprises administering to the subject an amount of any of the aforementioned compositions comprising the invented purified proteins, said amount effective to block IL-23 cell signaling in the subject. A subject may be a mammal, for example, a human.

The present invention will be better understood from the following experimental studies. One of ordinary skill in the art would readily appreciate that the specific methods and results discussed therein are not intended to limit the invention. The experimental studies merely serve illustrative purposes, and the invention is more fully described by the claims which follow thereafter.

EXPERIMENTAL STUDIES

Example 1

Multiple Potential Splice Variant Forms of IL23Rα in Human Leukocytes

In a previous study, we reported the identification of twenty-four (24) potential IL-23Rα "deletion" splice variants and one (1) "insertion" splice variant in human leukocytes (*Genes and Immunity* (2008) 9: 631-639 & 566-569, 2008). The expression level of these IL-23Rα splice variants in vivo was unclear because of the lack of a reliable quantitation assay which permits the measurement of these variant transcripts in vivo. However, it was noted that a majority of these IL-23Rα splice variants introduce early termination codons to the open reading frames immediately after the alternative splicing event, which may produce premature proteins with only short peptides of the IL-23Rα. Lacking such critical information, the physiological and pathological roles of their translated proteins, if any, are unknown.

Example 2

Determination of Six (6) IL-23R Splice Variants in Human Leukocytes

Figure 1:
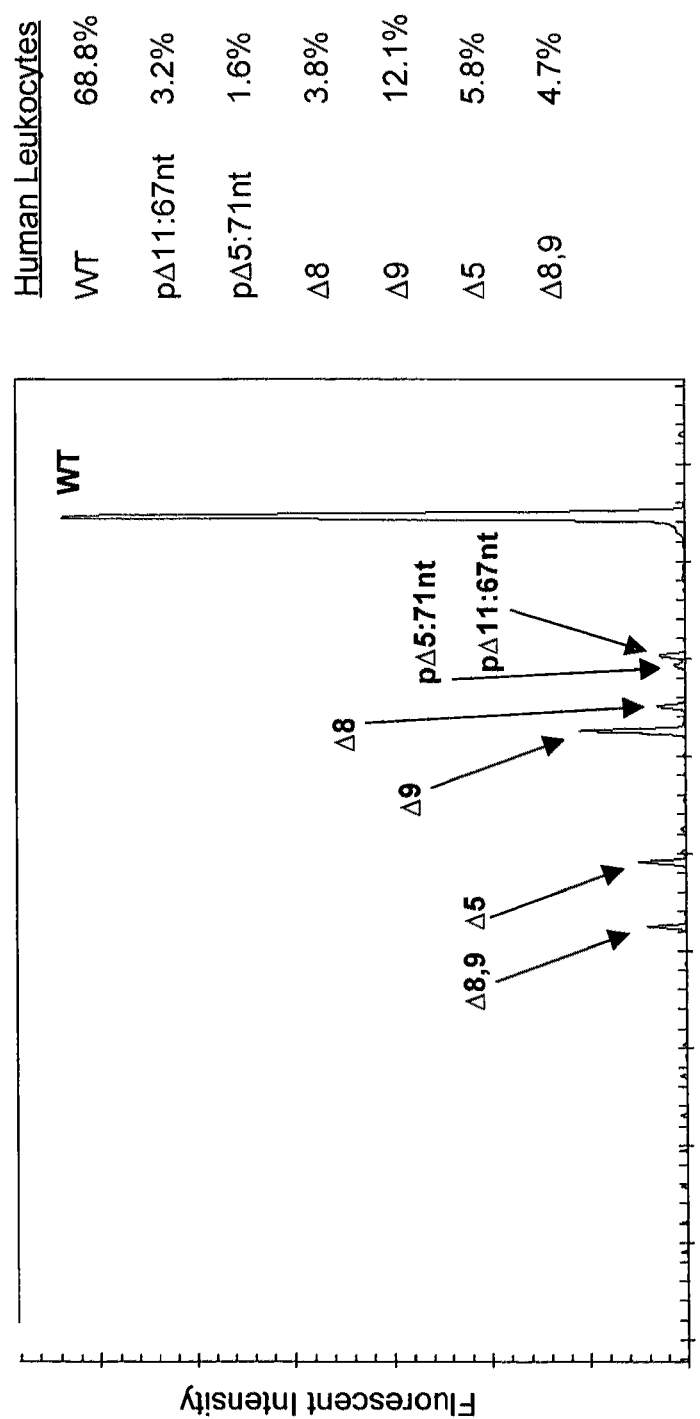
FIG. 1 depicts the expression profile of IL-23R splice variant forms in human leukocytes. Note that six (6) splice variants were detected out of twenty four (24) potential "deletion" splice variants. Relative expression level is listed as % of total on the right panel.

In the present study, we specifically addressed the issue if these IL-23Rα splice variants may be present in vivo. To do so, we performed a Fragment Analysis to semi-quantitatively measure the mRNA expression level of these IL-23Rα isoforms in a single PCR reaction using a Beckman CEQ8000 machine. We compared quantitatively the individual human IL-23Rα splice variant forms relative to the full-length (wild-type, "wt") IL-23Rα form (FIG. 1).

Human leukocytes (i.e., PBMC) were isolated and used as a cellular model to examine the expression of different IL-23Rα isoforms. RNA was extracted (using Stratagene RNA mini-prep kits) from the isolated PBMC and its concentration was measured in Nanodrop. Two (2) micrograms (μg) of RNA was reversely transcribed into cDNA. A pair of gene specific IL-23R primers (P5) and (P6), which was fluorescent labeled (P6-D3), was designed to amplify IL-23R isoforms by PCR (see "Materials & Methods" section, infra, for primer sequence information). Amplified products were denatured, run on the CEQ8000 machine and separated by size. Peaks were assigned to the corresponding variants based on their size. The fluorescent signal represented the level of expression.

Using this assay, we found that not all of the potential IL-23Rα isoforms are detectable. To our surprise, we routinely detected only six (6) IL-23Rα splice mRNA variants (See, FIG. 1). These IL-23Rα splice mRNA variants include Δ8,9; Δ5; Δ9; Δ8; pΔ5:71 nt; and pΔ11:67 nt. (FIG. 1).

Example 3

Identification of a Major Splice Variant of IL-23Rα-Δ9 Splice Variant

Of the six (6) human IL-23Rα mRNA variant forms, one constituted a single major alternative splice variant form of IL-23Rα (i.e., Δ9) in the leukocyte cells tested. While the wild-type occupies ~68% of the total population of IL-23Rα, Δ9 has ~12% (FIG. 1). Further examination revealed that this mRNA variant lacks the exon-9 (human IL-23RαΔ9; "Δ9"). In several experiments, the Δ9 splice variant was found to represent between 12-20% of the total IL-23Rα mRNA. We concluded that this particular IL-23Rα spice variant exists in vivo as a major splice variant for IL-23Rα. We therefore focused our attention on this particular Δ9 variant in our subsequent experiments.

Example 4

Figure 2:
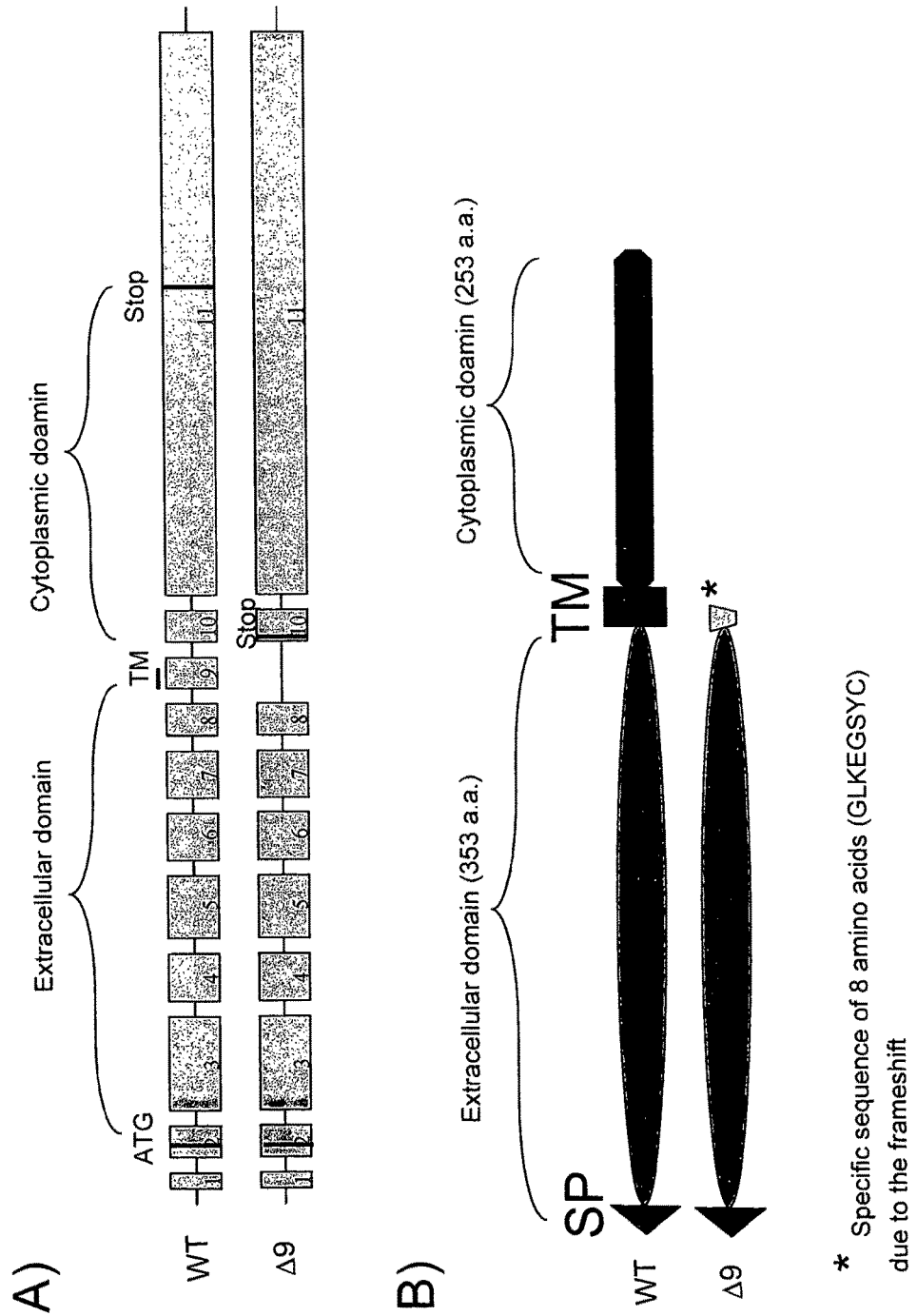
FIG. 2 depicts the schematic representation of wild-type IL-23Rα and its Δ9 variant.

Gene and Protein Organization Analysis of the Δ9 Splice Variant—Identification of the GLKEGSYC Sequence FIG. 2 summarizes the gene organization as well as protein domain structures of wild-type IL-23Rα and its Δ9 deletion splice variant form. Located on chromosome 1, the native form of human IL-23Rα mRNA is 2.8 kb long and contains 11 exons (NM_144701). The transcribed mRNA is translated into a protein of 629 amino acids, the sequence of which is listed in NM_144701. The wild-type IL-23Rα protein translation starts at exon 2 and stops at exon 11. The extracellular domain, which binds to IL-23 cytokine, is encoded by exon 2-exon 8. Exon 9 encodes the amino acid sequence for a type-I transmembrane domain. The cytoplasmic domain, which functions to initiate cellular signaling, is encoded by part of exon 9, exon 10 and exon 11. (FIG. 2A). The human IL-23Rα protein contains a signal peptide (SP) at its N-terminus followed by extracellular domain (353 amino acids), transmembrane domain and a cytoplasmic domain (256 amino acids). (FIG. 2B).

The Δ9 splice mRNA variant is generated when the deletion of exon-9 results in a frame-shift on splicing of exon-8 to exon-10 (FIG. 2A). Accordingly, the Δ9 protein represents a truncated human IL-23Rα protein whose extracellular domain contains five (5) amino acid deletion at the C-terminus, and which lacks the membrane anchor (i.e., transmembrane domain) and cytoplasmic domain (i.e., intracellular signaling domain) (FIG. 2B) is generated.

In this study, we identified the Δ9 mRNA variant by PCR amplification using mRNA extracted from the human leukocytes. The RT-PCR products were then cloned into a plasmid vector (i.e., TOPO TA vector PCR2.1 from Invitrogen (Calrsband, Calif.)). Colony PCR was applied using M13 forward and M13 reverse primers located on either side of the TA cloning sites on the vector to screen the colonies containing PCR insert according to the manufacture's protocol. We performed gene sequencing reaction and obtained the sequence information of the PCR insert. FIG. 3A summaries the nucleotide sequence of the coding region for Δ9 (Top) (SEQ ID NO: 1) as well as the amino acid sequence for the translated Δ9 protein (Below) (SEQ ID NO: 2).

Figure 3C:
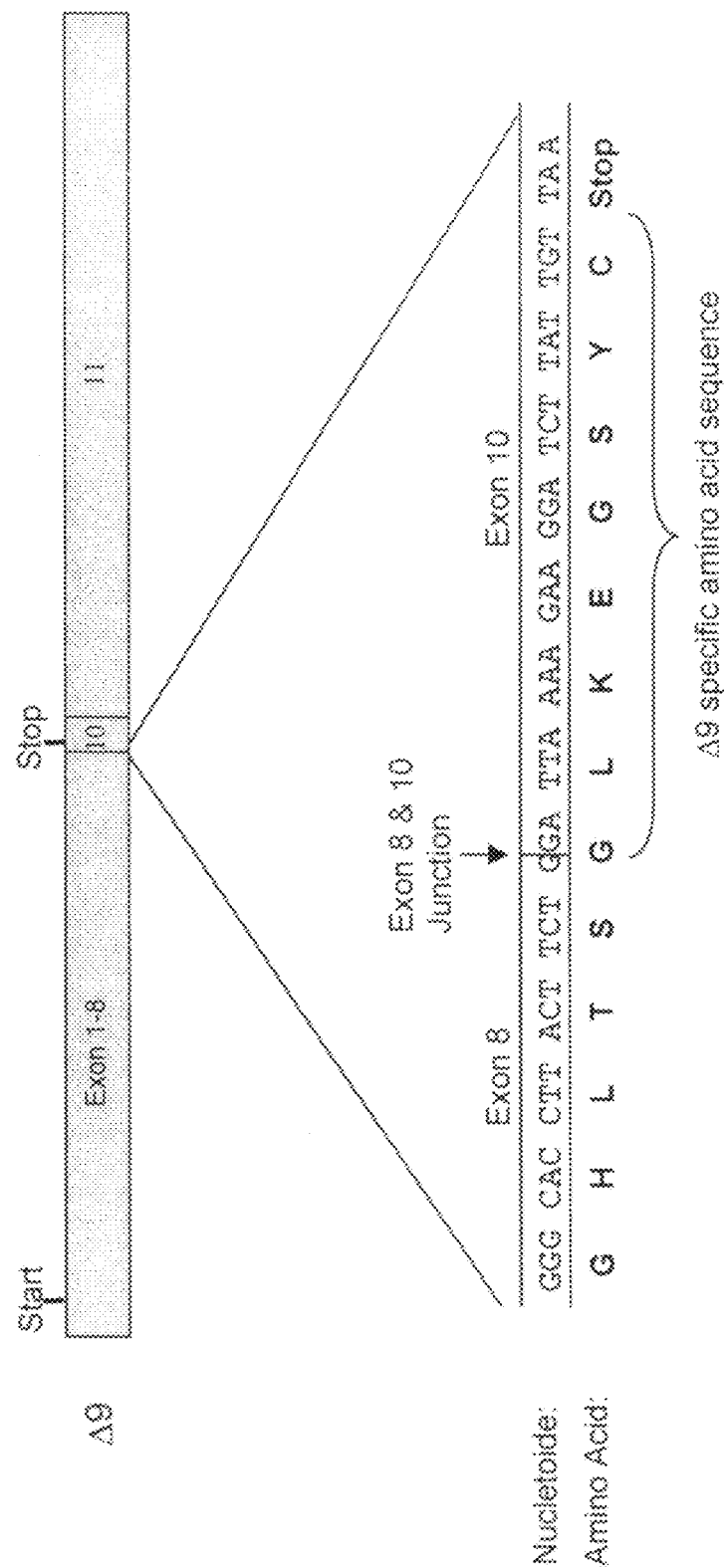
FIG. 3C depicts the exon 8 and 10 junction for Δ9.

The translated Δ9 protein has 356 amino acids and notably contains a unique eight (8) amino acid sequence at the C-terminus (FIG. 3A). The entire amino acid sequence is set forth in FIG. 3A as SEQ ID NO: 2. Because of the alternative translation reading frame used on exon 10 (resulted from the alternative splicing event), an extra eight (8) amino acids are uniquely present in the Δ9 protein, which is not present in the naïve full-length IL-23Rα protein (FIGS. 3B and 3C). This observation indicates that the amino acid sequence (GLKEGSYC, SEQ ID NO: 9) present in Δ9 is novel and unique to the Δ9 protein.

Example 5

Expression and Purification of Recombinant Δ9 Protein in the Mammalian Cell (293T Cells)

In this series of study, we sought to recombinantly express the Δ9 variant in order to obtain the recombinant Δ9 protein. To do so, we prepared both the wild-type IL-23Rα and Δ9 variant expression constructs.

a) cDNA and Construction of Expression Plasmid

The cDNAs of the wild-type IL-23Rα and Δ9 variant were obtained by the PCR amplification (see "Materials & Methods").

We inserted a "FLAG" sequence to the reverse primers to tag the recombinant protein for purposes of ease of purification and detection. The PCR products were sub-cloned into the pcDNA3.3 TOPO vector, using TA cloning kit from Invitrogen (Carlsbad Calif.) (see Method). The nucleotide sequences for the wild-type IL-23Rα and Δ9 variant expression constructs were verified by the DNA sequencing. Both forms were tagged with the "FLAG" sequence at the C-terminus of expressed protein.

b) Mammalian Expression of Recombinant Proteins

We performed transient transfections with FLAG-tagged wild-type or Δ9 expression constructs (i.e., mammalian expression vector containing coding nucleotide sequences of interest) in 293T cells using FuGENE HD following the manufacture's protocol (Roche) (see "Materials & Methods").

Figure 4:
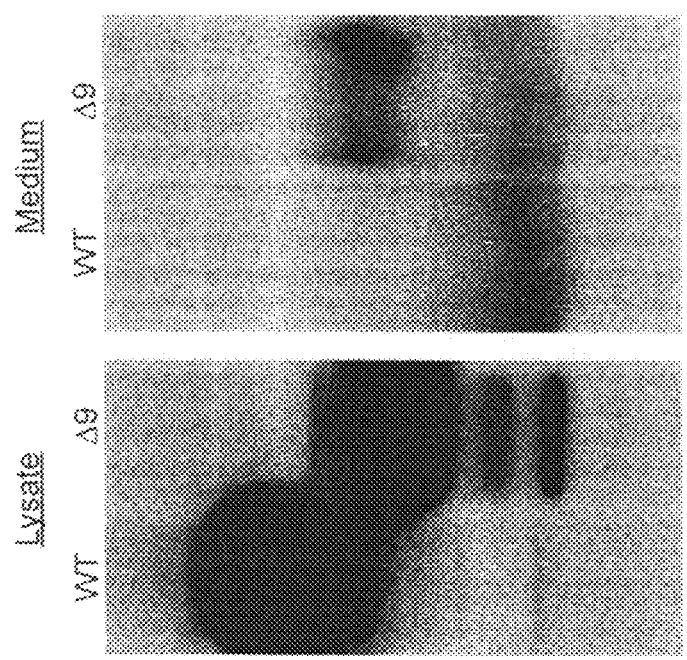
FIG. 4 depicts an immunoblot experiment using anti-Flag antibody to detect recombinant wild-type IL-23Rα protein and Δ9 protein in the cell lysates and cultured media of the 293T cells transfected with the wild-type IL-23Rα or Δ9 expression plasmids. Both recombinant proteins were expressed at similar level inside the cells. However, only Δ9 protein was detected in the culture medium. The observation demonstrates that Δ9 protein is a secreted protein and represents the soluble IL-23Rα chain.

Cellular lysates and culture media were harvested 48 hours post-transfection (see "Materials & Methods"). We detected the recombinant protein expression by the immunoblot using Anti-Flag M2 antibody (Sigma). Both expression constructs showed similar intra-cellular expression levels (using anti-FLAG Western blotting) in the transient transfection assay performed in the 293T cells. However, we only detected Δ9 protein variant in the culture medium, indicating that it was efficiently processed for secretion (FIG. 4). Because the wild-type IL-23Rα protein was absence in the culture medium, this indicated that Δ9 protein was present via active secretion, rather than being released following cell death. This observation is in concord with our hypothesis that Δ9 protein variant represents a secreted soluble form of IL-23Rα.

Under reducing and denatured gel electrophoresis (SDS-PAGE), the "Flag" tagged Δ9 protein variant exhibits ~65 kDa molecular weight (FIG. 4). The molecular weight for the wild-type IL-23Rα was ~115 kDa, which was higher than that of Δ9 protein variant.

c) Purification of Recombinant Δ9 Protein from the Transient Transfected 293T Cells We transfected a mammalian cell (i.e., human embryonic kidney fibroblast cell; 293T cell) with either the control expression vector alone or the expression vector carrying the Δ9 coding nucleotide sequence (i.e., SEQ ID NO: 1). Cell lysates and culture media were prepared and collected for the purification purpose (see "Materials & Methods").

Cells were lysed and cellular lysates were prepared. Δ9 protein was then immuno-purified using an anti-Flag M2 affinity gel (Sigma). The immuno-precipitated Δ9 protein was eluted by incubating with excess amount of Flag peptide (see Method). The purity of Δ9 protein was assayed by SDS-PAGE gel followed by Coomassie-blue staining.

Figure 5:
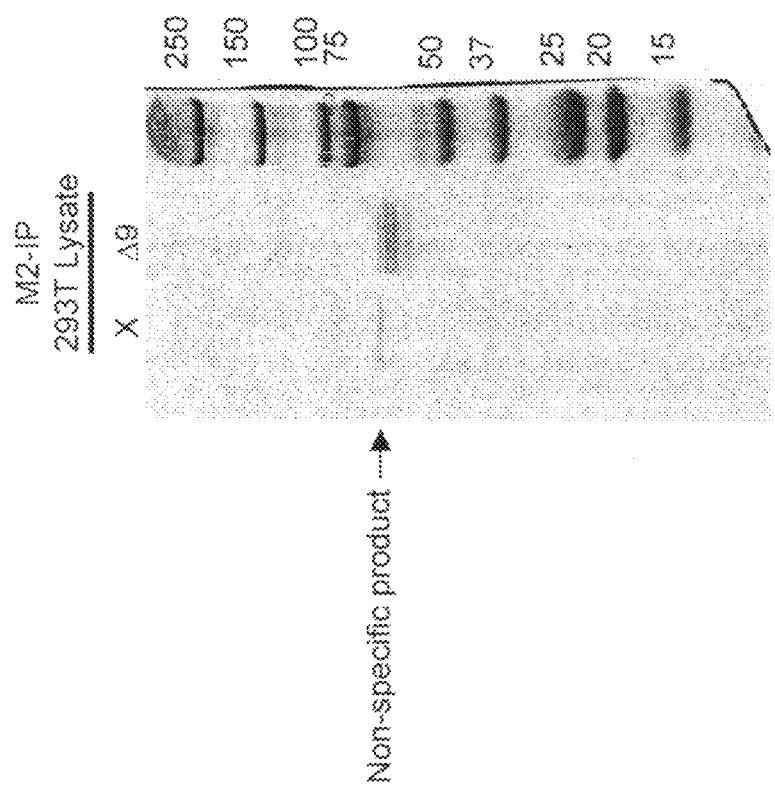
FIG. 5 depicts the purified Δ9 protein from the intracellular source (cell lysate) on the SDS-PAGE gel stained with the Coomassie Blue to reveal the purity and estimate the quantity.

No specific band was detected from 293T cell lysate transfected with empty vector, whereas Δ9 protein purified from the cell lysate transfected with Δ9 expression plasmid showed multiple bands (FIG. 5).

Cytokine receptor (i.e. IL-23Rα) is known to undergo N-glycosylation modification (See Example 12). It is possible that not all the intracellular Δ9 IL-23Rα proteins are fully N-glycosylated, resulting in a heterogeneous population of purified Δ9 IL-23Rα.

Figure 6:
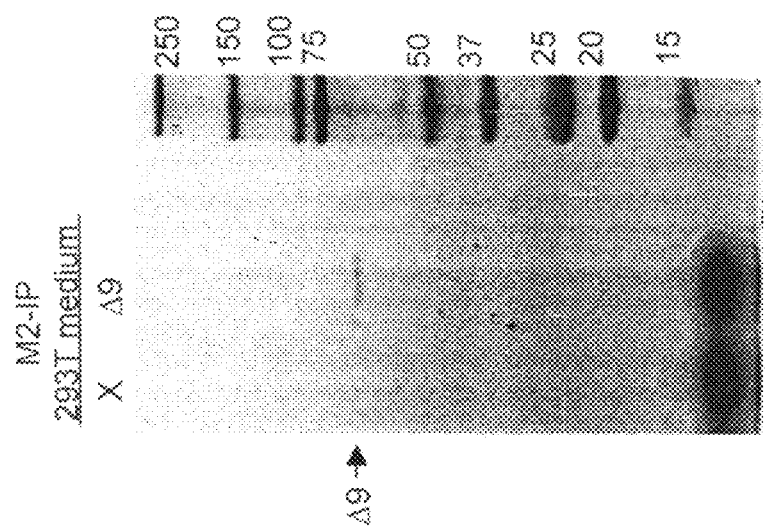
FIG. 6 depicts the purified Δ9 protein from the secreted source (culture medium) on the SDS-PAGE gel stained with the Coomassie Blue to reveal the purity and estimate the quantity.

We also performed the purification experiment using the culture media from the 293T cells transfected with empty vector or Δ9 expression plasmid. No protein was detected from 293T cell lysate transfected with empty vector, whereas the purified Δ9 protein from secreted source (culture media) showed a homogenous population as a single band of ~65 kDa in size (FIG. 6).

Example 6

Development of ELISA to Detect Δ9 Levels

To determine whether the Δ9 protein variant form occurs naturally, we developed an ELISA assay to detect soluble human IL-23Rα. In the following series of studies, we sought to detect Δ9 protein in culture cell supernatants. We also sought to determine if the Δ9 protein is present in the blood circulation of healthy individuals and compared that with patients suffering from inflammatory bowel diseases (e.g., Crohn's disease). In summary, we have established that a soluble variant of the human IL-23Rα exists that is generally present at low levels in the circulation of healthy individual, but the level increases with Crohn's patients.

I. ELISA Development

Using the recombinant expressed IL-23Rα proteins in the 293T cells (see "Materials & Methods" for the construction of expression plasmids), we proceeded to develop an ELISA sandwich system. The ELISA system allows detection of the soluble form of human IL-23Rα (Δ9). In this ELISA system, two anti-hIL-23Rα antibodies are required, each recognizing different epitopes on IL-23Rα. The cell lysates obtained from the transient transfection experiment were used to examine the antibody specificity and epitope mapping.

a) Capture Antibody

Figure 7:
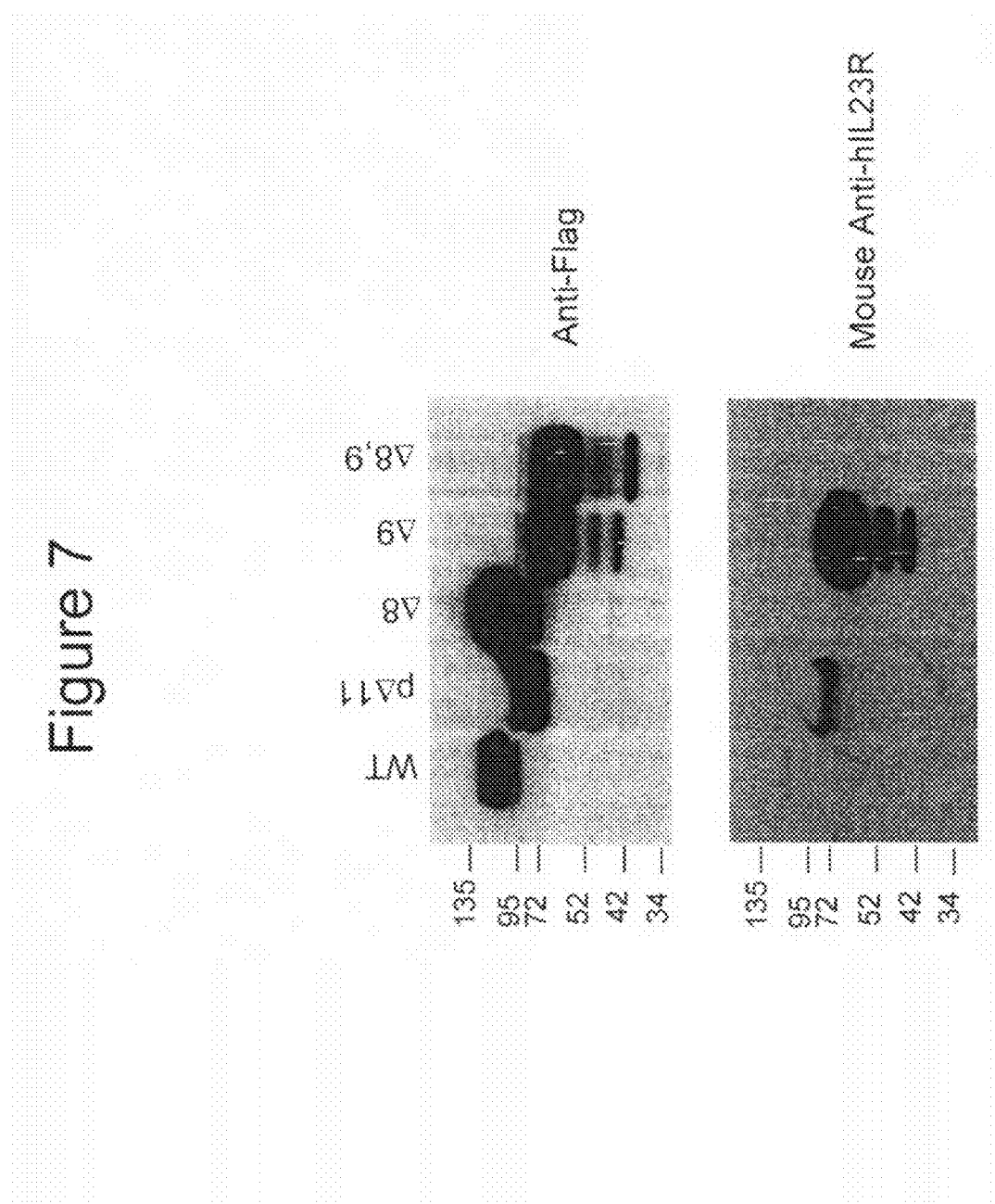
FIG. 7 depicts the specificity of mouse anti-IL-23Rα antibody in the immunoblot experiment using cellular lysates from the 293T cells transfected with five (5) different expression plasmids. All the recombinant proteins were tagged with Flag sequence at the C-terminus. The top panel was the immunoblot experiment using anti-Flag antibody to show that all the recombinant proteins were expressed at comparable level. The bottom panel was the immunoblot experiment using mouse anti-IL-23R antibody to map the epitope of this mouse anti-IL-23R antibody.

Mouse anti-human IL-23Rα was used in the immunoblot assay (FIG. 7 Bottom). We also performed the immunoblot assay using anti-Flag to show that all the recombinant proteins expressed at a similar level (FIG. 7 Top). The mouse anti-human IL-23Rα antibody was used as a capture antibody and it recognizes the wild-type IL-23Rα, pΔ11 and Δ9. More importantly, this mouse anti-human IL-23Rα antibody is found to be highly sensitively to Δ9.

Because this antibody fails to detect Δ8 and Δ8,9 proteins, it is speculated that the antibody recognizes the C-terminal region of extracellular domain encoded by exon 8.

Figure 8:
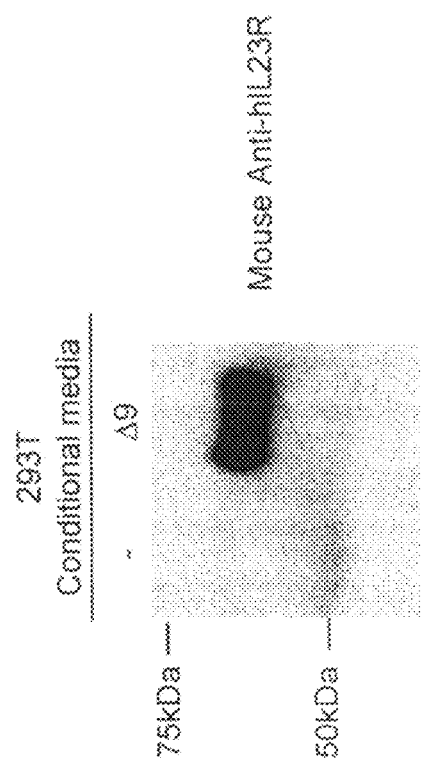
FIG. 8 depicts an immunoblot experiment using a mouse anti-IL23R antibody to detect the recombinant Δ9 protein in the culture media obtained from 293T cells transfected with either control plasmid or Δ9 expression plasmid.

FIG. 8 depicts an immunoblot experiment using cultured media obtained from the 293T cells transfected with either the empty vector or Δ9 expression plasmid. The mouse anti-human IL-23Rα antibody detected both Δ9 present inside the cell (i.e., from cell lysate source) (FIG. 7) and Δ9 present in the culture medium (FIG. 8).

In addition to the commercially available mouse anti-hIL-23Rα antibody (R&D Systems), we also prepared different mouse monoclonal antibodies targeted against human IL-23Rα protein (i.e., amino acid residues 116-129). Synthetic peptides covering this region were used as antigen and injected into mice to prepare monoclonal antibodies. Several hybridoma cells were generated. We selected four (4) hybridoma cells and obtained purified monoclonal antibodies from these hybridoma supernatants. All these hybridomas show avid binding (i.e., high affinity) to the peptide antigen (i.e., amino acid residues 116-129).

The four (4) hybridoma clones were identified as 2C8E10, 2C8C4, 3A5C11 and 3A5D11. Monoclonal antibodies secreted by these hybridoma cells were further purified using Protein A resin (standard protocol). The purified monoclonal antibodies were tested in two (2) different validation assays: namely (i) immunoprecipitation and (ii) ELISA.

All four (4) monoclonal antibodies were shown to immunoprecipitate Δ9 protein. Immunoprecipitation was performed using standard protocol (See "Materials & Methods).

Two (2) of the purified monoclonal antibodies from hybridoma cells (i.e., 3A5C11 and 3A5D11) were tested using our ELISA. Instead of using the commercially available mouse anti-hIL-23Rα antibody from R&D as the capture antibody, we used our purified monoclonal antibodies (i.e., 3A5C11 and 3A5D11) in the ELISA to measure the amount of soluble human IL-23Rα. We found that both of our monoclonal antibodies are capable of capturing soluble human IL-23Rα similar to the commercially available mouse anti-hIL-23Rα antibody (See Table below).

TABLE 1

Characterization of our prepared monoclonal antibodies

| Clone IDs: | Immunoprecipitation | ELISA as Capture Antibody |
|---|---|---|
| 2C8E10 | Yes | N.D. |
| 2C8C4 | Yes | N.D. |
| 3A5C11 | Yes | Yes |
| 3A5D11 | Yes | Yes | b) Detection Antibody

Goat anti-human IL-23Rα was used as a detection antibody. The goat anti-human IL-23Rα is preferably in biotinylated form.

Figure 9:
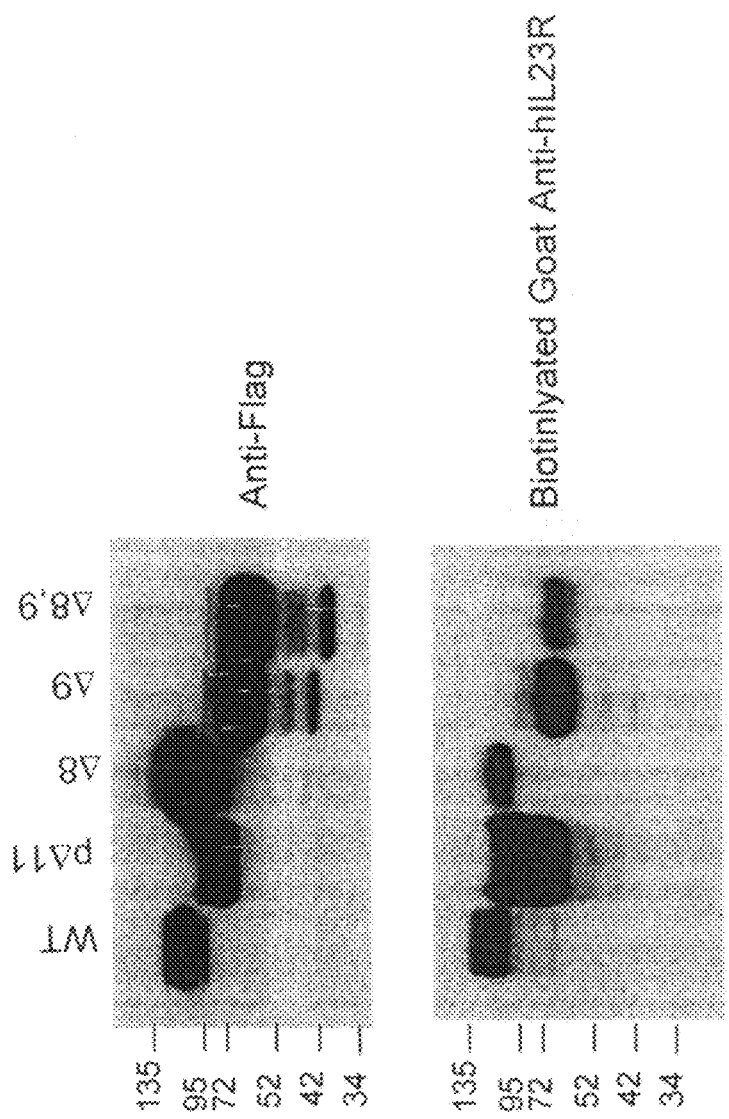
FIG. 9 depicts the specificity of biotinylated goat anti-IL-23R antibody in the immunoblot experiment using cellular lysates from the 293T cells transfected with five (5) different expression plasmids. All the recombinant proteins were tagged with Flag sequence at the C-terminus. The top panel was the immunoblot experiment using anti-Flag antibody to show that all the recombinant proteins were expressed at comparable level. The bottom panel was the immunoblot experiment using biotinylated goat anti-IL-23R antibody.

We examined the specificity of the biotinlyated goat anti-human IL-23Rα (FIG. 9 Bottom). We also performed the immunoblot assay using anti-Flag to show that all the recombinant proteins expressed at a similar level (FIG. 9 Top). This goat antibody detects all the expressed proteins. More importantly, the goat antibody recognizes a different epitope from that of the mouse antibody.

As such, the mouse and goat anti-human IL-23Rα antibodies were used as a "match antibody pair" in the ELISA. The mouse antibody was used as the capture antibody because of its high sensitively to Δ9, whereas the biotinlyated goat antibody was used for detection.

c) ELISA Sandwich

Figure 10:
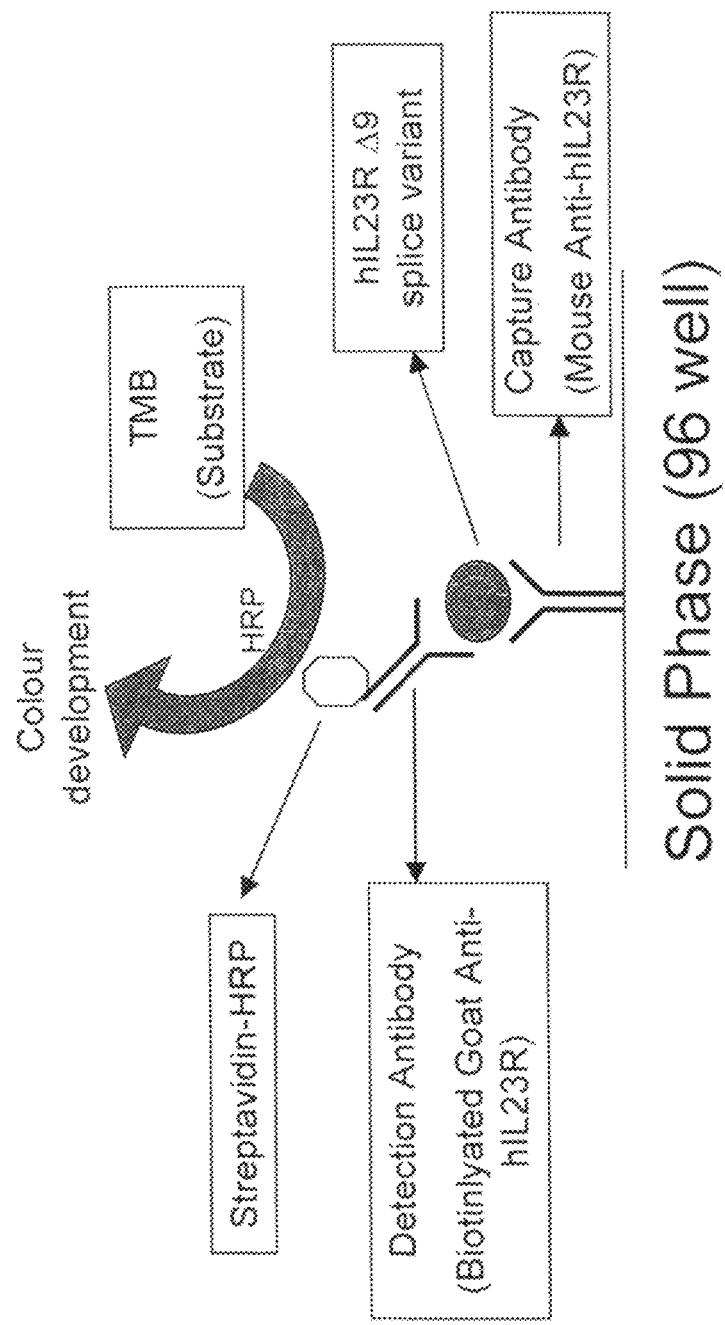
FIG. 10 depicts the ELISA sandwich using two (2) different anti-human IL-23Rα antibodies. The mouse anti-human IL-23Rα antibody was used as capture antibody and coated on the solid support (e.g., microtiter plate) to capture the soluble form of the IL-23Rα. The capture antibody specifically captured the Δ9 variant on the ELISA plate. The captured Δ9 variant was then detected by a biotinlyated goat anti-human IL-23Rα antibody. The antibody-antigen sandwich was detected by streptavidin conjugated with horseradish peroxidase (HRP). The peroxidase activity (representing the level of Δ9) was measured by addition of tetramethylbenzidine (TMB) substrate. The color intensity was in direct proportion to the amount of the bound IL-23Rα. Color development was stopped and the intensity of the color was measured at optical density (OD) 450 nm on a microtiter plate reader.

FIG. 10 depicts the ELISA sandwich using 2 different anti-human IL-23Rα antibodies. In this series of study, the mouse anti-human IL-23Rα antibody was used as capture antibody and coated on the solid support (e.g., microtiter plate) to capture the soluble form of the IL-23Rα. Because the mouse antibody only detected the soluble IL-23Rα with an extracellular domain (i.e., amino acid residue number 24-348) and Δ9 is the only secreted variant containing this extracellular domain, this antibody specifically captured the Δ9 variant on the ELISA plate.

The captured Δ9 IL-23Rα was then detected by a biotinlyated goat anti-human IL-23Rα antibody. The goal anti-human IL-23Rα antibody recognizes a different epitope than that of mouse anti-human IL-23Rα antibody.

d) Detection System

The antibody-antigen sandwich was detected by streptavidin conjugated with horseradish peroxidase (HRP), which specifically binds biotin on the detection antibody. The peroxidase activity (representing the level of Δ9) was measured by addition of tetramethylbenzidine (TMB) substrate. The color intensity was in direct proportion to the amount of the bound IL-23Rα. Color development was stopped (by adding 1 M $H_2SO_4$) and the intensity of the color was measured at optical density (OD) 450 nm on a microtiter plate reader.

e) Validation of ELISA Using Purified Δ9 Proteins

Figure 11:
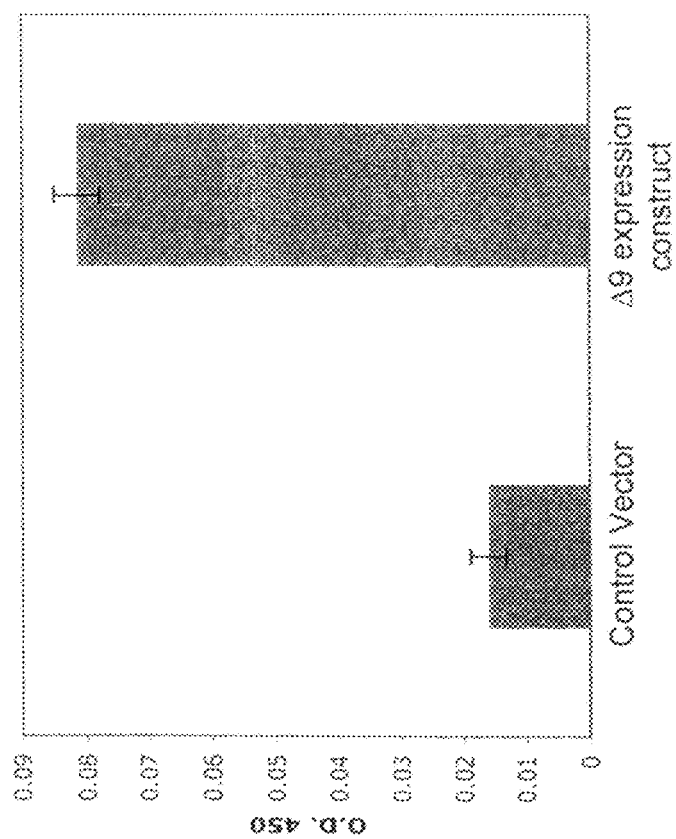
FIG. 11 depicts the validation of developed ELISA using purified intracellular Δ9 (i.e., from cellular lysates).

FIG. 11 depicts the developed ELISA. Δ9 protein purified from cellular lysate was used (See Example 5). The ELISA detects the purified Δ9 protein from the mammalian cells transiently transfected with Δ9 expression plasmid but not from the cells transiently transfected with empty expression plasmid.

Figure 12:
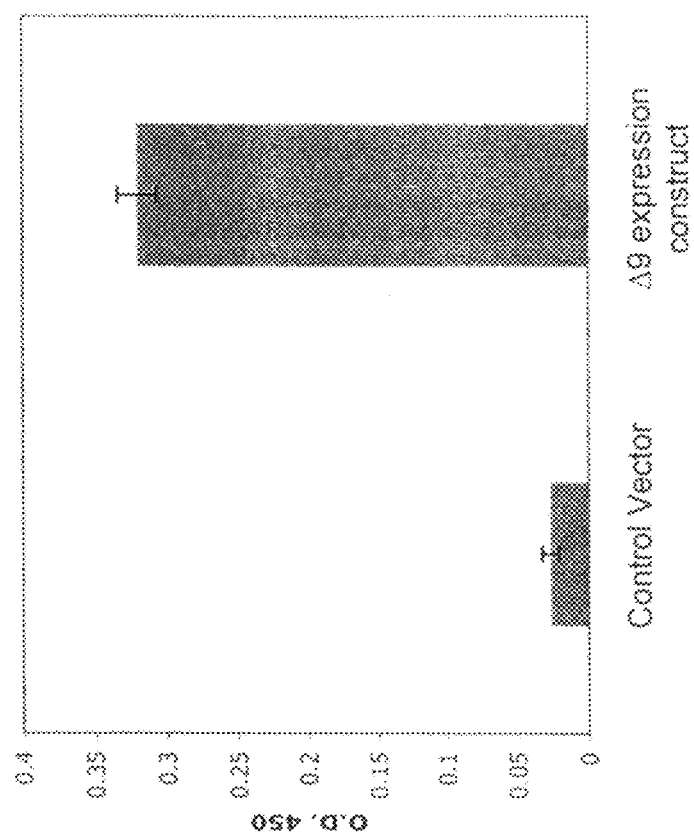
FIG. 12 depicts the validation of developed ELISA using recombinant Δ9 protein purified from the secreted source (culture medium).

FIG. 12 depicts the purified Δ9 protein from secreted source (culture medium) that was detected by the developed ELISA.

Example 7

ELISA Confirms Δ9 is a Secretary Protein

Figure 13:
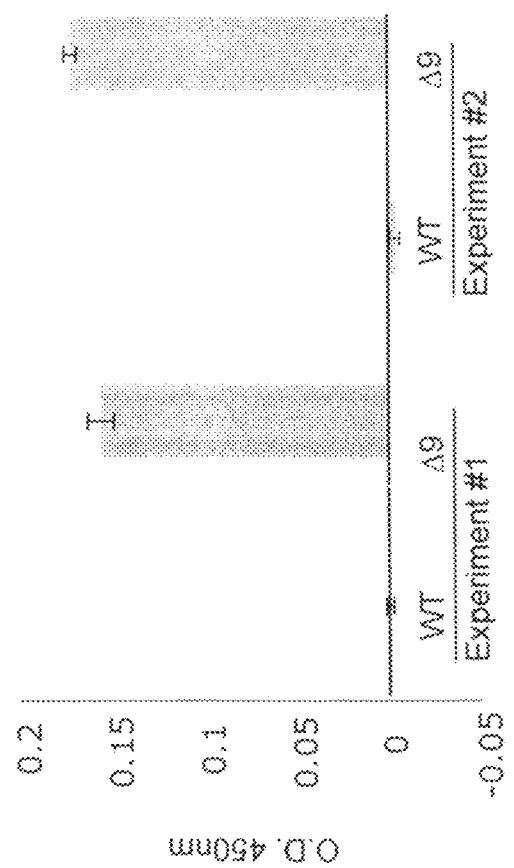
FIG. 13 depicts the ELISA experiment to detect the secreted Δ9 protein in the culture medium from the 293T cells transfected with the Δ9 expression plasmid. The result represents two (2) independent transfection experiments performed in the 293T cells.

FIG. 13 depicts the secreted Δ9 protein was detected in the 293T cells culture, medium transfected with the Δ9 expression plasmid by the developed ELISA. Because the ELISA detected the presence of Δ9 protein in the cultured media, it is concluded that the Δ9 protein is a secreted protein.

Example 8

Figure 14:
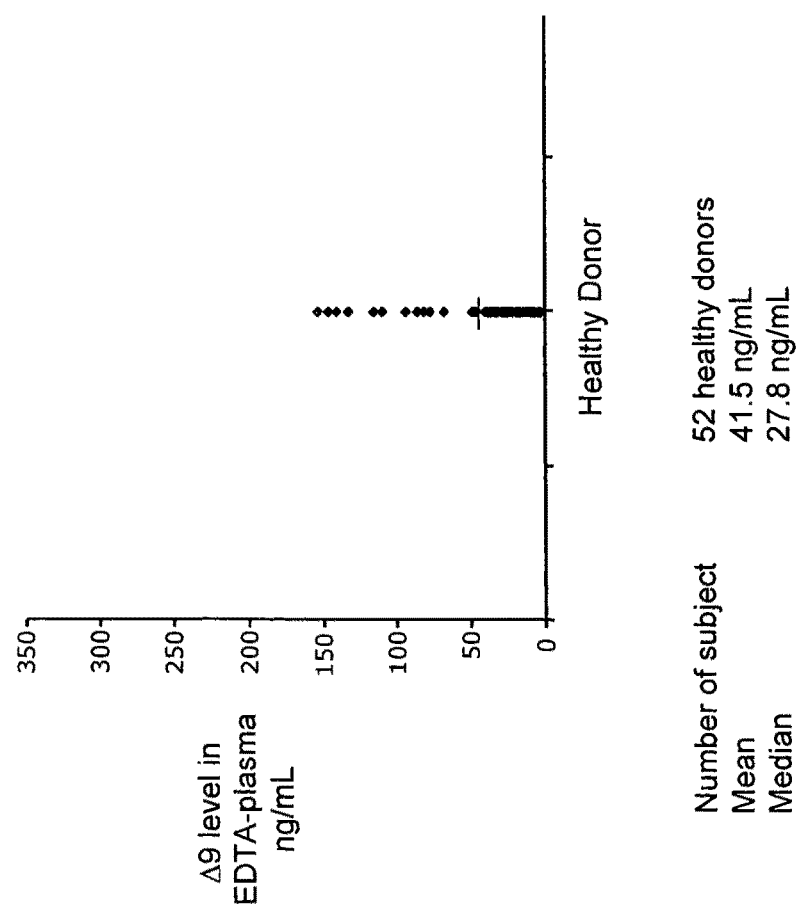
FIG. 14 depicts an ELISA experiment performed to detect the serological level of Δ9 in the plasma samples obtained from the healthy human donors with no history of Crohn's disease. Totally, fifty-two (52) control plasma samples were analyzed. The mean and median Δ9 values were 41.5 ng/mL and 27.8 ng/mL, respectively.

Patient Study—Correlation of Increased Level of Δ9 and Crohn's Disease a) Control Human Subjects FIG. 14 depicts the measurement and correlation between the serological levels of Δ9 from fifty-two (52) control human donors with no known medical history of bowel infectious abnormality including Crohn's disease. The mean and median of Δ9 IL-23Rα levels in this subject group were 41.5 ng/mL and 27.8 ng/mL, respectively.

b) Patient with Crohn's Disease

Figure 15:
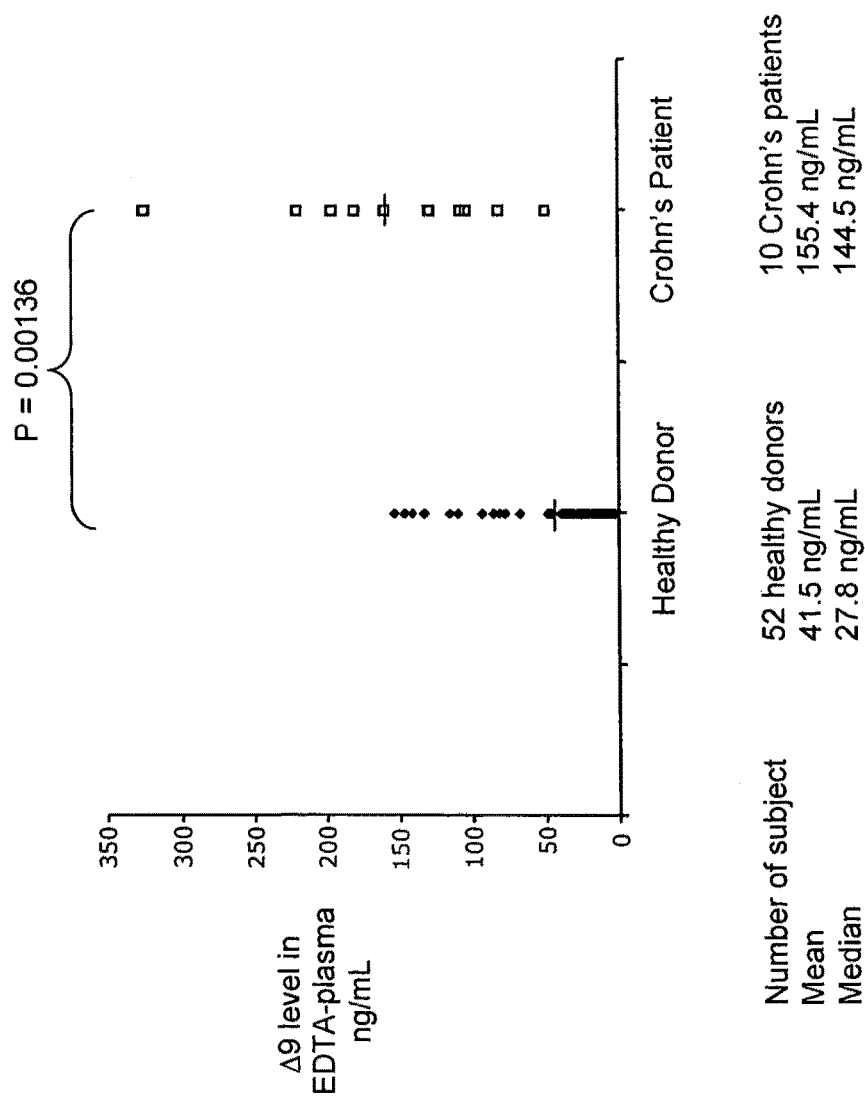
FIG. 15 depicts the ELISA experiment performed to detect the serological level of Δ9 in the plasma samples obtained from the human donors with a medical history of Crohn's disease. The mean and median values of Δ9

FIG. 15 depicts the detection of the serological levels of Δ9 IL-23R from ten (10) human donors with a known medical history of Crohn's disease. The mean and median of Δ9 IL-23Rα level were 155.4 ng/mL and 144.5 ng/mL respectively. Both mean and median in Crohn's patients were higher than that in the normal group (See FIG. 15). The difference between the two groups was statistically significant ($p=0.00136$; "T" test).

Example 9

Human Δ9 Protein Capable of Binding IL-23

We next examined whether Δ9 protein was capable of binding to IL-23. Given the sharing of the p40 chain between IL-23 (p19+p40) and the related cytokine IL-12 (p35+p40), it was also important to establish if Δ9 was specific for IL-23. Culture medium from 293T cells transfected with either empty vector or FLAG-tagged Δ9 expression construct was concentrated and incubated with 200 ng of either IL-23 or IL-12, then immunoprecipitated with anti-FLAG M2 affinity gel (See "Materials & Methods").

The immunoprecipitate was subjected to Western blotting and Δ9 or IL-23/12 was visualized with either anti-hIL23Rα or anti-hIL-12/23p40. M2 gel alone was incapable of pulling down IL-23, whereas IL-23 was detected in the precipitate when Δ9 protein was present in the precipitation reaction (FIG. 16). FIG. 17 depicts that IL-12 was not detected in the precipitate even when Δ9 protein was present in the precipitation reaction.

While both experiments confirmed that Δ9 had successfully been precipitated with anti-FLAG, only the incubation of Δ9 with IL-23 allowed visualization of the p40 band, demonstrating that Δ9 specifically binds IL-23 free in solution, but will not bind IL-12 (FIG. 17). We therefore concluded that Δ9 preferentially binds to the p19 chain of IL-23.

Example 10

Mapping of Region on Human Δ9 Protein Required for IL-23 Binding

We performed deletion analysis to identify a possible minimal domain or region that is required by the Δ9 protein that binds to IL-23 cytokine. The extracellular domain of full length IL-23Rα consists of a total of 353 amino acids (i.e., amino acid residues 1-353) (FIG. 18). In contrast, Δ9 protein consists of a total of 348 amino acids from extracellular domain of IL-23Rα (i.e., amino acid residues 1-348). As shown in FIG. 3C, when exon 9 is spliced out, exon 8 and 10 join together, which causes a frame-shift and resulting in an addition of a novel eight (8) amino acids (SEQ ID NO: 9). This amino acid addition is generated through alternative open reading frame used when exon 8 and exon 10 were joined (See, FIG. 3B and FIG. 18).

Similarly, Δ8,9 protein consists of a total of 318 amino acids from extracellular domain of IL-23Rα (i.e., amino acids 1-318) plus the same novel eight (8) amino acids generated through alternative open reading frame used when exon 7 and exon 10 were joined (See, FIG. 3E and FIG. 18).

In addition, we also prepared two (2) more IL-23Rα deletion mutants; namely, 1-250 mutant and 1-200 mutant. These deletion mutants were generated by PCR (See, FIG. 18). Together, all of the four (4) IL-23Rα protein variants (FIG. 18) were tagged with Flag sequence at the C-terminus. The expression constructs were transfected into 293T cells. The culture media were collected 48 hours post-transfection. These four (4) deletion proteins were immunoprecipitated using anti-Flag affinity gel. 200 ng of IL-23 cytokine was added to the immunoprecipitation assay. Three (3) of the four (4) deletion proteins were shown to bound to IL-23 cytokine (See, FIG. 18). In contrast, 1-200 mutant failed to bound to IL-23 cytokine. We speculate that the 1-200 mutant may be improperly folded or missing a critical domain that is essential for binding to IL-23 cytokine. Based on these finding, we concluded that the 1-250 amino acids on the extracellular domain of the full length IL-23Rα are necessary and required for the binding to IL-23 cytokine (See, FIG. 18).

Example 11

Human Δ9 and Δ8,9 Proteins Effectively Competed with Full-length Extracellular Domain of IL-23Rα to Bind to IL-23

We developed a competitive ELISA to further examine the ability of the deletion protein mutants (i.e., Δ9, Δ8,9 and 1-250 mutant) to compete (i.e., interfere) the binding of IL-23 cytokine to the full-length extracellular domain of IL-23Rα (See, "Materials & Methods"). Recombinant IL-23Rα-Fc fusion protein from R&D (2 µg/ml) was coated on the ELISA plate. IL-23 cytokine (50 ng) was added in the absence or presence of the deletion protein mutants as competitors.

In the absence of Δ9, Δ8, 9 or 1-250 mutant, IL-23 cytokine effectively bound to the IL-23Rα-Fc fusion protein coated on the plate surface (FIG. 19). In contrast, both Δ9 and Δ8,9 blocked the binding of IL-23 cytokine to the IL-23Rα-Fc fusion protein (FIG. 19). Unlike Δ9 and Δ8,9, 1-250 mutant protein showed no effect on the binding of IL-23 cytokine to the IL-23Rα-Fc fusion protein (FIG. 19). These observations indicate that Δ9, Δ8,9, and 1-250 mutant are capable of binding to IL-23 cytokine. However, only Δ9 and Δ8,9 are capable of competing with the full-length extracellular domain of IL-23Rα. The failure of 1-250 mutant is believed to be due to a weak binding affinity towards IL-23 cytokine.

Example 12

Mammalian-Derived Δ9 is Glycosylated—Role of Glycosylation in Δ9 Functions

The mature form of Δ9 variant comprises some 333 amino acids (i.e., 356 amino acids minus the signal peptide of 23 amino acids), predicting a size of 41 kDa. Its observed size, however, was consistently around 65 kDa (FIG. 4; see also FIG. 6), suggesting post-translational modification, most likely by N-glycosylation, as is common in many cytokine receptors. PNGase F treatment of affinity (FLAG) purified Δ9 reduced its apparent size to below 50 kDa, confirming N-glycosylation in Δ9 protein (FIG. 20) (See "Materials & Methods").

Recombinant IL-23 (200 ng) was added to PNGase F treated or untreated Δ9 in the immunoprecipation reaction. Interestingly, removing the glycosyl component of Δ9 clearly reduced its capacity to bind IL-23 (FIG. 21), indicating an essential role of glycosylation in Δ9 protein function.

Example 13

Human Δ9 Protein Forms A Complex With IL-23 And IL-12Rβ1

On the cell surface, human IL-23Rα combines with human IL-12Rβ1 to form the heterodimeric IL-23 receptor. Human IL12Rβ1 also partners with human IL12Rβ2 to form the cell-surface IL-12 receptor. We wanted to know whether Δ9 could link to human IL-12Rβ1 via IL-23, or indeed bind it directly. Soluble, recombinant HIS-tagged hIL-12Rβ1 (1 μg) was spiked into concentrated FLAG-tagged Δ9-containing 293T supernatant in the presence or absence of IL-23 (200 ng). Immunoprecipation with anti-FLAG was performed and the Western blots analysed with anti-HIS, anti-hIL-12/23p40 or anti-hIL-23Rα to visualize shIL-12Rβ1, the IL-23 p40 subunit or Δ9, respectively. Δ9 does not bind directly to human IL-12Rβ1 (FIG. 22).

However, when IL-23 was added to the binding assay, immunoprecipitation with anti-FLAG allowed visualization of all three reactants: Δ9, IL-23 (p40) and human IL-12Rβ1, indicating that Δ9 forms a complex with human IL-12Rβ1 through binding to IL-23, thus mimicking the cell-surface receptor (FIG. 22).

Example 14

Human Δ9 Protein Modulates the Action of IL-23—Inhibition of Cell Signaling

Next, we tested the ability of Δ9 to interfere with the natural biological functions of human IL-23, in vitro. Signaling through the IL-23 receptor primarily triggers the phosphorylation of STAT3; which is essential to the maturation of Th17 cells. We incubated freshly-isolated human PBMCs with 10 ng/mL IL-23 and examined the phosphorylation of multiple STATs (See "Materials & Methods"). As expected, the greatest influence of IL-23 was on STAT3 (FIG. 23) although some phospho-STAT1 and phospho-STAT5 were also generated. Following titration of IL-23 on STAT3 phosphorylation (FIG. 24), further experiments were conducted with 5 ng/mL IL-23.

In the presence of 5 ng/mL IL-23, phospho-STAT3 was elevated by 4.8 fold; supernatants from 293T-cells transfected with expression construct containing the full-length (wt) IL-23Rα transcript showed a slight enhancement of this (7-fold elevation of phospho-STAT3 compared with no IL-23 added). However, supernatants from 293T cells transfected with the Δ9 expression construct effected a marked reduction of phospho-STAT3, below the level of IL-23 alone, demonstrating a notable inhibition of IL-23's function on human leukocytes (FIG. 25).

To confirm that this inhibition was indeed due to Δ9, we purified recombinant Δ9 protein from the secreted source to apparent homogeneity (FIG. 6) (See Example 5 and "Materials & Methods" for the purification). This purified Δ9 inhibited IL-23-induced STAT3 phosphorylation (FIG. 26), in a dose-dependent manner (FIG. 27). Thus, Δ9 negatively regulates IL-23 signaling in human leukocytes.

Example 15

Human Δ9 Protein Inhibits the Maturation of Th17 Cells a) Maturation of Th17 Cells IL-23 is key to the function of Th17 cells, although by itself it is incapable of inducing the differentiation of these cells in vitro, from a starting population of naive human CD4+ T-cells. However, the ability of Δ9 to inhibit IL-23 signaling suggested that it would also inhibit the functional maturation of human Th17 cells.

We purified human CD3+CD4+CD45RA+ cells ("naive CD4+ T-cells") by negative selection (using magnetic beads coupled with specific bound antibodies against the cell surface markers. FIG. 28 depicts the purity of the isolated cells measured by the Flow Cytometry.

We differentiated the isolated cells to Th17 cells in vitro, using the protocol as illustrated in the FIG. 29. These highly enriched naive CD4+ T-cells were stimulated with anti-CD3/CD28 coated microbeads ("beads") in the presence of a cytokine cocktail comprising IL-1β, IL-6 and TGF-β for two days, at which point medium, IL-23, Δ9 or IL-23+Δ9 were added (See "Material and Method"). Incubation continued for a further two days, whereupon cells were harvested for RNA and supernatants collected for ELISA.

We used the expression levels of the four (4) major T-cell transcription factors as indicator for the T-helper (Th) cell differentiation (i.e. GATA3 (Th1), T-bet (Th2), Foxp3 (Treg) and RoRγt (Th17)). Bead stimulation of naive CD4+ T-cells in the absence of cytokine permitted the expression of these transcription factors, GATA3, T-bet, Foxp3 and RoRγt (FIG. 30). However, in the presence of the "Th17 cocktail", marked skewing in favor of RORγt was observed, indicating the successful differentiation of naive CD4+ T-cells to Th17 cells.

Terminal maturation of the Th17 phenotype by IL-23 was demonstrated by the enhanced expression of IL-17A, IL-17F mRNA in the presence of IL-23 (FIG. 31); as expected, RORγt was not elevated by the addition of IL-23 to the Th17 cocktail, reaffirming that IL-23 is not a human Th17 cell differentiation factor.

b) Δ9 Inhibits IL-17A and IL17F

Addition of Δ9 alone to the Th17 cocktail failed to induce the mRNA expression of IL-17A or IL-17F, confirming its lack of stimulatory activity (FIG. 32).

FIG. 33 depicts that when IL-23 was added in the presence of Δ9, maturation of Th17 cells to an active phenotype was greatly reduced; mRNA expression of both IL-17A and IL-17F being significantly diminished.

FIGS. 34 and 35 depict the secreted level of IL-17A and IL-17F respectively by Th17 cells under different culture conditions.

Materials and Methods

Fragment Size Analysis of Human IL-23Rα (HuIL23Rα) Splice Variants

Purified RNA from mitogen-stimulated PBMCs was reverse-transcribed into cDNA and PCR was carried out with forward primer (5' AATGCTGGGAAGCTCACCTA-CATA 3') (SEQ ID NO: 5) and reverse primer (5' D3-GCT-TGTGTTCTGGGATGAAGATTTC 3') (SEQ ID NO: 6), which was fluorescent labeled with the "D3" dye. The amplified product was denatured and analyzed in the Beckman CEQ8000 using their Fragment Analysis Program, calibrated with DNA size standard marker kit 600 (0.5 µl/reaction; Beckman) and custom-made D1 labeled 600-1200 size marker (1 µl/reaction; Bioventures, Inc). Peaks were assigned to corresponding HuIL23Rα spliced variants based on their size. The fluorescent signal represented the mRNA transcript level.

Construction of Expression Constructs

Human wild-type IL-23Rα was amplified from human peripheral blood mononuclear cells (PBMC)'s cDNA using the following primer pair by Pfx high fidelity DNA polymerase (Invitrogen).

P1 F:
(SEQ ID NO: 7)
CAGGTTGAAAGAGGGAAACAGTCT

C-Flag R:
(SEQ ID NO: 8)
CGAGCTACTTGTCATCGTCGTCCTTGTAATCCTTTTCCAAGAGTGAAATC
CTAATG The amplified PCR product was run on agarose gel and purified using DNA gel purification kit from Qiagen. The gel purified PCR product was cloned into pcDNA3.3 using TOPO TA cloning kit from Invitrogen. The ligated product was transformed into Top10 competent cell (Invitrogen). The transformed competent cells were selected using LB plate containing ampicillin for 16 hours at 37° C. The ampicillin resistant clones were cultured in 2 mL of LB medium with ampicillin for 16 hours at 37° C. DNA was extracted from the bacteria culture using DNA mini-preparation kit from Qiagene. The DNA was then validated by restriction enzyme digestion and sequencing. The confirmed expression construct was used to prepare high quality DNA for transfection using DNA maxi-preparation kit from Qiagene. The purified DNA was quantified by Nano-drop (Thermo Scientific).

The expression constructs of pΔ11, Δ8, Δ9 and Δ8,9 were made by the same approach except using different primer sets described below.

Generation of Expression Constructs

Expression construct of wild-type IL-23R (WT) was generated by PCR using Pfx DNA polymerase (Invitrogen). Forward primer (5' ATGAATCAGGTCACATTCAATG 3') (SEQ ID NO: 11) and reverse primer (5' CTACTTGTCATCGTCGTCCTTGTAATCCTTTTCCAAGAGTGAAATCTATT G 3') (SEQ ID NO: 12) were used to amplify wild-type IL-23R from PBMCs cDNA. The amplified PCR product was treated with Taq polymerase to add 3'-A overhang to each end of PCR. The gel-purified product was then subcloning into mammalian expression plasmid using the pcDNA3.3 TOPO TA Cloning kit from Invitrogen. The correct expression construct was subjected to validation by sequencing.

Constructions of pΔ11, Δ9 and Δ89 expression plasmids were performed using the same method except pcDNA3.3 IL-23R WT was used as PCR template. Difference primer sets were also used as shown in the following:

pΔ11
Forward primer:
(SEQ ID NO: 13)
5' ATGAATCAGGTCACATTCAATG 3'

Reverse primer:
(SEQ ID NO: 14)
5' CTACTTGTCATCGTCGTCCTTGTAATCTCTCTGTAGCATTTTCACAA
CATTGCT 3'

Δ9
Forward primer:
(SEQ ID NO: 15)
5' ATGAATCAGGTCACATTCAATG 3'

Reverse primer:
(SEQ ID NO: 16)
5' CTACTTGTCATCGTCGTCCTTGTAATCACA ATAAGATCCTTCTTTT
AATCCAGAAGTAAGGTGC 3'

Δ8, 9
Forward primer:
(SEQ ID NO: 17)
5' ATGAATCAGGTCACATTCAATG 3'

Reverse primer:
(SEQ ID NO: 18)
5' CTACTTGTCATCGTCGTCCTTGTAATCACA ATAAGATCCTTCTTTT
AATCCTGTTTCAGGTGTT 3'

Construction of Δ8 expression plasmid was performed by PCR overlap extension. Two fragments, fragment 1: Translation start to Exon 7 and fragment 2: Exon 9 to Translation stop, were amplified using the following primer pairs.

Fragment 1
Forward primer:
(SEQ ID NO: 19)
5' ATGAATCAGGTCACATTCAATG 3'

Reverse primer:
(SEQ ID NO: 20)
5' CTGTTTCAGGTGTT 3'

Fragment 2
Forward primer:
(SEQ ID NO: 21)
5' AACACCTGAAACAG 3'

Reverse primer:
(SEQ ID NO: 22)
5' CTACTTGTCATCGTCGTCCTTGTAATCCTTTTCCAAGAGTGAAATCC
TATTG 3'

Two amplified fragments (1 and 2) were then joined together by overlapping extension. The final combined fragment was sub-cloned into pcDNA3.3 TOPO expression vector.

Isolation and Culture of Human PBMCs and Immune Cells

Peripheral blood mononuclear cells were isolated from heparinized whole venous blood of healthy donors by density gradient centrifugation using Ficoll-Paque (Sigma-Aldrich, St Louis, Mo., USA) according to the manufacture's instructions. Blood was purchased as anonymous buffy coats from New Jersey blood transfusion service with no donor identifying details. Isolated PBMCs were maintained in RPMI-1640 medium (Invitrogen-Gibco, Carlsband, Calif., USA) supplemented with 10% heat-inacticated fetal bovine serum (Invitrogen-Gibco) and 1 mM glutamine (Invitrogen-Gibco). Distinct immune cell populations such as B-cells, T-cells, NK-cells and monocytes were positively isolated from PBMCs by EasySep magnet kits (StemCell Technologies). In the stimulation study, isolated PBMCs were recovered for 2 hours at 37° C. in the 10% FBS/RPMI-1640 medium.

Fragment Analysis

PBMCs were cultured for 72 hours and total RNA was isolated by 'Absolutely RNA' miniprep kit (Stratagene) following the manufacturer's instructions. Purified RNA was reverse-transcribed into cDNA using AffinityScript cDNA synthesis kit (Stratagene). PCR was carried out using 'Expand Long Template Enzyme' mix (roche Applied Science) with forward primer (5' AATGCTGGGAAGCTCAC-CTACATA 3') (SEQ ID NO: 23) and reverse primer (5' D3-GCTTGTGTTCTGGGATGAAGATTTC 3') (SEQ ID NO: 24), which was fluorescent labeled with D3 dye. The amplified product was then analyzed in the Beckman CEQ8000 using Fragment Analysis Program. 1 µl (5%) of PCR product was denatured in 39 µl of SLS buffer (Beckman) containing DNA standard size markers. Two DNA standard size markers, DNA size standard marker kit 600 (0.5 µl/reaction) (Beckman) and custom made D1 labeled 600-1200 size marker (1 µl/reaction) (Bioventures, Inc) were used in to cover the DNA size from 60 to 1200 nucleotides.

Transfection

T cells were plated at around 60-80% confluence 16 hours before transfection. 2 µg (1 well in 6 well plate) or 10 µg (10 cm plate) of DNA was diluted in 100 µl (1 well in 6 well plate) or 500 µl (10 cm plate) of Opti-MEM (Invitrogen). FuGENE HD (Roche) was added to the diluted DNA at concentration of 4 µl per 1 µg of DNA. The mixture was then incubated at room temperature for 15 minutes to allow the DNA complex formation. After incubation, the mixture was added to the culture medium. The transfected cells were then analyzed after 36-48 hours.

Purification of Δ9 Protein

Expression construct of Δ9 gene was transiently transfected into 293T cells by Fugene HD transfection reagent (Roche applied science). The culture medium from the transfected cells was collected and then concentrated using Amicon ultra centrifugal filter 30K (Millipore). C-terminal flag-tagged Δ9 protein was immuno-precipitated from the concentrated medium using anti-flag M2 affinity gel (Sigma) according to the manufacture's instructions. The precipitated Δ9 protein was eluted by excessive Flag peptide (Sigma). The quality and quantity of purified Δ9 were measured by PAGE gels (Bio-rad) stained with Coomassie Blue (Bio-rad).

Western Blotting Analysis

Cells were collected, washed in PBS and lysed in ProteoJET mammalian cell lysis reagent (Fermentas) with protease and phosphatase inhibitors (Sigma). Lysates were centrifuged and supernatants were prepared for SDS-PAGE by addition of sample loading buffer (Bio-Rad). Lysates were subjected to 4-12% PAGE (Bio-Rad) and transferred to Immun-Blot PVDF membrane (Bio-Rad) per manufacturer's recommendations. Membranes were blocked in 5% milk/TPBT at room temperature for 1 hour. Membranes were first probed with antibodies against p-STAT1, p-STAT2, p-STAT3 or p-STAT5 (cell signaling technology), and then stripped and reprobed for STAT1, STAT2, STAT3 or STAT5 (cell signaling technology).

Real-Time PCR

Naive T-cells were differentiated under TH-17 condition for 5 days. Differentiated cells were collected and RNA was extracted by Trizol (Invitrogen). RNA was reverse transcribed into cDNA by AffinityScript QPCR cDNA Synthesis Kit (Stratagene) according to the manufacture's instructions. The real-time PCR was performed using Brilliant II SYBR Green QPCR Master Mix (Stratagene). The following primers were used in the study: T-bet: F 5' CGTCCA ACA ATGTGACCCAGATG 3' (SEQ ID NO: 25), R 5'GGTAG-GCAGTCACGGCAATGA AC 3' (SEQ ID NO: 26); Foxp3: F 5' GACCAAGGCTTCATCTGTGGCATC 3' (SEQ ID NO: 27), R 5' GCTGTTTCCATGGCTACCCCAC 3' (SEQ ID NO: 28); GATA-3: F 5' GTCCTGTGCGAACT-GTCAGA 3' (SEQ ID NO: 29), R 5' CTGGATGCCTTC-CTTCTTCA 3' (SEQ ID NO: 30);

RORγT: F 5' GCTGGCCTTTCATCATCATC 3' (SEQ ID NO: 31), R 5' CTTTCCACATGCTGGCTACA 3' (SEQ ID NO: 32);

IL-17A: F 5' CTGGGAAGACCTCATTGGTGTCAC 3' (SEQ ID NO: 33), R 5' CGGTTATGGATGTTCAGGTT-GACC 3' (SEQ ID NO: 34); IL-17F: F 5' CCTCCCCCTG-GAATTACACTGTC 3' (SEQ ID NO: 35), R 5'CAGGGTCTCTTGCTGGATGGG 3' (SEQ ID NO: 36);

IL-21: F 5' GTTGATCAGCTGAAAAATTATGTGAAT-GAC 3' (SEQ ID NO: 37), R 5' GCAGGAAAAAGCTGAC-CACTCACAG 5' (SEQ ID NO: 38); GAPDH: F 5' GAGT-CAACGGATTTGGTCGT 3' (SEQ ID NO: 39), R 5' GACAAGCTTCCCGTTCTCAG 3' (SEQ ID NO: 40).

In Vitro Binding Assay

Recombinant proteins, including IL-23 (200 ng, humanzyme), IL-12 (200 ng, humanzyme) or soluble IL-12Rβ1 (1 µg, R&D), were added to the concentrated culture media from 293T cell transfected with empty vector or Δ9 expression construct. Δ9 protein was immuno-precipitated by Anti-Flag M2 affinity gel (Sigma). Precipitated proteins were eluted by addition of excessive Flag-peptide (Sigma) and separated by SDS-PAGE (Bio-rad). Anti-IL-12/23 p40 (R&D) and Anti-His tag (Invitrogen) were used to detect IL-12/IL-23 and IL-12Rβ1 respectively in the immunoblot assay.

Glycosylation modification on Δ9 protein was removed by PNGase F treatment (NEB) according to the manufacture's instructions. Recombinant IL-23 (200 ng) was added to the treated and untreated Δ9 protein followed by immunoprecipitation using Anti-Flag M2 affinity gel (Sigma). Anti-IL-12/23 p40 was used in the immunoblot to detect recombinant IL-23.

Transfection of 293T Cells

One day before the transfection experiment, 293T cells were trypsinized and cultured on the 10-cm culture plate. The cell density was at around 80% confluency at the time of transfection. 10 µg of DNA was mixed with 500 µl of OptiMEM (Invitrogen). 40 µl of FuGene HD transfection reagent (Roche) was diluted in 500 µl of OptiMEM. The diluted transfection reagent was then added to DNA mix and vortex for two seconds to mix the contents. The mixture was incubated at room temperature for 15 minutes before addition to the 293T cells. Both culture media and cell lysates were prepared after 48 hours post-transfection for purification of Δ9 protein.

Purification of Intracellular Δ9 Protein

Cells were collected, washed in PBS and lysed in ProteoJET mammalian cell lysis reagent (Fermentas) with protease and phosphatase inhibitors (Sigma). Lysates were centrifuged and supernatants were prepared for purification. C-terminal flag-tagged Δ9 was immuno-precipitated from cellular lysates using anti-flag M2 affinity gel (Sigma) according to the manufacture's instructions. The precipitated Δ9 was eluted by excessive Flag peptide (Sigma). The quality and quantity of the purified Δ9 were measured by PAGE gels (Bio-Rad) and stained with Coomassie Blue (Bio-Rad).

Purification of Δ9 Protein from Culture Medium

The purification of Δ9 protein from culture medium was the same as that of the intracellular Δ9, except the concentrated cultured media were used. The culture medium from the transfected cells was first collected and then concentrated using Amicon ultra centrifugal filter 30K (Millipore). The purification steps of Δ9 include:
(1) Transfecting Δ9 expression construct into 293T cells;
(2) Collecting culture media after 48 hours, 72 hours or 96 hours post-transfection;
(3) Centrifuging to remove dead cells and unattached cells;
(4) Concentrating culture media using Amicon Ultra-15 Centrifugal Filter with 30 kda cutoff;
(5) Immuno-precipitating Δ9 by anti-Flag M2 Affinity Gel;
(6) Eluting Δ9 by excessive Flag peptides; and
(7) Measuring the quantity and purity of purified Δ9 by gel electrophoresis and Coomassie Blue staining.

Immunoblot Assay (Western Blotting)

Cells were collected, washed in PBS and lysed in ProteoJET mammalian cell lysis reagent (Fermentas) with protease and phosphatase inhibitors (Sigma). Lysates were centrifuged and supernatants were prepared for SDS-PAGE by addition of sample loading buffer (Bio-Rad). Lysates were subjected to 4-12% PAGE (Bio-Rad) and transferred to Immun-Blot PVDF membrane (Bio-Rad) per manufacturer's recommendations. Membranes were blocked in 5% milk/TPBT at room temperature for 1 hour. Membranes were probed with anti-FLAG (sigma), mouse anti-human IL-23Rα (R&D) and biotinlyated goat anti-human IL-23Rα (R&D).

Expression and Detection of Δ9.

Expression constructs for both wt HuIL23Rα and Δ9 spliced variant were prepared. cDNA of each form was subcloned into pcDNA3.3 TOPO vector, using the TA cloning kit from Invitrogen (Carlsbad Calif.). Both forms were tagged with the "FLAG" sequence at the C-terminus and 293T cells were transiently transfected. Cell lysates and culture media were harvested after 48 hours and immunoblotted using Anti-FLAG M2 antibody. To measure the level of soluble hIL-23Rα (Δ9), a sandwich ELISA was developed using mouse anti-hIL-23R/Fc and biotinlyated goat anti-hIL-23Rα, and calibrated with IL-23R/Fc fusion protein (R&D Systems). The ELISA was validated against conditioned media from two independent transfection experiments. Plasma samples from healthy human with no history of Crohn's disease were obtained either purchased from the Innovative Research (Michigan) or collected from volunteers. Plasma from ten (10) Crohn's patients was obtained from Asterand.

Biochemical Properties of Δ9 Protein

Culture medium from Δ9 transfection experiments was concentrated using Amicon ultra centrifugal filter 30K (Millipore), then Δ9 protein was affinity purified using anti-FLAG M2 affinity gel (Sigma). The immuno-complex was precipitated, washed and resuspended in PBS. 200 ng of either IL-12 or IL-23 was added to the suspension and incubated at 4° C. for 2 hours. Reprecipitated FLAG-tagged Δ9 immuno-complex was again precipitated and eluted with excess FLAG peptide. The eluted product was analysed by immunoblot using anti-human p40 or anti-human IL-23R to detect the common p40 subunit of IL-12/IL-23 or Δ9, respectively. In some cases, recombinant human His-tagged soluble IL-12Rβ1 (1 μg/reaction; R&D Systems) was spiked into the suspension containing Δ9 bound to anti-FLAG M2 affinity gel, in the presence or absence of 200 ng IL-23. After extensive washing, the eluted product was analysed using anti-HIS (Invitrogen, Carlsbad Calif.), anti-human p40 or anti-human IL-23R(R&D Systems) to detect soluble IL-12Rβ1, the p40 subunit of IL-23 or Δ9, respectively. To examine the N-glycosylation modification on soluble human IL-23Rα, purified Δ9 was treated with N-Glycosidase F (PNGase F) at 37° C. for 1 hour followed by immunoblotting using anti-human IL-23R. Recombinant IL-23 (200 ng) was added to Δ9 protein or PNGase F-treated Δ9 protein. Immuno-precipitation was performed and analysed by immunoblot, probing with anti-hIL-12/23p40.

Competitive ELISA

To determine if our recombinant proteins (Δ9, Δ8,9 and 1-250) could inhibit the binding of IL-23 to IL-23R, competitive ELISA was developed.

Recombinant human IL-23R-$F_c$ (2 μg/ml) (from R&D) was coated onto plates as a capture reagent. Biotinylated anti-p40 antibody (1:250) (which specifically recognizes the p40 subunit of IL-23) was used as a detection antibody. Streptavidin—horseradish peroxidase (HRP) (1:500) was added to detect the biotinlyated anti-p40 antibody. The peroxidase activity (representing the level of IL-23 captured onto plates) was measured by addition of a tetramethylbenzidine (TMB) substrate (100 μl/well). The color intensity was directly proportion to the amount of the bound IL-23 protein. The color was measured at optical density (OD) 450 nm using a microtiter plate reader.

Δ9 and IL-23 Signaling in Human PBMC

Peripheral blood mononuclear cells (PBMCs) were isolated from heparinised whole venous blood of healthy donors by density gradient centrifugation using Ficoll-Paque (Sigma-Aldrich, St Louis, Mo., USA). Blood was purchased as anonymous buffy coats from New Jersey blood transfusion service. Isolated PBMCs were rested in RPMI-1640 medium (Invitrogen-Gibco, Carlsbad, Calif.) supplemented with 10% heat-inactivated foetal bovine serum (Invitrogen-Gibco) and 1 mM glutamine (Invitrogen-Gibco) at 37° C. for 24 hours. PBMCs were then stimulated with 10 ng/mL IL-23 for 20 mins. Cell lysates were prepared for immunoblots to examine the phosphorylation status of STATs. Membranes were probed with antibodies against p-STAT1, p-STAT2, p-STAT3 or p-STAT5 (Cell Signaling Technology), then stripped and reprobed for total STAT1, STAT2, STAT3 or STAT5 (Cell Signaling Technology). In some cases PBMC were stimulated in the presence of supernatant containing human IL23RαΔ9 protein, titrated as shown.

Purification of Δ9 Protein

T cell supernatant containing FLAG-tagged HuIL23RαΔ9 protein was collected and concentrated using Amicon ultra centrifugal filter 30K (Millipore), then precipitated using anti-FLAG M2 affinity gel (Sigma). Precipitated Δ9 was eluted with excess FLAG peptide (Sigma). 10 μl of purified Δ9 was used in the PAGE gels (Bio-Rad), followed by Coomassie Blue (Bio-Rad) staining.

Differentiation of Human Th17 Cells.

Naive $CD4^+$ human T-cells were obtained by negative enrichment (StemCell Technologies, Vancouver). Their purity was assessed by Flow cytometry. Of the 96% $CD4^+$ T-cells prepared, 98% were $CD45RA^+$, $CD45R0^-$. $CD4^+$ naive T-cells were cultured for 5 days under the influence of anti-$CD3^+$ anti-CD28 and a "Th-17 differentiation" cytokine cocktail (10 ng/mL of IL-1, 10 ng/mL of IL-6 and 1 ng/mL of TGF-β) in the presence of 5 ng/mL of IL-23, 500 ng/mL of Δ9 or IL-23/Δ9 complex. Th17 differentiation was assessed by measuring the mRNA transcript levels of four crucial transcription factors (T-bet, GATA-3, Foxp3 and RORγt). In some cases as shown, IL-17A and IL-17F were quantitated by ELISA (R&D Systems).

ELISA

Sandwich ELISA was developed using 5 µg/ml of mouse anti-human IL-23R(R&D) as capture antibody and 1.6 µg/ml of Goat biotinlyated anti-human IL-23R(R&D) as detection antibody. Capture antibody was first coated on the microtiter plate using 50 mM of bicarbonate buffer (pH=9.6) at 4° C. overnight. The plate was then blocked with 10% FBS/TBST at room temperature for 2 hours. Samples were added to the well and incubated at 4° C. overnight. Detection antibody in TBST was added to the wells and incubated at room temperature for 2 hours. The plate was extensively washed with TBST during each change. The immunocomplex was detected by addition of Streptavidin-HRP (R&D) and TMB substrate (eBioscience). The plate was read at $OD_{450\,nm}$.

While the present invention has been described in connection with specific embodiments thereof, it will be understood that it is capable of further modifications and this application is intended to cover any variations of the invention thereof. One of skill in the art will recognize that various modifications may be made to the embodiments described herein without departing from the spirit and scope of the invention, which is defined by the appended claims. All the references and patents cited in this application are incorporated by reference in their entirety.

REFERENCES

1. Langrish C L, Chen Y, Blumenschein W M et al. IL-23 drives a pathogenic T cell population that induces autoimmune inflammation. *J Exp Med.* 2005; 201:233-240.
2. Harrington L E, Hatton R D, Mangan P R et al. Interleukin 17-producing CD4+ effector T cells develop via a lineage distinct from the T helper type 1 and 2 lineages. *Nat. Immunol.* 2005; 6:1123-1132.
3. Oppmann B, Lesley R, Blom B et al. Novel p19 protein engages IL-12p40 to form a cytokine, IL-23, with biological activities similar as well as distinct from IL-12. *Immunity.* 2000; 13:715-725.
4. Parham C, Chirica M, Timans J et al. A receptor for the heterodimeric cytokine IL-23 is composed of IL-12Rbeta1 and a novel cytokine receptor subunit, IL-23R. *J. Immunol.* 2002; 168:5699-5708.
5. Aggarwal S, Ghilardi N, Xie M H, de Sauvage F J, Gurney A L. Interleukin-23 promotes a distinct CD4 T cell activation state characterized by the production of interleukin-17. *J Biol. Chem.* 2003; 278:1910-1914.
6. Yang X O, Panopoulos A D, Nurieva R et al. STAT3 regulates cytokine-mediated generation of inflammatory helper T cells. *J Biol. Chem.* 2007; 282:9358-9363.
7. Korn T, Oukka M, Kuchroo V, Bettelli E. Th17 cells: effector T cells with inflammatory properties. *Semin Immunol.* 2007; 19:362-371.
8. Ouyang W, Kolls J K, Zheng Y. The biological functions of T helper 17 cell effector cytokines in inflammation. *Immunity.* 2008; 28:454-467.
9. Louten J, Boniface K, de Waal Malefyt R. Development and function of TH17 cells in health and disease. *J Allergy Clin Immunol.* 2009; 123:1004-1011.
10. Mangan P R, Harrington L E, O'Quinn D B et al. Transforming growth factor-beta induces development of the T(H)17 lineage. *Nature.* 2006; 441:231-234.
11. Veldhoen M, Hocking R J, Atkins C J, Locksley R M, Stockinger B. TGFbeta in the context of an inflammatory cytokine milieu supports de novo differentiation of IL-17-producing T cells. *Immunity.* 2006; 24:179-189.
12. Wei L, Laurence A, Elias K M, O'Shea J J. IL-21 is produced by Th17 cells and drives IL-17 production in a STAT3-dependent manner. *J Biol. Chem.* 2007; 282: 34605-34610.
13. Zhou L, Ivanov I I, Spolski R et al. IL-6 programs T(H)-17 cell differentiation by promoting sequential engagement of the IL-21 and IL-23 pathways. *Nat. Immunol.* 2007; 8:967-974.
14. Ivanov I I, McKenzie B S, Zhou L et al. The orphan nuclear receptor RORgammat directs the differentiation program of proinflammatory IL-17+ T helper cells. *Cell.* 2006; 126:1121-1133.
15. Yang X O, Pappu B P, Nurieva R et al. T helper 17 lineage differentiation is programmed by orphan nuclear receptors ROR alpha and ROR gamma. *Immunity.* 2008; 28:29-39.
16. Abraham C, Cho J. Interleukin-23/Th17 pathways and inflammatory bowel disease. *Inflamm Bowel Dis.* 2009; 15:1090-1100.
17. Wakashin H, Hirose K, Iwamoto I, Nakajima H. Role of IL-23-Th17 cell axis in allergic airway inflammation. *Int Arch Allergy Immunol.* 2009; 149 Suppl 1:108-112.
18. Chan J R, Blumenschein W, Murphy E et al. IL-23 stimulates epidermal hyperplasia via TNF and IL-20R2-dependent mechanisms with implications for psoriasis pathogenesis. *J Exp Med.* 2006; 203:2577-2587.
19. Murphy C A, Langrish C L, Chen Y et al. Divergent pro- and antiinflammatory roles for IL-23 and IL-12 in joint autoimmune inflammation. *J Exp Med.* 2003; 198:1951-1957.
20. Wong C K, Lit L C, Tam L S, Li E K, Wong P T, Lam C W. Hyperproduction of IL-23 and IL-17 in patients with systemic lupus erythematosus: implications for Th17-mediated inflammation in auto-immunity. *Clin Immunol.* 2008; 127:385-393.
21. Cardoso C R, Garlet G P, Crippa G E et al. Evidence of the presence of T helper type 17 cells in chronic lesions of human periodontal disease. *Oral Microbiol Immunol.* 2009; 24:1-6.
22. Elson C O, Cong Y, Weaver C T et al. Monoclonal anti-interleukin 23 reverses active colitis in a T cell-mediated model in mice. *Gastroenterology.* 2007; 132: 2359-2370.
23. Duerr R H, Taylor K D, Brant S R et al. A genome-wide association study identifies IL23R as an inflammatory bowel disease gene. *Science.* 2006; 314:1461-1463.
24. Cargill M, Schrodi S J, Chang M et al. A large-scale genetic association study confirms IL12B and leads to the identification of IL23R as psoriasis-risk genes. *Am J Hum Genet.* 2007; 80:273-290.
25. Farago B, Magyari L, Safrany E et al. Functional variants of interleukin-23 receptor gene confer risk for rheumatoid arthritis but not for systemic sclerosis. *Ann Rheum Dis.* 2008; 67:248-250.
26. Kan S H, Mancini G, Gallagher G. Identification and characterization of multiple splice forms of the human interleukin-23 receptor alpha chain in mitogen-activated leukocytes. *Genes Immun.* 2008; 9:631-639.
27. Mancini G, Kan S H, Gallagher G. A novel insertion variant of the human IL-23 receptor-alpha chain transcript. *Genes Immun.* 2008; 9:566-569.
28. Presky D H, Yang H, Minetti L J et al. A functional interleukin 12 receptor complex is composed of two beta-type cytokine receptor subunits. *Proc Natl Acad Sci USA.* 1996; 93:14002-14007.

29. Cua D J, Sherlock J, Chen Y et al. Interleukin-23 rather than interleukin-12 is the critical cytokine for autoimmune inflammation of the brain. *Nature*. 2003; 421:744-748.
30. Murphy K M, Reiner S L. The lineage decisions of helper T cells. *Nat Rev Immunol*. 2002; 2:933-944.
31. Liang S C, Tan X Y, Luxenberg D P et al. Interleukin (IL)-22 and IL-17 are coexpressed by Th17 cells and cooperatively enhance expression of antimicrobial peptides. *J Exp Med*. 2006; 203:2271-2279.
32. Harrington L E, Mangan P R, Weaver C T. Expanding the effector CD4 T-cell repertoire: the Th17 lineage. *Curr Opin Immunol*. 2006; 18:349-356.
33. Fujino S, Andoh A, Bamba S et al. Increased expression of interleukin 17 in inflammatory bowel disease. *Gut*. 2003; 52:65-70.
34. Zheng Y, Danilenko D M, Valdez P et al. Interleukin-22, a T(H)17 cytokine, mediates IL-23-induced dermal inflammation and acanthosis. *Nature*. 2007; 445:648-651.

What is claimed is:

1. A pharmaceutical composition useful in inhibiting IL-23R mediated cell signaling, comprising a recombinant IL-23Rα protein, said recombinant IL-23Rα protein consists of the amino acid sequence of SEQ ID NO: 4, and a pharmaceutical acceptable excipient.

2. The pharmaceutical composition of claim 1, wherein said pharmaceutical composition is a solid form selected from the group consisting of pills, capsules, granules, tablets and powders.

3. The pharmaceutical composition of claim 1, wherein said pharmaceutical composition is a liquid form selected from the group consisting of solutions, syrups, elixirs and suspensions.

4. The pharmaceutical composition of claim 1, wherein said pharmaceutical composition is a parenteral form.

5. The pharmaceutical composition of claim 1, wherein said pharmaceutical composition is a nasal form.

6. The pharmaceutical composition of claim 1, wherein said recombinant IL-23Rα is prepared by the steps of:
   a) transfecting a cell with a vector containing a gene consisting of the nucleotide sequence of SEQ ID NO: 3;
   b) allowing said transfected cell to produce said recombinant IL-23Rα protein; and
   c) isolating said recombinant IL-23Rα protein.

7. The pharmaceutical composition of claim 6, wherein said cell is selected from the group consisting of 293T, CHO and COS.

8. The pharmaceutical composition of claim 6, wherein said cell is 293T cell.

9. The pharmaceutical composition of claim 6, wherein said vector is selected from the group consisting of pcDNA 3.3.Topo, pcDNA 3.1, pCI, pSI, pTARhET, pPMR and pTK-Hyg.

10. The pharmaceutical composition of claim 6, wherein said vector is pcDNA 3.3.

11. The pharmaceutical composition of claim 6, wherein said isolating step c) is performed using ion-exchange column, reverse phase HPLC, chromatography on silica, cation-exchange resin, chromatofocusing, SDS-PAGE, ammonium sulfate, metal chelating column, or antibody column.

12. The pharmaceutical composition of claim 6, wherein said isolating step c) is performed using an antibody column.

13. The pharmaceutical composition of claim 6, wherein said isolating step c) is performed using an anti-FLAG column.

14. A method of preparing a pharmaceutical composition containing a recombinant IL-23Rα protein, said recombinant IL-23Rα protein consists of the amino acid sequence of SEQ ID NO: 4, comprising the steps of:
   a) preparing a recombinant IL-23Rα protein consisting of the amino acid sequence of SEQ ID NO: 4, said preparing step is performed by the steps of:
      (i) transfecting a cell with a vector containing a gene, said gene consists of the nucleic acid sequence of SEQ ID NO: 3;
      (ii) allowing said transfected cell to produce said recombinant IL-23Rα protein; and
      (iii) isolating said recombinant IL-23Rα protein; and
   b) constituting said recombinant IL-23Rα protein with a pharmaceutically acceptable excipient to form a pharmaceutical composition.

* * * * *

SEQUENCE LISTING

```
<160> NUMBER OF SEQ ID NOS: 41

<210> SEQ ID NO 1
<211> LENGTH: 1071
<212> TYPE: DNA
<213> ORGANISM: Homo sapiens

<400> SEQUENCE: 1
atgaatcagg tcactattca atgggatgca gtaatagccc tttacatact cttcagctgg      60
tgtcatggag gaattacaaa tataaactgc tctggccaca tctgggtaga accagccaca     120 attttttaaga tgggtatgaa tatctctata tattgccaag cagcaattaa gaactgccaa     180
ccaaggaaac ttcatttttta taaaaatggc atcaaagaaa gatttcaaat cacaaggatt    240
aataaaacaa cagctcggct ttggtataaa aactttctgg aaccacatgc ttctatgtac    300
tgcactgctg aatgtcccaa acattttcaa gagacactga tatgtggaaa agacatttct    360
tctggatatc cgccagatat tcctgatgaa gtaacctgtg tcatttatga atattcaggc    420
aacatgactt gcacctggaa tgctgggaag ctcacctaca tagacacaaa atacgtggta    480
catgtgaaga gtttagagac agaagaagag caacagtatc tcacctcaag ctatattaac    540
atctccactg attcattaca aggtggcaag aagtacttgg tttgggtcca agcagcaaac    600
gcactaggca tggaagagtc aaaacaactg caaattcacc tggatgatat agtgatacct    660
tctgcagccg tcatttccag ggctgagact ataaatgcta cagtgcccaa gaccataatt    720
tattgggata gtcaaacaac aattgaaaag gtttcctgtg aaatgagata caaggctaca    780
acaaaccaaa cttggaatgt taaagaattt gacaccaatt ttacatatgt gcaacagtca    840
gaattctact tggagccaaa cattaagtac gtatttcaag tgagatgtca agaaacaggc    900
aaaaggtact ggcagccttg gagttcactg tttttttcata aaacacctga acagttccc     960 caggtcacat caaaagcatt ccaacatgac acatggaatt ctgggctaac agttgcttcc   1020
atctctacag ggcaccttac ttctggatta aagaaggat cttattgtta a              1071

<210> SEQ ID NO 2
<211> LENGTH: 356
<212> TYPE: PRT
<213> ORGANISM: Homo sapiens

<400> SEQUENCE: 2

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
                20                  25                  30

His Ile Trp Val Glu Pro Ala Thr Ile Phe Lys Met Gly Met Asn Ile
            35                  40                  45

Ser Ile Tyr Cys Gln Ala Ala Ile Lys Asn Cys Gln Pro Arg Lys Leu
        50                  55                  60
```

His Phe Tyr Lys Asn Gly Ile Lys Glu Arg Phe Gln Ile Thr Arg Ile
 65                  70                  75                  80

Asn Lys Thr Thr Ala Arg Leu Trp Tyr Lys Asn Phe Leu Glu Pro His
                 85                  90                  95

Ala Ser Met Tyr Cys Thr Ala Glu Cys Pro Lys His Phe Gln Glu Thr
            100                 105                 110

Leu Ile Cys Gly Lys Asp Ile Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Glu Gln Tyr Leu Thr Ser
                165                 170                 175

Ser Tyr Ile Asn Ile Ser Thr Asp Ser Leu Gln Gly Gly Lys Lys Tyr
                180                 185                 190

Leu Val Trp Val Gln Ala Ala Asn Ala Leu Gly Met Glu Glu Ser Lys
            195                 200                 205

Gln Leu Gln Ile His Leu Asp Asp Ile Val Ile Pro Ser Ala Ala Val
210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Gly Leu Lys Glu
            340                 345                 350

Gly Ser Tyr Cys
        355

<210> SEQ ID NO 3
<211> LENGTH: 981
<212> TYPE: DNA
<213> ORGANISM: Homo sapiens

<400> SEQUENCE: 3
atgaatcagg tcactattca atgggatgca gtaatagccc tttacatact cttcagctgg      60
tgtcatggag gaattacaaa tataaactgc tctggccaca tctgggtaga accagccaca     120
attttaagat gggtatgaa tatctctata tattgccaag cagcaattaa gaactgccaa     180
ccaaggaaac ttcattttta taaaaatggc atcaaagaaa gatttcaaat cacaaggatt     240
aataaaacaa cagctcggct tggtataaaa actttctgg aaccacatgc ttctatgtac     300
tgcactgctg aatgtcccaa acattttcaa gagacactga tatgtggaaa agacatttct     360
tctggatatc cgccagatat tcctgatgaa gtaacctgtg tcatttatga atattcaggc     420

```
aacatgactt gcacctggaa tgctgggaag ctcacctaca tagacacaaa atacgtggta    480
catgtgaaga gtttagagac agaagaagag caacagtatc tcacctcaag ctatattaac    540
atctccactg attcattaca aggtggcaag aagtacttgg tttgggtcca agcagcaaac    600
gcactaggca tggaagagtc aaaacaactg caaattcacc tggatgatat agtgatacct    660
tctgcagccg tcatttccag ggctgagact ataaatgcta cagtgcccaa gaccataatt    720
tattgggata gtcaaacaac aattgaaaag gtttcctgtg aaatgagata caaggctaca    780
acaaaccaaa cttggaatgt taagaatttt gacaccaatt ttacatatgt gcaacagtca    840
gaattctact tggagccaaa cattaagtac gtatttcaag tgagatgtca agaaacaggc    900
aaaaggtact ggcagccttg gagttcactg ttttttcata aaacacctga acaggatta    960 aaagaaggat cttattgtta a                                              981
```

```
<210> SEQ ID NO 4
<211> LENGTH: 326
<212> TYPE: PRT
<213> ORGANISM: Homo sapiens

<400> SEQUENCE: 4
```

```
Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Tyr Leu Thr Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270
```

-continued

```
Asn Phe Thr Tyr Val Gln Gln Ser Glu Phe Tyr Leu Glu Pro Asn Ile
            275                 280                 285

Lys Tyr Val Phe Gln Val Arg Cys Gln Glu Thr Gly Lys Arg Tyr Trp
        290                 295                 300

Gln Pro Trp Ser Ser Leu Phe Phe His Lys Thr Pro Glu Thr Gly Leu
305                 310                 315                 320

Lys Glu Gly Ser Tyr Cys
                325

<210> SEQ ID NO 5
<211> LENGTH: 24
<212> TYPE: DNA
<213> ORGANISM: Homo sapiens
<220> FEATURE:
<223> OTHER INFORMATION: Primer

<400> SEQUENCE: 5
aatgctggga agctcaccta cata                                           24

<210> SEQ ID NO 6
<211> LENGTH: 25
<212> TYPE: DNA
<213> ORGANISM: Homo sapiens
<220> FEATURE:
<223> OTHER INFORMATION: Primer

<400> SEQUENCE: 6
gcttgtgttc tgggatgaag atttc                                          25

<210> SEQ ID NO 7
<211> LENGTH: 24
<212> TYPE: DNA
<213> ORGANISM: Homo sapiens
<220> FEATURE:
<223> OTHER INFORMATION: Primer

<400> SEQUENCE: 7
caggttgaaa gagggaaaca gtct                                           24

<210> SEQ ID NO 8
<211> LENGTH: 56
<212> TYPE: DNA
<213> ORGANISM: Homo sapiens
<220> FEATURE:
<223> OTHER INFORMATION: Primer

<400> SEQUENCE: 8
cgagctactt gtcatcgtcg tccttgtaat ccttttccaa gagtgaaatc ctaatg        56

<210> SEQ ID NO 9
<211> LENGTH: 8
<212> TYPE: PRT
<213> ORGANISM: Homo sapiens

<400> SEQUENCE: 9

Gly Leu Lys Glu Gly Ser Tyr Cys
1               5

<210> SEQ ID NO 10
<211> LENGTH: 5
<212> TYPE: PRT
<213> ORGANISM: Homo sapiens

<400> SEQUENCE: 10
```

Asp Asn Arg Gly Asp
1               5

<210> SEQ ID NO 11
<211> LENGTH: 22
<212> TYPE: DNA
<213> ORGANISM: Homo sapiens
<220> FEATURE:
<223> OTHER INFORMATION: Primer

<400> SEQUENCE: 11
atgaatcagg tcacattcaa tg                                              22

<210> SEQ ID NO 12
<211> LENGTH: 52
<212> TYPE: DNA
<213> ORGANISM: Homo sapiens
<220> FEATURE:
<223> OTHER INFORMATION: Primer

<400> SEQUENCE: 12
ctacttgtca tcgtcgtcct tgtaatcctt ttccaagagt gaaatcctat tg             52

<210> SEQ ID NO 13
<211> LENGTH: 22
<212> TYPE: DNA
<213> ORGANISM: Homo sapiens
<220> FEATURE:
<223> OTHER INFORMATION: Primer

<400> SEQUENCE: 13
atgaatcagg tcacattcaa tg                                              22

<210> SEQ ID NO 14
<211> LENGTH: 54
<212> TYPE: DNA
<213> ORGANISM: Homo sapiens
<220> FEATURE:
<223> OTHER INFORMATION: Primer

<400> SEQUENCE: 14
ctacttgtca tcgtcgtcct tgtaatctctctgtagcatt ttcacaacat tgct            54

<210> SEQ ID NO 15
<211> LENGTH: 22
<212> TYPE: DNA
<213> ORGANISM: Homo sapiens
<220> FEATURE:
<223> OTHER INFORMATION: Primer

<400> SEQUENCE: 15
atgaatcagg tcacattcaa tg                                              22

<210> SEQ ID NO 16
<211> LENGTH: 64
<212> TYPE: DNA
<213> ORGANISM: Homo sapiens
<220> FEATURE:
<223> OTHER INFORMATION: Primer

<400> SEQUENCE: 16
ctacttgtca tcgtcgtcct tgtaatcaca ataagatcct tcttttaatc cagaagtaag     60
gtgc                                                                  64

<210> SEQ ID NO 17
<211> LENGTH: 22

```
<212> TYPE: DNA
<213> ORGANISM: Homo sapiens
<220> FEATURE:
<223> OTHER INFORMATION: Primer

<400> SEQUENCE: 17
atgaatcagg tcacattcaa tg                                              22

<210> SEQ ID NO 18
<211> LENGTH: 64
<212> TYPE: DNA
<213> ORGANISM: Homo sapiens
<220> FEATURE:
<223> OTHER INFORMATION: Primer

<400> SEQUENCE: 18
ctacttgtca tcgtcgtcct tgtaatcaca ataagatcct tcttttaatc ctgtttcagg     60
tgtt                                                                  64

<210> SEQ ID NO 19
<211> LENGTH: 22
<212> TYPE: DNA
<213> ORGANISM: Homo sapiens
<220> FEATURE:
<223> OTHER INFORMATION: Primer

<400> SEQUENCE: 19
atgaatcagg tcacattcaa tg                                              22

<210> SEQ ID NO 20
<211> LENGTH: 14
<212> TYPE: DNA
<213> ORGANISM: Homo sapiens
<220> FEATURE:
<223> OTHER INFORMATION: Primer

<400> SEQUENCE: 20
ctgtttcagg tgtt                                                       14

<210> SEQ ID NO 21
<211> LENGTH: 14
<212> TYPE: DNA
<213> ORGANISM: Homo sapiens
<220> FEATURE:
<223> OTHER INFORMATION: Primer

<400> SEQUENCE: 21
aacacctgaa acag                                                       14

<210> SEQ ID NO 22
<211> LENGTH: 52
<212> TYPE: DNA
<213> ORGANISM: Homo sapiens
<220> FEATURE:
<223> OTHER INFORMATION: Primer

<400> SEQUENCE: 22
ctacttgtca tcgtcgtcct tgtaatcctt ttccaagagt gaaatcctat tg             52

<210> SEQ ID NO 23
<211> LENGTH: 24
<212> TYPE: DNA
<213> ORGANISM: Homo sapiens
<220> FEATURE:
<223> OTHER INFORMATION: Primer
```

```
<400> SEQUENCE: 23
aatgctggga agctcaccta cata                                          24

<210> SEQ ID NO 24
<211> LENGTH: 25
<212> TYPE: DNA
<213> ORGANISM: Homo sapiens
<220> FEATURE:
<223> OTHER INFORMATION: Primer

<400> SEQUENCE: 24
gcttgtgttc tgggatgaag atttc                                         25

<210> SEQ ID NO 25
<211> LENGTH: 23
<212> TYPE: DNA
<213> ORGANISM: Homo sapiens
<220> FEATURE:
<223> OTHER INFORMATION: Primer

<400> SEQUENCE: 25
cgtccaacaa tgtgacccag atg                                           23

<210> SEQ ID NO 26
<211> LENGTH: 23
<212> TYPE: DNA
<213> ORGANISM: Homo sapiens
<220> FEATURE:
<223> OTHER INFORMATION: Primer

<400> SEQUENCE: 26
ggtaggcagt cacggcaatg aac                                           23

<210> SEQ ID NO 27
<211> LENGTH: 24
<212> TYPE: DNA
<213> ORGANISM: Homo sapiens
<220> FEATURE:
<223> OTHER INFORMATION: Primer

<400> SEQUENCE: 27
gaccaaggct tcatctgtgg catc                                          24

<210> SEQ ID NO 28
<211> LENGTH: 22
<212> TYPE: DNA
<213> ORGANISM: Homo sapiens
<220> FEATURE:
<223> OTHER INFORMATION: Primer

<400> SEQUENCE: 28
gctgtttcca tggctacccc ac                                            22

<210> SEQ ID NO 29
<211> LENGTH: 20
<212> TYPE: DNA
<213> ORGANISM: Homo sapiens
<220> FEATURE:
<223> OTHER INFORMATION: Primer

<400> SEQUENCE: 29
gtcctgtgcg aactgtcaga                                               20

<210> SEQ ID NO 30
<211> LENGTH: 20
```

```
<212> TYPE: DNA
<213> ORGANISM: Homo sapiens
<220> FEATURE:
<223> OTHER INFORMATION: Primer

<400> SEQUENCE: 30
ctggatgcct tccttcttca                                            20

<210> SEQ ID NO 31
<211> LENGTH: 20
<212> TYPE: DNA
<213> ORGANISM: Homo sapiens
<220> FEATURE:
<223> OTHER INFORMATION: Primer

<400> SEQUENCE: 31
gctggccttt catcatcatc                                            20

<210> SEQ ID NO 32
<211> LENGTH: 20
<212> TYPE: DNA
<213> ORGANISM: Homo sapiens
<220> FEATURE:
<223> OTHER INFORMATION: Primer

<400> SEQUENCE: 32
ctttccacat gctggctaca                                            20

<210> SEQ ID NO 33
<211> LENGTH: 24
<212> TYPE: DNA
<213> ORGANISM: Homo sapiens
<220> FEATURE:
<223> OTHER INFORMATION: Primer

<400> SEQUENCE: 33
ctgggaagac ctcattggtg tcac                                       24

<210> SEQ ID NO 34
<211> LENGTH: 24
<212> TYPE: DNA
<213> ORGANISM: Homo sapiens
<220> FEATURE:
<223> OTHER INFORMATION: Primer

<400> SEQUENCE: 34
cggttatgga tgttcaggtt gacc                                       24

<210> SEQ ID NO 35
<211> LENGTH: 23
<212> TYPE: DNA
<213> ORGANISM: Homo sapiens
<220> FEATURE:
<223> OTHER INFORMATION: Primer

<400> SEQUENCE: 35 cctcccccctg gaattacact gtc                                       23

<210> SEQ ID NO 36
<211> LENGTH: 21
<212> TYPE: DNA
<213> ORGANISM: Homo sapiens
<220> FEATURE:
<223> OTHER INFORMATION: Primer

<400> SEQUENCE: 36
```
cagggtctct tgctggatgg g                                              21

<210> SEQ ID NO 37
<211> LENGTH: 30
<212> TYPE: DNA
<213> ORGANISM: Homo sapiens
<220> FEATURE:
<223> OTHER INFORMATION: Primer

<400> SEQUENCE: 37
gttgatcagc tgaaaaatta tgtgaatgac                                     30

<210> SEQ ID NO 38
<211> LENGTH: 25
<212> TYPE: DNA
<213> ORGANISM: Homo sapiens
<220> FEATURE:
<223> OTHER INFORMATION: Primer

<400> SEQUENCE: 38
gcaggaaaaa gctgaccact cacag                                          25

<210> SEQ ID NO 39
<211> LENGTH: 20
<212> TYPE: DNA
<213> ORGANISM: Homo sapiens
<220> FEATURE:
<223> OTHER INFORMATION: Primer

<400> SEQUENCE: 39
gagtcaacgg atttggtcgt                                                20

<210> SEQ ID NO 40
<211> LENGTH: 20
<212> TYPE: DNA
<213> ORGANISM: Homo sapiens
<220> FEATURE:
<223> OTHER INFORMATION: Primer

<400> SEQUENCE: 40
gacaagcttc ccgttctcag                                                20

<210> SEQ ID NO 41
<211> LENGTH: 599
<212> TYPE: PRT
<213> ORGANISM: Homo sapiens

<400> SEQUENCE: 41

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

-continued

```
Leu Ile Cys Gly Lys Asp Ile Ser Gly Tyr Pro Asp Ile Pro
        115                 120                 125

Asp Glu Val Thr Cys Val Ile Tyr Glu Tyr Ser Gly Asn Met Thr Cys
130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Lys Lys Tyr
                180                 185                 190

Leu Val Trp Val Gln Ala Ala Asn Ala Leu Gly Met Glu Glu Ser Lys
                195                 200                 205

Gln Leu Gln Ile His Leu Asp Asp Ile Val Ile Pro Ser Ala Ala Val
        210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
                260                 265                 270

Asn Phe Thr Tyr Val Gln Gln Ser Glu Phe Tyr Leu Glu Pro Asn Ile
                275                 280                 285

Lys Tyr Val Phe Gln Val Arg Cys Gln Glu Thr Gly Lys Arg Tyr Trp
                290                 295                 300

Gln Pro Trp Ser Ser Leu Phe His Lys Thr Pro Glu Thr Asp Asn
305                 310                 315                 320

Arg Gly Asp Ile Gly Leu Leu Leu Gly Met Ile Val Phe Ala Val Met
                325                 330                 335

Leu Ser Ile Leu Ser Leu Ile Gly Ile Phe Asn Arg Ser Phe Arg Thr
                340                 345                 350

Gly Ile Lys Arg Arg Ile Leu Leu Leu Ile Pro Lys Trp Leu Tyr Glu
                355                 360                 365

Asp Ile Pro Asn Met Lys Asn Ser Asn Val Val Lys Met Leu Gln Glu
370                 375                 380

Asn Ser Glu Leu Met Asn Asn Asn Ser Ser Glu Gln Val Leu Tyr Val
385                 390                 395                 400

Asp Pro Met Ile Thr Glu Ile Lys Glu Ile Phe Ile Pro Glu His Lys
                405                 410                 415

Pro Thr Asp Tyr Lys Lys Glu Asn Thr Gly Pro Leu Glu Thr Arg Asp
                420                 425                 430

Tyr Pro Gln Asn Ser Leu Phe Asp Asn Thr Thr Val Val Tyr Ile Pro
                435                 440                 445

Asp Leu Asn Thr Gly Tyr Lys Pro Gln Ile Ser Asn Phe Leu Pro Glu
        450                 455                 460

Gly Ser His Leu Ser Asn Asn Asn Glu Ile Thr Ser Leu Thr Leu Lys
465                 470                 475                 480

Pro Pro Val Asp Ser Leu Asp Ser Gly Asn Asn Pro Arg Leu Gln Lys
                485                 490                 495

His Pro Asn Phe Ala Phe Ser Val Ser Ser Val Asn Ser Leu Ser Asn
                500                 505                 510

Thr Ile Phe Leu Gly Glu Leu Ser Leu Ile Leu Asn Gln Gly Glu Cys
                515                 520                 525

Ser Ser Pro Asp Ile Gln Asn Ser Val Glu Glu Glu Thr Thr Met Leu
```

|     |     | 530 |     |     |     | 535 |     |     |     | 540 |     |
| --- | --- | --- | --- | --- | --- | --- | --- | --- | --- | --- | --- |

Leu Glu Asn Asp Ser Pro Ser Glu Thr Ile Pro Glu Gln Thr Leu Leu
545                 550                 555                 560

Pro Asp Glu Phe Val Ser Cys Leu Gly Ile Val Asn Glu Glu Leu Pro
                565                 570                 575

Ser Ile Asn Thr Tyr Phe Pro Gln Asn Ile Leu Glu Ser His Phe Asn
            580                 585                 590

Arg Ile Ser Leu Leu Glu Lys
        595